US009371352B2

(12) United States Patent
Porcelli et al.

(10) Patent No.: US 9,371,352 B2
(45) Date of Patent: Jun. 21, 2016

(54) MODIFIED GLYCOLIPIDS AND METHODS OF MAKING AND USING THE SAME

(71) Applicants: Vaccinex, Inc., Rochester, NY (US); Albert Einstein College of Medicine, Inc., Bronx, NY (US)

(72) Inventors: Steven A. Porcelli, Hartsdale, NY (US); Maurice Zauderer, Pittsford, NY (US)

(73) Assignees: VACCINEX, INC., Rochester, NY (US); ALBERT EINSTEIN COLLEGE OF MEDICINE, INC., Bronx, NY (US)

(*) Notice: Subject to any disclaimer, the term of this patent is extended or adjusted under 35 U.S.C. 154(b) by 0 days.

(21) Appl. No.: 13/803,972

(22) Filed: Mar. 14, 2013

(65) Prior Publication Data
US 2014/0227296 A1    Aug. 14, 2014

Related U.S. Application Data

(60) Provisional application No. 61/762,591, filed on Feb. 8, 2013.

(51) Int. Cl.
*C07H 15/18* (2006.01)
*A61K 47/48* (2006.01)
*C07H 15/10* (2006.01)

(52) U.S. Cl.
CPC ............ *C07H 15/18* (2013.01); *A61K 47/4833* (2013.01); *C07H 15/10* (2013.01)

(58) Field of Classification Search
CPC .......................... A61K 47/48092; C07H 15/18
USPC ......................................................... 536/17, 9
See application file for complete search history.

(56) References Cited

U.S. PATENT DOCUMENTS

| | | |
|---|---|---|
| 4,690,915 A | 9/1987 | Rosenberg |
| 5,081,029 A | 1/1992 | Zarling et al. |
| 5,194,425 A | 3/1993 | Sharma et al. |
| 5,264,618 A | 11/1993 | Felgner et al. |
| 5,635,363 A | 6/1997 | Altman et al. |
| 5,679,347 A | 10/1997 | Porcelli et al. |
| 5,780,441 A | 7/1998 | Higa et al. |
| 5,849,716 A | 12/1998 | Akimoto et al. |
| 5,853,737 A | 12/1998 | Modlin et al. |
| 5,936,076 A | 8/1999 | Higa et al. |
| 6,015,884 A | 1/2000 | Schneck et al. |
| 6,162,609 A | 12/2000 | Hafler et al. |
| 6,238,676 B1 | 5/2001 | Porcelli et al. |
| 6,248,564 B1 | 6/2001 | Walter et al. |
| 6,531,453 B1 | 3/2003 | Taniguchi et al. |
| 6,548,067 B1 | 4/2003 | Seeman et al. |
| 6,682,741 B1 | 1/2004 | Ribaudo et al. |
| 6,747,010 B2 | 6/2004 | Taniguchi et al. |
| 6,881,828 B2 | 4/2005 | Edwards et al. |
| 7,273,852 B2 | 9/2007 | Tsuji et al. |
| 7,666,656 B2 | 2/2010 | Sun et al. |
| 7,772,380 B2 | 8/2010 | Porcelli |
| 8,022,043 B2 | 9/2011 | Porcelli |
| 2002/0051783 A1 | 5/2002 | Savage |
| 2002/0071842 A1 | 6/2002 | Gumperz et al. |
| 2002/0155447 A1 | 10/2002 | Zauderer et al. |
| 2003/0157135 A1 | 8/2003 | Tsuji et al. |
| 2003/0166277 A1 | 9/2003 | Zauderer et al. |
| 2004/0091488 A1 | 5/2004 | Seeman et al. |
| 2004/0096429 A1 | 5/2004 | Savage |
| 2004/0127429 A1 | 7/2004 | Tsuji |
| 2004/0210037 A1 | 10/2004 | Zauderer et al. |
| 2005/0042218 A1 | 2/2005 | Zauderer |
| 2005/0112141 A1 | 5/2005 | Terman |
| 2005/0192248 A1 | 9/2005 | Tsuji et al. |
| 2006/0019246 A1 | 1/2006 | Tsuji et al. |
| 2006/0052316 A1 | 3/2006 | Porcelli |
| 2006/0074235 A1 | 4/2006 | Annoura et al. |
| 2006/0116331 A1 | 6/2006 | Jiang et al. |
| 2006/0148723 A1 | 7/2006 | Yamamura et al. |
| 2006/0211856 A1* | 9/2006 | Tsuji et al. ...................... 536/53 |
| 2006/0269540 A1 | 11/2006 | Robert et al. |
| 2007/0238673 A1 | 10/2007 | Porcelli |
| 2007/0287664 A1 | 12/2007 | Ralston et al. |
| 2007/0292418 A1 | 12/2007 | Fields et al. |
| 2008/0254045 A1 | 10/2008 | Donda et al. |
| 2010/0183549 A1 | 7/2010 | Porcelli et al. |
| 2013/0164325 A1 | 6/2013 | Porcelli et al. |

FOREIGN PATENT DOCUMENTS

| | | |
|---|---|---|
| AU | A-39005/89 | 2/1990 |
| AU | B-39005/89 | 2/1990 |
| EP | 0 133 988 A2 | 3/1985 |
| EP | 0 352 761 | 1/1990 |
| GB | 2 339 782 A | 2/2000 |

(Continued)

OTHER PUBLICATIONS

Sonnino et al, "A Photoreactive Derivative of Radiolabeled GM1 Ganglioside" Biochemistry, vol. 28, (1989), pp. 77-84.*
Hashimoto et al, Bioorganic & medicinal chemistry letters, vol. 12, No. 1 (2002), pp. 89-91.*
Abastado, J-P., et al., "Dimerization of Soluble Major Histocompatibility Complex-Peptide Complexes Is Sufficient for Activation of T Cell Hybridoma and Induction of Unresponsiveness," *J. Exp. Med.*, 1995, vol. 182, pp. 439-447.
Abdel-Wahab, Z., et al., "Human Dendritic Cells, Pulsed with either Melanoma Tumor Cell Lysates or the gp100 Peptide$_{(280-288)}$, Induce Pairs of T-Cell Cultures with Similar Phenotype and Lytic Activity," *Cellular Immunol.*, 1998, vol. 186, pp. 63-74.
Alexander, J., et al., "Recognition of a Novel Naturally Processed, A2 Restricted, HCV-NS4 Epitope Triggers IFN-gamma Release in Absence of Detectable Cytopathicity," *Human Immunol.*, 1998, vol. 59, pp. 776-782.

(Continued)

*Primary Examiner* — Jonathan S Lau
(74) *Attorney, Agent, or Firm* — Womble Carlyle Sandridge & Rice, LLP

(57) ABSTRACT

The invention is directed to compositions and methods related to proteins that are physically associated with ceramide-like glycolipids for use as activators of NKT cells. The compositions and methods of the present invention are useful for the prevention and treatment of diseases.

29 Claims, 12 Drawing Sheets

(56) References Cited

FOREIGN PATENT DOCUMENTS

| WO | WO 93/10220 | 5/1993 |
|---|---|---|
| WO | WO-94/24142 | 10/1994 |
| WO | WO 94/25610 | 11/1994 |
| WO | WO 96/26962 | 9/1996 |
| WO | WO 97/35991 | 10/1997 |
| WO | WO 98/07441 | 2/1998 |
| WO | WO-98/23627 | 6/1998 |
| WO | WO98/23627 | 6/1998 |
| WO | WO-98/44928 | 10/1998 |
| WO | WO 99/11775 | 3/1999 |
| WO | WO 99/13095 | 3/1999 |
| WO | WO 99/21572 | 5/1999 |
| WO | WO 99/31241 | 6/1999 |
| WO | WO 99/64464 | 12/1999 |
| WO | WO 99/64597 | 12/1999 |
| WO | WO 00/00156 | 1/2000 |
| WO | WO 01/44296 A1 | 6/2001 |
| WO | WO 01/71005 A2 | 9/2001 |
| WO | WO 01/72995 A2 | 10/2001 |
| WO | WO-01/78768 A2 | 10/2001 |
| WO | WO 01/90198 A1 | 11/2001 |
| WO | WO-02/27027 A2 | 4/2002 |
| WO | WO03/009812 A2 | 2/2003 |
| WO | WO-03/016326 | 2/2003 |
| WO | WO2004/028475 A2 | 4/2004 |
| WO | WO 2004/029206 A2 | 4/2004 |
| WO | WO2004/072091 A1 | 8/2004 |
| WO | WO 2005/000348 A2 | 1/2005 |
| WO | WO2006/026389 A2 | 3/2006 |
| WO | WO2007/007946 A1 | 1/2007 |
| WO | WO 2008/103392 A2 | 8/2008 |
| WO | WO2008/133801 A1 | 11/2008 |
| WO | WO2008/140598 A2 | 11/2008 |
| WO | WO2010/081026 A1 | 7/2010 |
| WO | WO-2012/006342 A1 | 1/2012 |

OTHER PUBLICATIONS

Alexander, M., et al., "Generation of tumor-specific cytolytic T lymphocytes from peripheral blood of cervical cancer patients by in vitro stimulation with a synthetic human papillomavirus type 16 E7 epitope," *Am. J. Obstet. Gynecol.*, 1996, vol. 175, pp. 1586-1593.

Altman, J. D., et al., "Phenotypic Analysis of Antigen-Specific T Lymphocytes," *Science*, 1996, vol. 274, pp. 94-96.

Andersen, P., et al., "Tuberculosis vaccines—an update," *Nature Reviews Microbiology*, 2007, vol. 5, pp. 484-487.

Balasubramanian, V., et al., "Mycobacterial Infection in Guinea Pigs," *Immunobiology*, 1994, vol. 191(4-5), pp. 395-401.

Balk, S. P., et al., "Isolation and characterization of a cDNA and gene coding for a fourth CD1 molecule," *Proc. Natl. Acad. Sci. USA*, 1989, vol. 86, pp. 252-256.

Barclay, W., et al., "Aerosol-Induced Tuberculosis in Subhuman Primates and the Course of the Disease After Intravenous BCG Vaccination," *Infect. Immun.*, 1970, vol. 2(5), pp. 574-582.

Battegay, M., et al., "Patients with Chronic Hepatitis C Have Circulating Cytotoxic T Cells Which Recognize Hepatitis C Virus-Encoded Peptides Binding to HLA-A2.1 Molecules," *J. Virology*, 1995, vol. 69, No. 4, pp. 2462-2470.

Beaudoin, L., et al., "NKT Cells Inhibit the Onset of Diabetes by Impairing the Development of Pathogenic T Cells Specific for Pancreatic β Cells," *Immunity*, 2002, vol. 17, pp. 725-736.

Bedzyk, W., et al., "Immunological and Structural Characterization of a High Affinity Anti-fluorescein Single-chain Antibody," *The Journal of Biological Chemistry*, 1990, vol. 265(30), pp. 18615-18620.

Behar, S., et al., "CD1-restricted T cells in host defense to infectious diseases," *Curr. Top. Microbiol. Immunol.*, 2007, vol. 314, pp. 215-250.

Behar, S., et al., "Susceptibility of Mice Deficient in CD1D or TAP1 to Infection with *Mycobacterium tuberculosis*," *J. Exp. Med.*, 1999, vol. 189(12), pp. 1973-1980.

Bendelac, A., "Mouse NK1$^+$T cells," *Current Opinion in Immunology*, 1995, vol. 7, pp. 367-374.

Bendelac, A., et al., "CD1 Recognition by Mouse NK1$^+$T Lymphocytes," *Science*, 1995, vol. 268, pp. 863-865.

Bendelac, A., et al., "Mouse CD-1 Specific NK1 T Cells: Development, Specificity, and Function," *Annual Review Immunol.*, 1997, vol. 15, pp. 535-562.

Bendle. G., et al., "A Study of T Cell Tolerance to the Tumor-Associated Antigen MDM2: Cytokines Can Restore Antigen Responsiveness, but Not High Avidity T Cell Function," *PLos One*, Apr. 2007, vol. 353(4), pp. 1-9.

Benlagha, K., et al., "In Vivo Identification of Glycolipid Antigen-specific T Cells Using Fluorescent CD1d Tetramers," *J. Exp. Med.*, 2000, vol. 191(11), pp. 1895-1903.

Bertoletti, A., et al., "Molecular Features of the Hepatitis B Virus Nucleocapsid T-Cell Epitope 18-27: Interaction With HLA and T Cell Receptor," *Hepatology*, 1997, vol. 26, pp. 1027-1034.

Bhat, S., et al., "Galactosyl ceramide or a derivative is an essential component of the neural receptor for human immunodeficiency virus type 1 envelope glycoprotein gp120," *Proc. Natl. Acad. Sci.*, 1991, vol. 88, pp. 7131-7134.

Bocchia, M., et al., "Specific Binding of Leukemia Oncogene Fusion Protein Peptides to HLA Class I Molecules," *Blood*, 1995, vol. 85, No. 10, pp. 2680-2684.

Bocchia, M., et al., "Specific Human Cellular Immunity to bcr-abl Oncogene-Derived Peptides," *Blood*, 1996, vol. 87, No. 9, pp. 3587-3592.

Boitel, B., et al., "Strong Similarities in Antigen Fine Specificity Among DRB1*1302-Restricted Tetanus Toxin tt830-843-Specific TCRs in Spite of Highly Heterogeneous CDR3," *J. Immunol.*, 1995, vol. 154, pp. 3245-3255.

Boniface, J.J., et al., "Initiation of Signal Transduction through the T Cell Receptor Requires the Multivalent Engagement of Peptide/MHC Ligands," *Immunity*, 1998, vol.9, pp. 459-466.

Bonish, B., et al., "Overexpression of CD1d by Keratinocytes in Psoriasis and CD1d-Dependent IFN-γ Production by NK-T Cells," *J. Immunol.*, 2000, vol. 165, pp. 4076-4085.

Brinckerhoff, L. H., et al., "Terminal Modifications Inhibit Proteolytic Degradation of an Immunogenic Mart-1$_{27-35}$ Peptide: Implications for Peptide Vaccines," *Int. J. Cancer*, 1999, vol. 83, pp. 326-334.

Brossay, L., et al., "Cutting Edge: Structural Requirements for Galactosylceramide Recognition by CD1-Restricted NK T Cells," *Journal of Immunology*, 1998, vol. 161, pp. 5124-5128.

Brusic, V., et al., "Prediction of MHC class II-binding peptides using an evolutionary algorithm and artificial neural network," *Bioinformatics*, 1998, vol. 14, No. 2, pp. 121-130.

Burdin, N., et al., "Immunization with α-galactosylceramide polarizes CD1-reactive NK T cells toward Th2 cytokine synthesis," *Eur. J. Immunol.*, 1999, vol. 29, pp. 2014-2025.

Burrows, G. G., et al., "Two-Domain Class II Molecules Form Stable Complexes with Myelin Basic Protein 69-89 Peptide That Detect and Inhibit Rat Encephalitogenice T Cells and Treat Experimental Autoimmune Encephalomyelitis," *J. Immunol*, 1998, pp. 5987-5996.

Bynoe, M., et al., "Estrogen up-regulates Bcl-2 and blocks tolerance induction of naïve B cells," *PNAS*, 2000, vol. 97(6), pp. 2703-2708.

Bynoe, M., et al., "Characterization of anti-DNA B cells that escape negative selection," *Eur. J. Immunol.*, 1999, vol. 29, pp. 1304-1313.

Carnaud, C., et al., "Cutting Edge: Cross-Talk Between Cells of the Innate Immune System: NKT Cells Rapidly Activate NK Cells," *J. Immunol.*, 1999, vol. 163, pp. 4647-4650.

Casares, S., et al., "Antigen-specific Signaling by a Soluble, Dimeric Peptide/Major Histocompatibility Complex Class II/Fc Chimera Leading to T Helper Cell Type 2 Differentiation," *J. Exp. Med.*, 1999, vol. 190, No. 4, pp. 543-553.

Castelli, C., et al., "Novel HLA-Cw8-Restricted T Cell Epitopes Derived from Tyrosinase-Related Protein-2 and gp100 Melanoma Antigens," *J. Immunol.*, 1999, vol. 162, pp. 1739-1748.

Cayabyab, M.J., et al., "Recombinant *Mycobacterium bovis* BCG Prime-Recombinant Adenovirus Boost Vaccination in Rhesus Monkeys Elicits Robust Polyfunctional Simian Immunodeficiency Virus-Specific T-Cell Responses," *Journal of Virology*, 2009, vol. 83, No. 11, pp. 5505-5513.

(56) References Cited

OTHER PUBLICATIONS

Celis, E., et al., "Identification of Potential CTL Epitopes of Tumor-Associated Antigen MAGE-1 for Five Common HLA-A Alleles," *Mol. Immunol.*, 1994, vol. 31, No. 18, pp. 1423-1430.
Chackerian, A., et al., "Activation of NKT Cells Protects Mice from Tuberculosis," *Infection and Immunity*, 2002, vol. 70(11), pp. 6302-6309.
Chang, Y-T., et al., "The Synthesis and Biological Characterization of a Ceramide Library," *J. Am. Chem. Soc.*, 2002, vol. 124(9), pp. 1856-1857.
Chaux, P., et al., "Identification of MAGE-3 Epitopes Presented by HLA-DR Molecules to CD4+T Lymphocytes," *J. Exp. Med.*, 1999, vol. 189, No. 5, pp. 767-777.
Chen, H., et al., "Cultured NK1.1+CD4+ T Cells Produce Large Amounts of IL-4 and IFN-γ Upon Activation by Anti-CD3 or CD1," *The Journal of Immunology*, 1997, vol. 159, pp. 2240-2249.
Chikamatsu, K., et al., "Generation of Anti-p53 Cytotoxic T Lymphocytes from Human Peripheral Blood Using Autologous Dendritic Cells," *Clin. Cancer Res.*, 1999, vol. 5, pp. 1281-1288.
Cochran, J. R., et al., "The Relationship of MHC-Peptide Binding and T Cell Activation Probed Using Chemically Defined MHC Class II Oligomers," *Immunity*, 2000, vol. 12, pp. 241-250.
Cook, P., et al., "Alternatively activated dendritic cells regulate CD4+ T-cell polarization in vitro and in vivo," *PNAS*, 2012, vol. 109(25), pp. 9977-9982.
Cormier, J. N., et al., "Heterogeneous Expression of Melanoma-Associated Antigens and HLA-A2 in Metastatic Melanoma in vivo," *Int. J. Cancer*, 1998, vol. 75, pp. 517-524.
Crowe, N., et al., "Glycolipid Antigen Drives Rapid Expansion and Sustained Cytokine Production by NK T Cells," *J Immunol.*, 2003, vol. 171, pp. 4020-4027.
Cui, J., et al., "Requirement for $V_\alpha 14$ NKT Cells in IL-12-Mediated Rejection of Tumors," *Science*, 1997, vol. 278, pp. 1623-1626.
Dal Porto, J., et al., "A soluble divalent class I major histocompatibility complex molecule inhibits alloreactive T cells at nanomolar concentrations," *Proc. Natl. Acad. Sci. USA*, 1993, vol. 90, pp. 6671-6675.
Daniel, S., et al., "Relationship Between Peptide Selectivities of Human Transporters Associated with Antigen Processing and HLA Class I Molecules," *J. Immunol.*, 1998, vol. 161, pp. 617-624.
Davodeau, F., et al., "Close Phenotypic and Functional Similarities Between Human and Murine αβ T Cells Expressing Invariant TCR α-Chains," *J. Immunol.*, 1997, vol. 158, pp. 5603-5611.
De Backer, O., et al., "Characterization of the GAGE Genes That Are Expressed in Various Human Cancers and in Normal Testis," *Cancer Res.*, 1999, vol. 59, pp. 3157-3165.
De St. Groth, B. F., et al., "T cell activation: in vivo veritas," *Immunology and Cell Biology*, 2004, vol. 82, pp. 260-268.
Diepolder, H. M., et al., "Immunodominant CD4+ T-Cell Epitope within Nonstructural Protein 3 in Acute Hepatitis C Virus Infection," *J. Virol.*, 1997, vol. 71, No. 8, pp. 6011-6019.
Donda, A., et al., "In vivo targeting of an anti-tumor antibody coupled to antigenic MHC class I complexes induces specific growth inhibition and regression of established syngeneic tumor grafts," *Cancer Immunity*, 2003, vol. 3, p. 11.
Dondji, B., et al., "Intradermal NKT cell activation during DNA priming in heterologous prime-boost vaccination enhances T cell responses and protection against *Leishmania*," *Eur. J. Immunol.* 2008, vol. 38, pp. 706-719.
Doolan, D. L., et al., "Degenerate Cytotoxic T Cell Epitopes from P. falciparum Restricted by Multiple HLA-A and HLA-B Supertype Alleles," *Immunity*, 1997, vol. 7, pp. 97-112.
Dutronc, Y. and Porcelli, S. A., "The CD1 family and T cell recognition of lipid antigens," *Tissue Antigens*, 2002, vol. 60, pp. 337-353.
Eberl, G., et al., "Rapid Death and Regeneration of NKT Cells in Anti-CD3ε- or IL-12-Treated Mice: A Major Role for Bone Marrow in NKT Cell Homeostasis," *Immunity*, 1998, vol. 9, pp. 345-353.
Eberl, G., et al., "Selective induction of NK cell proliferation and cytotoxicity by activated NKT cells," *Eur. J. Immunol.*, 2000, vol. 30, pp. 985-992.

Emoto, M., et al., "Induction of IFN-γ-producing CD4+ natural killer T cells by *Mycobacterium bovis* bacillus Calmette Guérin," *Eur. J. Immunol.*, 1999, vol. 29, pp. 650-659.
Enomoto, N., et al., "Immunization with dendritic cells loaded with α-galactosylceramide at priming phase, but not at boosting phase, enhances cytotoxic T lymphocyte activity against infection by intracellular bacteria," *FEMS Immunol. Med. Microbiol.*, 2007, vol. 51, pp. 350-362.
Esser, S., et al., "Vascular endothelial growth factor induces VE-cadherin tryosine phosphorylation in endothelial cells," *J. Cell Science*, 1998, vol. 111, pp. 1853-1865.
Exley, M., et al., "Requirements for CD1d Recognition by Human Invariant $V\alpha 24^+ CD4^- CD8^-$ T Cells," *J. Exp. Med.*, 1997, vol. 186(1), pp. 109-120.
Fayen, J., et al., "Class I MHC Alpha 3 Domain Can Function as an Independent Structural Unit to Bind CD8α," *Mol. Immunol.* 1995, vol. 32, No. 4, pp. 267-275.
Fischer, K., et al., "Mycobacterial phosphatidylinositol mannoside is a natural antigen for CD1d-restricted T Cells," *PNAS*, 2004, vol. 101(29), pp. 10685-10690.
Fleischhauer, K., et al., "Functional Heterogeneity of HLA-A*02 Subtypes Revealed by Presentation of a MAGE-3-Encoded Peptide to Cytotoxic T Cell Clones," *J. Immunol.*, 1997, vol. 159, pp. 2513-2521.
Florence, W., et al., "CD1d-restricted glycolipid antigens: presentation principles, recognition logic and functional consequences," *Expert Reviews in Molecular Medicine*, 2008, vol. 10(e20), pp. 1-27.
Flynn, J., et al., "Major histocompatibility complex class I-restricted T cells are required for resistance to *Mycobacterium tuberculosis* infection," *Proc. Natl. Acad. Sci.*, 1992, vol. 89, pp. 12013-12017.
Freidag, B., et al., "CpG Oligodeoxynucleotides and Interleukin-12 Improve the Efficacy of *Mycobacterium bovis* BCG Vaccination in Mice Challenged with *M. tuberculosis*," *Infect. Immun.*, 2000, vol. 68(5), pp. 2948-2953.
Fujii, S., et al., "Prolonged IFN-γ-producing NKT response induced with α-galactosylceramide-loaded DCs," *Nature Immunology*, 2002, vol. 3, pp. 967-975.
Fujii, S., et al., "Activation of Natural Killer T Cells by α-Galactosylceramide Rapidly Induces the Full Maturation of Dendritic Cells In Vivo and Thereby Acts as an Adjuvant for Combined CD4 and CD8 T Cell Immunity to a Coadministered Protein," *J. Exp. Med.*, 2003, vol. 198(2), pp. 267-279.
Fujii, S., et al., "Glycolipid α-C-galactosylceramide is a distinct inducer of dendritic cell function during innate and adaptive immune responses of mice," *PNAS*, 2006, vol. 103(30), pp. 11252-11257.
Fujii, S., et al., "Innate Vα14+ natural killer T cells mature dendritic cells, leading to strong adaptive immunity," *Immunol. Rev.*, 2007, vol. 220, pp. 183-198.
Galli, G., et al., "Invariant NKT cells sustain specific B cell responses and memory," *PNAS*, 2007, vol. 104(10), pp. 3984-3989.
Gaynor, B., et al., "Peptide inhibition of glomerular deposition of an anti-DNA antibody," *Proc. Natl. Acad. Sci.*, 1997, vol. 94, pp. 1955-1960.
Glick, M., et al., "Novel CD8+ T Cell Antagonist Based on $β_2$-Microglobulin," *The Journal of Biological Chemistry*, 2002, vol. 277, No. 23, pp. 20840-20846.
Godfrey, D., et al., "NKT cells: facts, functions and fallacies," *Immunol. Today*, 2000, vol. 21(11), pp. 573-583.
Gonzalez-Aseguinolaza, G., et al., "Natural Killer T Cell Ligand α-Galactosylceramide Enhances Protective Immunity Induced by Malaria Vaccines," *J. Exp. Med.*, 2002, vol. 195(5), pp. 617-624.
Gonzalez-Aseguinolaza, G., et al., "α-Galactosylceramide-activated Vα14 natural killer T cells mediate protection against murine malaria," *PNAS*, 2000, vol. 97(15), pp. 8461-8466.
Gotch, F., et al., "Cytotoxic T lymphocytes recognize a fragment of influenza virus matrix protein in association with HLA-A2," *Nature*, 1987, vol. 326, pp. 881-883.
Greten, T. F., et al., "Direct visualization of antigen-specific T cells: HTLV-1 Tax11-19-specific CD8+ T cells are activated in peripheral blood and accumulate in cerebrospinal fluid from HAM/TSP patients," *Proc. Natl. Acad. Sci. USA*, 1998, vol. 95, pp. 7568-7573.

(56) References Cited

OTHER PUBLICATIONS

Grode, L., et al., "Increased vaccine efficacy against tuberculosis of recombinant *Mycobacterium bovis* bacille Calmette-Guérin mutants that secrete listeriolysin," *Journal of Clinical Investigation*, 2005, vol. 115(9), pp. 2472-2479.
Gumperz, J., et al., "Functionally Distinct Subsets of CD1d-restricted Natural Killer T Cells Revealed by CD1d Tetramer Straining," *J. Exp. Med.*, 2002, vol. 195(5), pp. 625-636.
Hahn, B., "Antibodies to DNA," *New England Journal of Medicine*, 1998, vol. 338(19), pp. 1359-1368.
Hamad, A. R. A., et al., "Potent T Cell Activation with Dimeric Peptide-Major Histocompatibility Complex Class II Ligand: The Role of CD4 Coreceptor," *J. Exp. Med.*, 1998, vol. 188, No. 9, pp. 1633-1640.
Hammond, K., et al., "α/β-T Cell Receptor (TCR)$^+$CD4$^-$CD8$^-$ (NKT) Thymocytes Prevent Insulin-dependent Diabetes Mellitus in Nonobese Diabetic (NOD)/Lt Mice by the Influence of Interleukin (IL)-4 and/or IL-10," *J. Exp. Med.*, 1998 vol. 187(7) pp. 1047-1056.
Harbury, P. B., et al., "A Switch Between Two-, Three-, and Four-Stranded Coiled Coils in GCN4 Leucine Zipper Mutants," *Science*, 1993, vol. 262, pp. 1401-1407.
Harvill, E. T., et al., "In Vivo Properties of an IgG3-IL-2 Fusion Protein," *J. Immunol.*, 1996, vol. 157, pp. 3165-3170.
Hayakawa, Y., et al., "Critical contribution of IFN-γ and NK cells, but not perforin-mediated cytotoxicity, to anti-metastatic effect of α-galactosylceramide," *Eur. J. Immunol.*, 2001, vol. 31, pp. 1720-1727.
Heathcote, J., et al., "A Pilot Study of the CY-1899 T-Cell Vaccine in Subjects Chronically Infected With Hepatitis B Virus," *Hepatology*, 1999, vol. 30, pp. 531-536.
Hebert, A. M., et al., "Kinetics and Thermodynamics of β2-Microglobulin Binding to the α3 Domain of Major Histocompatibility Complex Class I Heavy Chain," *Biochemistry*, 2001, vol. 40, pp. 5233-5242.
Hemmi, H., et al., "Small anti-viral compounds activate immune cells via the TLR7 MyD88-dependent signaling pathway," *Nature Immunol.*, 2002, vol. 3, No. 2, pp. 196-200.
Hermans, I., et al., "Dendritic Cell Function Can Be Modulated through Cooperative Actions of TLR Ligands and Invariant NKT Cells," *The Journal of Immunology*, 2007, vol. 178, pp. 2721-2729.
Hermans, I., et al., "NKT Cells Enhance CD4$^+$ and CD8$^+$ T Cell Responses to Soluble Antigen In Vivo through Direct Interaction with Dendritic Cells," *J. Immunol.*, 2003, vol. 171, pp. 5140-5147.
Hinchey, J., et al., "Enhanced priming of adaptive immunity by a proapoptotic mutant of *Mycobacterium tuberculosis*," *Journal of Clinical Investigation*, 2007, vol. 117(8), pp. 2279-2288.
Hochman, J. H., et al., "Specific Associations of Fluorescent β2-Microglobulin with Cell Surfaces; The Affinity of Different H-2 and HLA Antigens for β-2-Microglobulin," *The Journal of Immunology*, 1998, vol. 140, pp. 2322-2329.
Hoffmann, P., et al., "Large-scale in vitro expansion of polyclonal human CD4$^+$CD25$^{high}$ regulatory T Cells," *Blood*, 2004, vol. 104, No. 3, pp. 895-903.
Hoft, D., "Tuberculosis vaccine development: goals, immunological design, and evaluation," *Lancet*, 2008, vol. 372, pp. 164-175.
Höllsberg, P., et al., "Differential activation of proliferation and cytotoxicity in human T-cell lymphotropic virus type I Tax-specific CD8 T cells by an altered peptide ligand," *Proc. Natl. Acad. Sci. USA*, 1995, vol. 92, pp. 4036-4040.
Hong, S., et al., "The natural killer T-cell ligand α-galactosylceramide prevents autoimmune diabetes in non-obese diabetic mice," *Nature Medicine*, 2001, vol. 7(9), pp. 1052-1056.
Horwitz, M., et al., "Recombinant bacillus Calmette-Guérin (BCG) vaccines expressing the *Mycobacterium tuberculosis* 30-kDa major secretory protein induce greater protective immunity against tuberculosis than conventional BCG vaccines in a highly susceptible animal model," *PNAS*, 2000, vol. 97(25), pp. 13853-13858.
Huang, Y., et al., "Enhancement of HIV DNA vaccine immunogenicity by the NKT cell ligand, α-galactosylceramide," *Vaccine*, 2008, vol. 26, pp. 1807-1816.

Iborra, S., et al., "Vaccination with the *Leishmania major* ribosomal proteins plus CpG oligodeoxynucleotides induces protection against experimental cutaneous leishmaniasis in mice," *Microbes and Infection*, 2008, vol. 10, pp. 1133-1141.
Iijima, H., et al., "Structure-Activity Relationship and Conformational Analysis of Monoglycosylceramides on Syngeneic Mixed Leukocyte Reaction," *Bioorganic & Medicinal Chemistry*, 1998, vol. 6, pp. 1905-1910.
Illés Z., et al., "Differential Expression of NK T Cell Vα24JαQ Invariant TCR Chain in the Lesions of Multiple Sclerosis and Chronic Inflammatory Demyelinating Polyneuropathy," *J. Immunol.*, 2000, vol. 164, pp. 4375-4381.
Im, J. S., et al., "Direct Measurement of Antigen Binding Properties of CD1 Proteins Using Florescent Lipid Probes," *The Journal of Biological Chemistry*, 2004, vol. 279, pp. 299-310.
Inoue, H., et al., "α-Galactosylceramide (AGL-517) treatment protects mice from lethal irradiation," *Experimental Hematology*, 1997, vol. 25, pp. 935-944.
International Search Report for International Application No. PCT/US08/04546, United States Patent and Trademark Office, U.S.A., mailed on Jul. 30, 2008.
Ishikawa, H., et al., "CD4$^+$ V$_\alpha$14 NKT cells play a crucial role in an early stage of protective immunity against infection with *Leishmania major*," *Int. Immunol.*, 2000, vol. 12(9), pp. 1267-1274.
Jackman, R. M., et al., "Mechanisms of lipid antigen presentation by CD1," *Critical Reviews in Immunology*, 1999, vol. 19(1), pp. 49-63.
Jahng, A. W., et al., "Activation of Natural Killer T Cells Potentiates or Prevents Experimental Autoimmune Encephalomyelitis," *J Exp. Med.*, 2001, vol. 194, No. 12, pp. 1789-1799.
Joyce, S., et al., "Natural Ligand of Mouse CD1D1: Cellular Glycosylphosphatidylinositol," *Science*, 1998, vol. 279, pp. 1541-1544.
Kakimi, K., et al., "Natural Killer T Cell Activation Inhibits Hepatitis B Virus Replication In Vivo," *J. Exp. Med.*, 2000, vol. 192(7), pp. 921-930.
Kang, S., et al., "Saposins facilitate CD1d-restricted presentation of an exogenous lipid antigen to T cells," *Nature Immunology*, 2004, vol. 5, No. 2, pp. 175-181.
Karadimitris, A., et al., "Human CD1d-glycolipid tetramers generated by in vitro oxidative refolding chromatography," *PNAS*, 2001, vol. 98(6), pp. 3294-3298.
Kawakami, K., et al., "Activation of Vα14$^+$ Natural Killer T Cells by α-Galactosylceramide Results in Development of Th1 Response and Local Host Resistance in Mice Infected with *Cryptococcus neoformans*," *Infect. Immun.*, 2001, vol. 69(1), pp. 213-220.
Kawano, T., et al., "CD1d-Restricted and TCR-Mediated Activation of V$_\alpha$14 NKT Cells by Glycosylceramides," *Science*, 1997, vol. 278, pp. 1626-1629.
Kawashima, I., et al., "Identifitcation of gp100-Derived, Melanoma-Specific Cytotoxic T-Lymphocyte Epitopes Restricted by HLA-A3 Supertype Molecules by Primary in Vitro Immunization with Peptide-Pulsed Dendritic Cells," *Int. J. Cancer*, 1998, vol. 78, pp. 518-524.
Kawashima, I., et al., "Identification of HLA-A3-restricted Cytotoxic T Lymphocyte Epitopes from Carcinoembryonic Antigen and HER-2/ neu by Primary in Vitro Immunization with Peptide-pulsed Dendritic Cells," *Cancer Res.*, 1999, vol. 59, pp. 431-435.
Kim, J., et al., "Determinants of T Cell Reactivity to the *Mycobacterium leprae* GroES Homologue," *J. Immunol.*, 1997, vol. 159, pp. 335-343.
Kita, H., et al., "Quantitation and Phenotypic Analysis of Natural Killer T Cells in Primary Biliary Cirrhosis Using a Human CD1d Tetramer," *Gastroenterology*, 2002, vol. 123, pp. 1031-1043.
Kitamura, H., et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," *J. Exp. Med.*, 1999, vol. 189(7), pp. 1121-1127.
Kobayashi, E., et al., "Enhancing Effects of Agelasphin-11 on Natural Killer Cell Activities of Normal and Tumor-Bearing Mice," *Biol. Pharm. Bull.*, 1996, vol. 19(3), pp. 350-353.

(56) References Cited

OTHER PUBLICATIONS

Kobayashi, E., et al., "Enhancing Effects of α-, β-Monoglycosylceramides on Natural Killer Cell Activity," *Bioorganic & Medicinal Chemistry*, 1996, vol. 4(4), pp. 615-619.

Kobayashi, E., et al., "KRN7000, A Novel Immunomodulator, and Its Antitumor Activities," *Oncology Research*, 1995, vol. 7(10/11), pp. 529-534.

Kojo, S., et al., "Alternative Splicing Forms of the Human CD1D Gene in Mononuclear Cells," *Biochem. Biophys. Res. Comm.*, 2000, vol. 276, pp. 107-111.

Kojo, S., et al., "Dysfunction of T Cell Receptor AV24AJ18+, BV11+ Double-Negative Regulatory Natural Killer T Cells in Autoimmune Diseases," *Arthritis & Rheumatism*, 2001, vol. 44(5), pp. 1127-1138.

Kojo, S., et al., "Low Expression Levels of Soluble CD1d Gene in Patients with Rheumatoid Arthritis," *J. Rheumatol.*, 2003, vol. 30, pp. 2524-2528.

Kono, K., et al., "Identification of HER2/neu-Derived Peptide Epitopes Recognized by Gastric Cancer-Specific Cytotoxic T Lymphocytes," *Int J Cancer*, 1998, vol. 78, pp. 202-208.

Koseki, H., "Dominant expression of a distinctive V14$^+$ T-cell antigen receptor α chain in mice," *Proc. Natl. Acad. Sci.*, 1991, vol. 88, pp. 7518-7522.

Kotzin, B., "Systemic Lupus Erythematosus," *Cell*, 1996, vol. 85, pp. 303-306.

Kronenberg, M., "Toward an Understanding of NKT Cell Biology: Progess and Paradoxes," *Annu. Rev. Immunol.* 2005, vol. 26, pp. 877-900.

Kronenberg, M., et al., "The Unconventional Lifestyle of NKT Cells," *Nature Reviews Immunology*, 2002, vol. 2, pp. 557-568.

Kundu, S. K., et al., "Role of Preimmunization Virus Sequences in Cellular Immunity in HIV-Infected Patients during HIV Type 1 MN Recombinant gp 160 Immunization," *Aids Research and Human Retroviruses*, 1998, vol. 14, No. 18, pp. 1669-1678.

Kuo, P., et al., "Bcl-2 leads to expression of anti-DNA B cells but no nephritis: a model for a clinical subset," *Eur. J. Immunol.*, 1999, vol. 29, pp. 3168-3178.

Lachman, L. B., et al., "Cytokine-containing Liposomes as Adjuvants for Subunit Vaccines", Vaccine Design: The Subunit and Adjuvant Approach. (1995). New York, NY: Plenum Press, pp. 659-671.

Laloux, V., et al., "NK T Cell-Induced Protection Against Diabetes in Vα14-Jα281 Transgenic Nonobese Diabetic Mice Is Associated with a Th2 Shift Circumscribed Regionally to the Islets and Functionally to Islet Autoantigen," *Journal of Immunol.*, 2001, vol. 166, pp. 3749-3756.

Lee, A., et al., "Novel synthesis of α-galactosyl-ceramides and confirmation of their powerful NKT cell agonist activity," *Carbohydrate Res.*, 2006, vol. 341, pp. 2785-2798.

Lee, P., et al., "Distinct Functional Lineages of Human Vα24 Natural Killer T Cells," *J. Exp. Med.*, 2002, vol. 195(5), pp. 637-641.

Livingston, B. D., et al., "The Hepatitis B Virus-Specific CTL Responses Induced in Humans by Lipopeptide Vaccination Are Comparable to Those Elicited by Acute Viral Infection," *J. Immunol.*, 1997, vol. 159, pp. 1383-1392.

Livingston, P., et al., "Improved Survival in Stage III Melanoma Patients With GM2 Antibodies: A Randomized Trial of Adjuvant Vaccination With GM2 Ganglioside," *Journal of Clinical Oncology*, 1994, vol. 12(5), pp. 1036-1044.

Lutz, M., et al., "An advanced culture method for generating large quantities of highly pure dendritic cells from mouse bone marrow," *J. Immunol. Methods*, 1999, vol. 223, pp. 77-92.

Mallevaey, T., et al., "Invariant and Noninvariant Natural Killer T Cells Exert Opposite Regulatory Functions during Murine Schistosomiasis," *Infection and Immunity*, 2007, vol. 75, No. 5, pp. 2171-2180.

Manici, S., et al., "Melanoma Cells Present a MAGE-3 Epitope to CD4+ Cytotoxic T Cells in Association with Histocompatibility Leukocyte Antigen DR11," *J. Exp. Med.*, 1999, vol. 189, No. 5, pp. 871-876.

Matsuda, J., et al., "Tracking the Response of Natural Killer T Cells to a Glycolipid Antigen Using CD1d Tetramers," *J. Exp. Med.*, 2000, vol. 192(5), pp. 741-753.

Matsumoto, S., et al., "Recombinant *Mycobacterium bovis* Bacillus Calmette-Guérin Secreting Merozoite Surface Protein 1 (MSP1) Induces Protection against Rodent Malaria Parasite Infection Depending on MSP1-stimulated Interferon γ and Parasite-specific Antibodies," *J Exp. Med.*, 1998, vol. 188(5), pp. 845-854.

Matiner, J., et al., "Exogenous and endogenous glycolipid antigens activate NKT cells during microbial infections," *Nature*, 2005, vol. 434(7032), pp. 525-529.

Mieza, M., et al., "Selective Reduction of Vα14$^+$ NK T Cells Associated with Disease Development in Autoimmune-Prone Mice," *Journal of Immunol.*, 1996, vol. 156, pp. 4035-4040.

Minamino, M., et al., "Bacterial ceramides and sphingophospholipids induce apoptosis of human leukaemic cells," *Microbiology*, 2003, vol. 149, pp. 2071-2081.

Miyamoto, K., et al., "A synthetic glycolipid prevents autoimmune encephalomyelitis by inducing $T_H2$ bias of natural killer T cells," *Nature*, 2001, vol. 413, pp. 531-534.

Mogues, T., et al., "The Relative Importance of T Cell Subsets in Immunity and Immunopathology of Airborne *Mycobacterium tuberculosis* Infection in Mice," *J. Exp. Med.*, 2001, vol. 193(3), pp. 271-280.

Moody, D., et al., "The molecular basis of CD1-mediated presentation of lipid antigens," *Immunol. Rev.*, 1999, vol. 172, pp. 285-296.

Morita, M., et al., "Structure-Activity Relationship of α-Galactosylceramides against B16-Bearing Mice," *J. Med. Chem.*, 1995, vol. 38, pp. 2176-2187.

Morrison, S. L., et al., "Production and Characterization of Genetically Engineered Antibody Molcules," *Clin. Chem.*, 1988, vol. 34, No. 9, pp. 1668-1675.

Motoki, K., et al., "Effects of α-Galactosylceramides on Bone Marrow Cells in Vitro and Hematopoiesis in Vivo," *Biological & Pharmaceutical. Bulletin*, 1996, vol. 19(7), pp. 952-955.

Motoki, K., et al., "Immunostimulatory and Antitumor Activities of Monoglycosylceramides Having Various Sugar Moieties," *Biological & Pharmaceutical Bulletin*, 1995, vol. 18(11), pp. 1487-1491.

Mottiez, E., et al., "Cells Expressing a Major Histocompatibility Complex Class I Molecule with a Single Covalently Bound Peptide Are Highly Immunogenic," *J. Exp. Med.*, 1995, vol. 181, pp. 493-502.

Nagarajan, A. N., and Kronenberg, M., "Invariant NKT Cells Amplify the Innate Immune Response to Lipopolysaccharide," *The Journal of Immunology*, 2007, pp. 2706-2713.

Nagle, D., et al., "New Glycosphingolipids From the Marine Sponge *Halichondria panicea*," *Journal of Natural Products*, 1992, vol. 55(7), pp. 1013-1017.

Naidenko, O., et al., "Binding and Antigen Presentation of Ceramide-containing Glycolipids by Soluble Mouse and Human CD1d Molecules," *J. Exp. Med.*, 1999, vol. 190(8), pp. 1069-1079.

Nakagawa, R., et al., "Antitumor Activity of α-Galactosylceramide, KRN7000, in Mice With EL-4 Hepatic Metastasis and its Cytokine Production," *Oncology Research*, 1998, vol. 10, pp. 561-568.

Nakagawa, R., et al., "Antitumor Activity of α-Galactosylceramide, KRN7000, in Mice With the Melanoma B16 Hepatic Metastasis and Immunohistological Study of Tumor Infiltrating Cells," *Oncology Research*, 2000, vol. 12, pp. 51-58.

Naumov, Y. N., et al., "Activation of CD1d-restricted T cells protects NOD mice from developing diabetes by regulating dendritic cell subsets," *PNAS*, 2001, vol. 98, No. 24, pp. 13838-13843.

NCBI Entrez, GenBank Report, Accession No. NP 001009066 (Entry Date 2005), 2 pages.

NCBI Entrez, GenBank Report, Accession No. NP 001009284 (Entry Date 2005), 2 pages.

NCBI Entrez, GenBank Report, Accession No. NP 001065272 (Entry Date 2006), 2 pages.

NCBI Entrez, GenBank Report, Accession No. NP 001757 (Entry Date 1999), 4 pages.

NCBI Entrez, GenBank Report, Accession No. NP 004039 (Entry Date 1999), 3 pages.

NCBI Entrez, GenBank Report, Accession No. NP 031665 (Entry Date 2000), 3 pages.

(56) References Cited

OTHER PUBLICATIONS

NCBI Entrez, GenBank Report, Accession No. NP 033865 (Entry Date 2000), 3 pages.
NCBI Entrez, GenBank Report, Accession No. NP 036644 (Entry Date 2000), 3 pages.
NCBI Entrez, GenBank Report, Accession No. NP 058775 (Entry Date 2000), 2 pages.
NCBI Entrez, GenBank Report, Accession No. NP 999143 (Entry Date 2004), 2 pages.
NCBI Entrez, GenBank Report, Accession No. O62848 (Entry Date 2001), 3 pages.
NCBI Entrez, GenBank Report, Accession No. P01885 (Entry Date 1993), 3 pages.
NCBI Entrez, GenBank Report, Accession No. P23043 (Entry Date 1993), 3 pages.
NCBI Entrez, GenBank Report, Accession No. Q29422 (Entry Date 2001), 3 pages.
Nishimura, T., et al., "The interface between innate and acquired immunity: glycolipid antigen presentation by CD1d-expressing dendritic cells to NKT cells induces the differentiation of antigen-specific cytotoxic T lymphocytes," *Int. Immunol.*, 2000, vol. 12(7), pp. 987-994.
Nukaya, I., et al., "Identification of HLA-A24 Epitope Peptides of Carcinoembryonic Antigen Which Induce Tumor-Reactive Cytotoxic T Lymphocyte," *Int. J. Cancer*, 1999, vol. 80, pp. 92-97.
Ogg, G. S., et al., "Sensitization of tumour cells to lysis by virus-specific CTL using antibody-targeted MHC class I/peptide complexes," *British J. Cancer*, 2000, vol. 82, No. 5, pp. 1058-1062.
Oishi, Y., et al., "Selective Reduction and Recovery of Invariant Vα24JαQ T Cell Receptor T Cells in Correlation with Disease Activity in Patients with Systemic Lupus Erythematosus," *Journal of Rheumatology*, 2001, vol. 28(2), pp. 275-283.
Pack, P., et al., "Tetravalent Miniantibodies with High Avidity Assembling in *Escherichia coli*," *J. Mol. Biol.*, 1995, vol. 246, pp. 28-34.
Parekh, V. V., et al., "Glycolipid antigen induces long-term natural killer T cell anergy in mice," The Journal of Clinical Investigation, 2005, vol. 115, pp. 2572-2583.
Parekh, V. V., et al.,"The In Vivo Response of invariant Natural Killer T Cells to Glycolipid Antigens," 2007, *Int Rev Immunol*, vol. 26, pp. 31-48.
Parhman, P., et al., "Carbohydrate Moiety of HLA Antigens," *The Journal of Biological Chemistry*, 1977, vol. 252, No. 21, pp. 7555-7567.
Park, J-E., et al., "Fine specificity of natural killer T cells against GD3 ganglioside and identification of GM3 as an inhibitory natural killer T-cell ligand," *Immunology*, 2008, vol. 123, pp. 145-155.
Parker, K. C. And Strominger, J. L., "Subunit Interactions of Class I Histocompatibility Antigens," *Biochem.*, 1985, vol. 24, pp. 5543-5550.
Parkhurst, M. R., et al., "Identification of a Shared HLA-A*0201-restricted T-Cell Epitope from the Melanoma Antigen Turosinase-related Protein 2 (TRP2)," *Cancer Res.*, 1998, vol. 58, pp. 4895-4901.
Pavlinkova, G., et al., "Pharmacokinetics and biodistribution of a light-chain-shuffled CC49 single-chain Fv antibody construct," *Cancer Immunol Immunother*, 2000, vol. 49, pp. 267-275.
Peiper, M., et al., "Pancreatic Cancer Associated Ascites-Derived CTL Recognize a Nine-Amino-Acid Peptide GP2 Derived from HER2/neu," *Anticancer Res.*, 1999, vol. 19, pp. 2471-2476.
Penichet, M. L., et al., "An Antibody-Avidin Fusion Protein Specific for the Transferrin Receptor Serves as a Delivery Vehicle for Effective Brain Targeting: Initial Applications in Anti-HIV Antisense Drug Delivery to the Brain," *J. Immunol.*, 1999, vol. 163, pp. 4421-4426.
Peterson, P. A., et al., "β2-Microglobulin and the Major Histocompatibility Complex," *Adv. Cancer Res.*, 1977, vol. 24, pp. 115-163.
Pisetsky, D., "Systemic Lupus Erythematosus Diagnosis and Treatment," *The Medical Clinics of North America*, 1997, vol. 81(1), pp. 113-128.
Porcelli, S., "The CD1 Family: A Third Lineage of Antigen-Presenting Molecules," *Advances in Immunology*, 1995, vol. 59, pp. 1-98.

Porcelli, S., et al., "Analysis of T Cell Antigen Receptor (TCR) Expression by Human Peripheral Blood CD4⁻ 8⁻ α/β T Cells Demonstrates Preferential Use of Several Vβ Genes and an Invariant TCR α Chain," *J. Exp. Med.*, 1993, vol. 178, pp. 1-16.
Porcelli, S., et al., "The CD1 family of lipid antigen-presenting molecules," *Review Immunology Today*, 1998, vol. 19(8), pp. 362-368.
Porcelli, S., "The CD1 System: Antigen-Presenting Molecules for T Cell Recognition of Lipids and Glycolipids," *Annu. Rev. Immunol.*, 1999, vol. 17, pp. 297-329.
Porubsky, S., et al., "Normal developement and function of invariant natural killer T cells in mice with isoglobotrihexosylceramide (iGb3) deficiency," *PNAS*, 2007, vol. 104, No. 14, pp. 5977-5982.
Putterman, C., et al., "Immunization with a Peptide Surrogate for Double-stranded DNA (dsDNA) Induces Autoantibody Production and Renal Immunoglobulin Deposition," *J. Exp. Med.*, 1998, vol. 188(1), pp. 29-38.
Putterman, C., et al., "Molecular Analysis of the Autoantibody Response in Peptide-Induced Autoimmunity," *The Journal of Immunology*, 2000, vol. 164, pp. 2542-2549.
Ramakrishna, V., et al., "Generation and Phenotypic Characterization of New Human Ovarian Cancer Cell Lines With the Identification of Antigens Potentially Recognizable by HLA-Restricted Cytotoxic T Cells," *Int. J. Cancer*, 1997, vol. 73, pp. 143-150.
Ranson, T., et al., "Invariant Vα14⁺ NKT Cells Participate in the Early Response to Enteric *Listeria monocytogenes* Infection," *J. Immunol.*, 2005, vol.175, pp. 1137-1144.
Rao, V., et al. ,"*Mycobacterium tuberculosis* controls host inmate immune activation through cyclopropane modification of a glycolipid effector molecule," *J. Exp. Med.*, 2005, vol. 201(4), pp. 535-543.
Rao, V., et al., "Trans-cyclopropanation of mycolic acids on trehalose dimycolate suppresses *Mycobacterium tuberculosis*-induced inflammation and virulence," *J. Clin. Invest.*, 2006, vol. 116(6), pp. 1660-1167.
Reinhardt, C. and Melms, A., "Elevated frequencies of natural killer T lymphocytes in myasthenia gravis," *Neurology*, 1999, vol. 52, pp. 1485-1487.
Ressing, M. E., et al., "Human CTL Epitipes Encoded by Human Papillomavirus Type 16 E6 and E7 Identified Through In Vivo and In Vitro Immunogenicity Studies of HLA-A*0201-Binding Peptides," *J. Immunol.*, 1995, vol. 154, pp. 5934-5943.
Rivoltini, L., et al., "A Superagonist Variant of Peptide MART1/Melan A$_{27-35}$ Elicits Anti-Melanoma CD8⁺ T Cells with Enhanced Functional Characteristics: Implication for More Effective Immunotherapy," *Cancer Res.*, 1999, vol. 59, pp. 301-306.
Robert, B., et al., "Antibody-conjugated MHC class I tetramers can target tumor cells for specific lysis by T lymphocytes," *Eur. J. Immunol.*, 2000, vol. 30, pp. 3165-3170.
Robert, B., et al., "Redirecting anti-viral CTL against cancer cells by surface targeting of monomeric MHC class I-viral peptide conjugated to antibody fragments," *Cancer Immunity*, 2001, vol. 1, p. 2.
Rongcun, Y., et al., "Identification of New HER2/neu-Derived Peptide Epitopes That Can Elicit Specific CTL Against Autologous and Allogeneic Carcinomas and Melanomas," *J. Immunol.*, 1999, vol. 163, pp. 1037-1044.
Rötzschke, O., et al., "Conformational variants of class II MHC/peptide complexes induced by N- and C-terminal extensions of minimal peptide epitopes," *Proc. Natl. Acad. Sci. USA*, 1999, vol. 96, pp. 7445-7450.
Rötzschke, O., et al., "Superactivation of an immune response triggered by oligomerized T cell epitopes," *Proc. Natl. Acad. Sci. USA*, 1997, vol. 94, pp. 14642-14647.
Salazar-Onfray, F., et al., "Synthetic Peptides Derived from the Melanocyte-stimulating Hormone Receptor MC1R Can Stimulate HLA-A2-restricted Cytotoxic T Lymphocytes that Recognize Naturally Processed Peptides on Human Melanoma Cells," *Cancer Res.*, 1997, vol. 57, pp. 4348-4355.
Salter, R. D., et al., "A binding site for the T-cell co-receptor CD8 on the $\alpha_3$ domain of HLA-A2," *Nature*, 1990, vol. 345, pp. 41-46.

(56) References Cited

OTHER PUBLICATIONS

Saubermann, L. J., et al., "Activation of Natural Killer T Cell by α-Galactosylceramide in the Presence of CD1d Provides Protection Against Colitis in Mice," *Gastroenterology*, 2000, vol. 119, pp. 119-128.

Schmieg, J., "Superior Protection against Malaria and Melanoma Metastases by a C-glycoside Analogue of the Natural Killer T Cell Ligand α-Galactosylceramide," *J. Exp. Med.*, 2003, vol. 198(11), pp. 1631-1641.

Schmitt, L., et al., "Catalysis of peptide dissociation from class II MHC-peptide complexes," *Proc. Natl. Acad. Sci. USA*, 1999, vol. 96, pp. 6581-6586.

Schnell, S., et al., "Retrovirally Transduced Mouse Dendritic Cells Require CD4+ T Cell Help to Elicit Antitumor Immunity: Implications for the Clinical Use of Dendritic Cells," *J. Immunol.*, 2000, vol. 164, pp. 1243-1250.

Schwartz, M., and Kipnis, J., "Multiple Sclerosis as a By-Product of the Failure to Sustain Protective Autoimmunity: A Paradigm Shift," *The Neuroscientist*, 2002, vol. 8, No. 5, pp. 405-413.

Sege, K., et al., "Role of $\beta_2$-Microglobulin in the Intracellular Processing of HLA Antigens," *Biochemistry*, 1981, vol. 20, pp. 4523-4530.

Sharif, S., et al., "Activation of natural killer T cells by α-galactosylceramide treatment prevents the onset and recurrence of autoimmune Type 1 diabetes," *Nature Medicine*, 2001, vol. 7(9), pp. 1057-1062.

Sharif, S., et al., "Regulation of autoimmune disease by natural killer T cells," *Journal of Mol. Med.*, 2002, vol. 80, pp. 290-300.

Shi, F., et al., "Germ line deletion of the CD1 locus exacerbates diabetes in the NOD mouse," *Proc. Natl. Acad. Sci USA*, 2001, vol. 98, No. 12, pp. 6777-6782.

Shin, S., and Morrison, S. L., "Production of Properties of Chimeric Antibody Molecules," *Methods of Enzymology*, 1989, vol. 178, pp. 459-476.

Shin, S, et al., "Functional and Pharmacokinetic Properties of Antibody-Avidin Fusion Proteins," *The Journal of Immunology*, 1997, vol. 158, pp. 4797-4804.

Sidney, J., et al., "Majority of Peptides Binding HLA-A*0201 With High Affinity Crossreact With Other A2-Supertype Molecules," *Human Immunol.*, 2001, vol. 62, pp. 1200-1216.

Sidney, J., et al., "Practical, biochemical and evolutionary implications of the discovery of HLA class I supermotifs," *Immunol. Today*, 1996, vol. 17, No. 6, pp. 261-266.

Sidobre, S., et al., "The Vα14 NKT Cell TCR Exhibits High-Affinity Binding to a Glycolipid/CD1d Complex," *J. Immunol.*, 2002, vol. 169, pp. 1340-1348.

Sieling, P., et al., "Human Double-Negative T Cells in Systematic Lupus Erythematosus Provide Help for IgG and Are Restricted by CD1c," *J. Immunol.*, 2000, vol. 165, pp. 5338-5344.

Silk, J., et al., "Utilizing the adjuvant properties of CD1d-dependent NK T cells in T cell-mediated immunotherapy," *J. Clin. Invest.*, 2004, vol. 114(12), pp. 1800-1811.

Singh, A. K., et al., "The natural killer T cell ligand α-galactosylceramide prevents a promotes pristine-induced lupus in a mice," *NIH Public Access, Author Manuscript, Eur J. Immunol.*, 2005, vol. 35(4), pp. 1143-1154.

Singh, A. K., et al., "Natural Killer T Cell Activation Protects Mice Against Experimental Autoimmune Encephalomyelitis," *J. Exp. Med.*, 2001, vol. 194, No. 12, pp. 1801-1811.

Smyth, M., et al., "Sequential activation of NKT cells and NK cells provides effective innate immunotherapy of cancer," *The Journal of Experimental Medicine*, 2005, vol. 201, No. 12, pp. 1973-1985.

Smyth, M. J., et al., "Sequential production of interferon-γ by NK1.1+ T cells and natural killer cells is essential for the antimetastatic effect of α-galactosylceramide," *Blood*, 2002, vol. 99, pp. 1259-1266.

Smyth, M., et al., "NKT cells-conductors of tumor immunity?," *Curr Opin Immuno*, 2002, vol.14, pp. 165-171.

Smyth, M., et al., "NKT cells and tumor immunity-a double-edged sword," *Nature Immunology*, 2000, vol. 1(6), pp. 459-460.

Spada, F., et al., "CD1d-restricted Recognition of Synthetic Glycolipid Antigens by Human Natural Killer T Cells," *J. Exp. Med.*, 1998, vol. 188(8), pp. 1529-1534.

Spatz, L., et al., "Light Chain Usage in Anti-double-stranded DNA B Cell Subsets: Role in Cell Fate Determination," *J. Exp. Med.*, 1997, vol. 185(7), pp. 1317-1326.

Springer, T. A. and Strominger, J. L., "Detergent-soluble HLA antigens contain a hydrophilic region at the COOH-terminus and a penultimate hydrophobic region," *Proc. Natl. Acad. Sci. USA*, 1976, vol. 73, No. 7, pp. 2481-2485.

Steller, Michael A., et al., "Cell-mediated Immunological Responses in Cervical and Vaginal Cancer Patients Immunized with a Lipidated Epitope of Human Papillomavirus Type 16 E7," *Clinical Cancer Research*, 1998, vol. 4, 2103-2109.

Stirnemann, K., et al., "Sustained activation and tumor targeting of NKT cells using a CD1d-anti-HER2-scFv fusion protein induce antitumor effects in mice," *J. Clin. Invest.*, 2008, vol. 118, No. 3, pp. 994-1005.

Stober, D., et al., "NKT Cells Provide Help for Dendritic Cell-Dependent Priming of MHC Class I-Restricted CD8+ T Cells In Vivo," *J. Immunol.*, 2003, vol. 170, pp. 2540-2548.

Stronge, V.S., et al., "A closer look at CD1d molecules: new horizons in studying NKT cells," *TREND: In Immunology*, 2007, vol. 28, No. 10, 455-463.

Sumida, T., et al., "Selective Reduction of T Cells Bearing Invariant Vα24JαQ Antigen Receptor in Patients with Systemic Sclerosis," *J. Exp. Med.*, 1995, vol. 182, pp. 1163-1168.

Tahir, S. M. A., et al., "Loss of IFN-γ Production of Invariant NK T Cells in Advanced Cancer," *The Journal of Immunology*, 2001, 167:4046-4050.

Takahashi, T., et al., "707-AP Peptide Recognized by Human Antibody Induces Human Leukocyte Antigen A2-restricted Cytotoxic T Lymphocyte Killing of Melanoma," *Clin. Cancer Res.*, 1997, vol. 3, pp. 1363-1370.

Takahashi, T., et al., "Cytotoxic T lymphocytes that recognize decameric peptide sequences of retinoblastoma binding protein 1 (RBP-1) associated with human breast cancer," *British J. Cancer*, 1999, vol. 81, No. 2, pp. 342-349.

Takeda, K., et al., "Relative contribution of NK and NKT cells to the anti-metastatic activities of IL-12," *Int. Immunol.*, 2000, vol. 12, No. 6, pp. 909-914.

Takeda, K., et al., "The Development of Autoimmunity in C57BL/6 lpr Mice Correlates with the Disappearance of Natural Killer Type 1-positive Cells: Evidence for Their Suppressive Action on Bone Marrow Stem Cell Proliferation, B Cell Immunoglobulin Secretion, and Autoimmune Symptoms," *J. Exp. Med.*, 1993, vol. 177, pp. 155-164.

Taniguchi, M., et al., "The NKT cell system: bridging innate and acquired immunity," *Nature Immunology*, 2003, vol. 4, No. 32, 1164-5.

Tanzarella, S., et al., "Identification of a Promiscuous T-Cell Epitope Encoded by Multiple Members of the MAGE Family," *Cancer Res.*, 1999, vol. 59, pp. 2668-2674.

Taraban, V., et al., "Invariant NKT Cells Promote CD8+ Cytotoxic T Cell Responses by Inducing CD70 Expression on Dendritic Cells," *J. Immunol.*, 2008, vol. 180, pp. 4615-4620.

Timmerman, J. M., et al., "Dendritic Cell Vaccines for Cancer Immunotherapy," *Annu. Rev. Med.*, 1999, vol. 50, pp. 507-529.

Tisch, R., and McDevitt, H.O., "Antigen-specific immunotherapy: Is it a real possibility to combat T-cell-mediated autoimmunity?" *Proc. Natl. Acad. Sci. USA*, 1994, vol. 91, pp. 437-438.

Tomioka, H., "Adjunctive Immunotherapy of Mycobacterial Infections," *Current Pharmaceutical Design*, 2004, vol. 10, pp. 3297-3312.

Tsuji, M., "Glycolipids and phospholipids as natural CD1d-binding NKT cell ligands," *Cell Mol. Life Sci.*, 2006, vol. 63, pp. 1889-1898.

Turkewitz, A. P., et al., "Large-Scale Purification of Murine I-A$^k$ and I-E$^k$ Antigens and Characterization of the Purified Proteins," *Molecular Immunol.*, 1983, vol. 20, No. 11, pp. 1139-1147.

Turner, M. J., et al., "Purification of Papain-solubilized Histocompatibility Antigens from a Cultured Human Lymphoblastoid Line, RPMI 4265*," *J. Biol. Chem.*, 1975, vol. 250, No. 12, pp. 4512-4519.

(56) References Cited

OTHER PUBLICATIONS

Uchimura, A., et al., "Immunostimulatory Activities of Mono- or Diglycosylated α-Galactosylceramides," *Bioorg. Med. Chem.*, 1997, vol. 5(7), pp. 1447-1452.

Uchimura, A., et al., "Immunostimulatory Activities of Monoglycosylated α-D-Pyranosylceramnides," *Bioorg. Med. Chem.*, 1997, vol. 5(12), pp. 2245-2249.

Valmori, D., et al., "Analysis of MAGE-3-specific Cytolytic T Lymphocytes in Human Leukocyte Antigen-A2 Melanoma Patients," *Cancer Res.*, 1997, vol. 57, pp. 735-741.

Valmori, D., et al., "Analysis of the Cytolytic T Lymphocyte Response of Melanoma Patients to the Naturally HLA-A*0201-associated Tyrosinase Peptide 368-376," *Cancer Res.*, 1999, vol. 59, pp. 4050-4055.

Valmori, D., et al., "Diversity of the Fine Specificity Displayed by HLA-A*0201-Restricted CTL Specific for the Immunodominant Melan-A/MART-1 Antigenic Peptide," *J. Immunol.*, 1998, vol. 161, pp. 6956-6962.

Van Der Vliet, H. J. J., et al., "Circulating Vα24+ Vβ11+ NKT Cell Numbers Are Decreased in a Wide Variety of Diseases That Are Characterized by Autoreactive Tissue Damage," *Clin. Immunol.*, 2001, vol. 100, No. 2, pp. 144-148.

Van Kaer, L.V., "NKT cells: T lymphocytes with innate effector functions," *Current Opinion in Immunology*, 2007, vol. 19, pp. 354-364.

Venkataswamy, M., et al., "Incorporation of NKT cell activating glycolipids enhances immunogenicity and vaccine efficacy of *Mycobacterium bovis* BCG," *J. Immunol.*, 2009, vol. 183(3), pp. 1644-1656.

Wang, B., et al., "CD1-restricted NK T Cells Protect Nonobese Diabetic Mice from Developing Diabetes," *J. Exp. Med.*, 2001, vol. 194, No. 3, pp. 313-319.

Wang, R., et al., "Recognition of an antigenic peptide derived from tyrosinase-related protein-2 by CTL in the context of HLA-A31 and -A33," *J Immunol*, 1998, vol. 160, pp. 890-897.

Webb, T., et al., "Molecular Identification of GD3 as a Suppressor of the Innate Immune Response in Ovarian Cancer," *American Association for Cancer Research*, 2012, vol. 72, No. 15, pp. 3744-3752.

Whitman, M. C., et al., "The isolated major histocompatibility complex class I α3 domain binds β2m and CD8αα dimers," *Molecular Immunology*, 2000, vol. 37, pp. 141-149.

Whitmire, J., et al., "Direct Interferon-γ Signaling Dramatically Enhances CD4+ and CD8+ T Cell Memory," *J. Immunol.*, 2007, vol. 179, pp. 1190-1197.

Wilson, M. T., et al., "Immunotherapy with ligands of natural killer T cells," *TRENDS in Molecular Med.*, 2002, vol. 8, No. 5, pp. 225-231.

Wilson, S., et al., "Extreme Th1 bias of invariant Vα24JαQ T cells in type 1 diabetes," *Nature*, 1998, vol. 391, pp. 177-181.

Wizel, B., et al., "HLA-A2 Restricted Cytotoxic T Lymphocyte Responses to Multiple *Plasmodium falciparum* Sporozoite Surface Protein 2 Epitopes in Sporozoite-Immunized Volunteers," *J. Immunol.*, 1995, vol. 155, pp. 766-775.

Wizel, B., et al., "Human Infection with *Trypanosoma cruzi* Induces Parasite Antigen-Specific Cytotoxic T Lymphocyte Responses," *J. Clin. Invest.*, 1998, vol. 102, pp. 1062-1071.

Wu, D., et al., "Cross-presentation of Disialoganglioside GD3 to Natural Killer T Cells," *J. Exp. Med.*, 2003, vol. 198(1), pp. 173-181.

Yamaguchi, Y., et al., "Enhancing Effects of (2S,3S,4R)-1-O-(α-D-galactopyranosyl)-2-(N-Hexacosanoylamino)-1,3,4-Octadecanetriol (KRN7000) on Antigen-Presenting Function of Antigen-Presenting Cells and Antimetastatic Activity of KRN7000-Petreated Aantigen-Presenting Cells," *Oncology Research*, 1996, vol. 8(10/11), pp. 399-407.

Yoshimoto, T., et al, "CD4$^{pos}$, NK1.1$^{pos}$ T Cells Promptly Produce Interleukin 4 in Response to In Vivo Challenge with Anti-CD3," *J. Exp. Med.*, 1994, vol. 179, pp. 1285-1295.

Yoshimoto, T., et al., "Defective IgE production by SJL mice is linked to the absence of CD4+, NK1.1+ T cells that promptly produce interleukin 4," *Proc. Natl. Acad. Sci.*, 1995, vol. 92, pp. 11931-11934.

Yoshimoto, T., et al., "Role of NK1.1+ T Cells in a $T_H2$ Response and in Immunoglobulin E Production," *Science*, 1995, vol. 270(5243), pp. 1845-1847.

Young, D., et al., "Confronting the scientific obstacles to global control of tuberculosis," *J. Clin. Inv.*, 2008, vol. 118(4), pp. 1255-1265.

Yu, K. O. A., et al., "Production and characterization of monoclonal antibodies against complexes of the NKT cell ligand α-galactosylceramide bound to mouse CD1d," *J. Immunological Methods.*, 2007, vol. 323, pp. 11-23.

Yu, K., et al., "Modulation of CD1d-restricted NKT cell responses by using N-acyl variants of α-galactosylceramides," *PNAS*, 2005, vol. 102(9), pp. 3383-3388.

Zarour, H. M., et al., "Melan-A/MART-1$_{51-73}$ represents an immunogenic HLA-DR4-restricted epitope recognized by melanoma-reactive CD4+ T cells," *PNAS*, 2000, vol. 97, No. 1, pp. 400-405.

Zarutskie, J. A., et al., "A Conformational Change in the Human Major Histocompatibility Complex Protein HLA-DR1 Induced by Peptide Binding," *Biochemistry*, 1999, vol. 38, pp. 5878-5887.

Zemon, H., "An artificial solution for adoptive immunotherapy," *TRENDS in Biotechnology*, 2003, vol. 21, No. 10, pp. 418-420.

Zeng, D., et al., "Cutting Edge: A Role for CD1 in the Pathogenesis of Lupus in NZB/NZW Mice," *J. Immunol.*, 2000, vol. 164, pp. 5000-5004.

Zeng, Z.-H., et al., "Crystal Structure of Mouse CD1: An MHC-Like Fold with a Large Hydrophobic Binding Groove," *Science*, 1997, vol. 277, pp. 339-345.

Zhang, H., et al., "Targeting of functional antibody-CD59 fusion proteins to a cell surface," *The Journal of Clinical Investigation*, 1999, vol. 103, No. 1, pp. 55-61.

Zhu, X., et al., "A recombinant single-chain human class II MHC molecule (HLA-DR1) as a covalently linked heterotrimer of α chain, β chain, and antigenic peptide, with immunogenicity in vitro and reduced affinity for bacterial superantigens," *European Journal of Immunology*, 1997, vol. 27, pp. 1933-1941.

Hashimoto, M., et al., "Versatile Synthesis of Phenoxydiazirine-Based Fatty Acid Analogues and Photoreactive Galatosylceramide," *Bioorganic & Medicinal Chemistry Letters*, 2002, pp. 89-91.

Hu, V. W. And Wisnieski, B. J., "Photoreactive labeling of M13 coat protein in model membranes by use of a glycolipid probe," *Proc. Natl. Acad. Sci. USA*, 1979, vol. 76, No. 11, pp. 5460-5464.

Lankalapalli, R. S., et al., "Synthesis and Properties of a Photoactivatable Analogue of Psychosine (β-Galactosylsphingosine)," *ChemMedChem*, 2010, vol. 5, No. 5, pp. 682-686.

Schiefner, A., et al., "Structural Evaluation of Potent NKT Cell Agonists: Implications for Design of Novel Stimulatory Ligands," *J. Mol. Biol.*, 2009, vol. 394, No. 1, pp. 71-82.

Tomatsu, I., et al., "Photoresponsive hydrogels for biomedical applications," *Advanced Drug Delivery Reviews*, 2011, vol. 63, No. 14, pp. 1257-1266.

Zegers, M. M. P., et al., "Use of photoactivatable sphingolipid analogues to monitor lipid transport in mammalian cells," *Biochem. J.*, 1997, vol. 328, pp. 489-498.

Parekh, V., et al., "Quantitative and Qualitative Differences in the In Vivo Response of NKT Cells to Distinct α- and β-Anomeric Glycolipids$^1$", *The Journal of Immunology*, 2004, vol. 173, pp. 3693-3706.

Bendelac, A. & Medzhitov, R., "Adjuvants of Immunity: Harnessing Inmate Immunity to Promote Adaptive Immunity," *J. Exp. Med.*, 2002, vol. 195, No. 5, pp. F19-F23.

Brossay, L., et al., "CD1d-mediated Recognition of an α-Galactosylceramide by Natural Killer T Cells Is Highly Conserved through Mammalian Evolution," *J. Exp. Med.*, 1998, vol. 188, pp. 1521-1528.

Brutkiewicz, R. R. and Sriram, V., "Natural killer T (NKT) cells and their role in antitumore immunity," *Crit. Rev. Oncol. Hematol.*, 2002, vol. 41, pp. 287-298.

Chambers, B. J., et al., "Triggering of Natural Killer Cells by the Costimulatory Molecule CD80 (B7-1)," *Immunity*, 1996, vol. 5, pp. 311-317.

Chen, H., et al., "NK1.1+CD4+ T Cells Lose NK1.1 Expression Upon In Vitro Activation," *J. Immunol.*, 1997, vol. 158, pp. 5112-5119.

(56) References Cited

OTHER PUBLICATIONS

Dunbar, et al., "Direct isolation, phenotyping and cloning of low-frequency antigen-specific cytotoxic T lymphocytes from peripheral blood," *Curr Biol*, 1998, vol. 8, No. 7, pp. 413-416.

Eberl, G., et al., "Tissue-Specific Segregation of CD1d-Dependent and CD1d-Independent NK T Cells," *J. Immunol.*, 1999, vol. 162, pp. 6410-6419.

Gumperz, J. E., et al., "Murine CD1d-Restricted T Cell Recognition of Cellular Lipids," *Immunity*, 2000, vol. 12, pp. 211-221.

Hong, S. And Van Kaer, L., "Immune Privilege: Keeping an Eye on Natural Killer T Cells," *J. Exp. Med.*, 1999, vol. 190, No. 9, pp. 1197-1200.

Ikarashi, Y., et al., "Dendritic Cell Maturation Overrules H-2D-mediated Natural Killer T (NKT) Cell Inhibition: Critical Role for B7 in CD1d-dependent NKT Cell Interferon γ Production," *J. Exp. Med.*, 2001, vol. 194, No. 8, pp. 1179-1186.

Janeway, C.A., et al., "The structure of a typical antibody molecule," *Immunobiology: The Immune System in Health and Disease*, 5th ed., New York: Garland Science, 2011, pp. 1-9.

MacDonald, H., "Development and selection of NKT cells," *Current Opinion in Immunology*, 2002, vol. 14, pp. 250-254.

Matsuda, J. & Kronenberg, M. "Presentation of self and microbial lipids by CD1 molecules," *Current Opinion in Immunology*, 2001, vol. 13, pp. 19-25.

Park, S-H and Bendelac, A., "CD1-restricted T-cell responses and microbial infection," *Nature*, 2000, vol. 406, pp. 788-792.

Seino, K-i., et al., "Requirement for natural killer T (NKT) cells in the induction of allograft tolerance," *Proc. Natl. Acad. Sci. U.S.A.*, 2001, vol. 98, No. 5, pp. 2577-2581.

Shamshiev, A., et al., "Self glycolipids as T-cell autoantigens," *Eur. J. Immunol.*, 1999, vol. 29, pp. 1667-1675.

Sidobre, S. And Kronenberg, M., "CD1 tetramers: a powerful tool for the analysis of glycolipid-reactive T cells," *Journal of Immunological Methods*, 2002, vol. 268, pp. 107-121.

Sonoda, K-H, et al., "CD1-reactive Natural Killer T Cells Are Required for Development of Systemic Tolerance through an Immune-Privileged Site," *J. Exp. Med.*, 1999, vol. 190, No. 9, pp. 1215-1225.

Sullivan, B.A. And Kronenberg, M., "Activation or anergy: NKT cells are stunned by α-galactosylceramide," *J. Clin. Invest.*, 2005, vol. 115, pp. 2328-2329.

Uldrich, A.P., et al., "NKT Cell Stimulation with Glycolipid Antigen In Vivo: Costimulation-Dependent Expansion, Bim-Dependent Contraction, and Hyporesponsiveness to Further Antigenic Challenge," *J. Immunol.*, 2005, vol. 175, pp. 3092-3101.

Vincent, M. S., et al., "CD1-dependent dendritic cell instruction," *Nature Immunol.*, 2002, vol. 3, No. 12, pp. 1163-1168.

Wheeler, C.J., et al., "A novel cationic lipid greatly enhances plasmid DNA delivery and expression in mouse lung," *Proc. Natl. Acad. Sci. U.S.A.*, 1996, vol. 93, pp. 11454-11459.

Wilson, S. & Delovitch, T., "Janus-like role of regulatory iNKT cells in autoimmune disease and tumour immunity," *Nature Reviews Immunology*, 2003, vol. 3, pp. 211-222.

Zeng, D., et al., "Bone Marrow $NK1.1^-$ and $NK1.1^+$ T Cells Reciprocally Regulate Acute Graft versus Host Disease," *J. Exp. Med.*, 1999, vol. 189, No. 7, pp. 1073-1081.

Zuidam, N.J., et al., "Electrostatic parameters of cationic liposomes commonly used for delivery as determined by 4-heptadecyl-7-hydroxycoumarin," *Biochim Biophys Acta*, 1997, vol. 1329, No. 2, pp. 211-222.

\* cited by examiner

MODIFIED GLYCOLIPIDS AND METHODS OF MAKING AND USING THE SAME

CROSS-REFERENCE TO RELATED APPLICATIONS

This application claims priority to U.S. Provisional Application No. 61/762,591, filed on Feb. 8, 2013, which is hereby incorporated by reference in its entirety.

STATEMENT AS TO FEDERALLY-SPONSORED RESEARCH

This research was funded in part by National Institutes of Health/National Institute of Allergy and Infectious Diseases grant 5RO1AI45889. Accordingly, the United States Government has certain interest and rights to this invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 430971SEQLIST.TXT, created on Mar. 14, 2013, and having a size of 4.06 kilobytes and is filed concurrently with the specification. The sequence listing contained in this ASCII formatted document is part of the specification and is herein incorporated by reference in its entirety.

FIELD OF THE INVENTION

The invention generally relates to the field of immunology. In particular, the invention involves the modification of glycolipids that are useful in modulating an immune response.

BACKGROUND OF THE INVENTION

Natural killer T (NKT) cells represent a subset of T lymphocytes expressing both T-cell receptor and NK-cell receptor, and play a role in bridging innate immunity to adaptive immunity. Kronenberg M and Gapin L, *Nat Rev Immunol* 2: 557-568 (2002). Upon activation, NKT cells can have a pronounced impact on early and delayed immunity to various pathogens, including *L. monocytogenes*, *M. tuberculosis* and *Leishmania major*. Kronenberg (2002); Behar S M and Porcelli S A, *Curr Top Microbiol Immunol* 314: 215-250 (2007); Emoto M et al., *Eur J Immunol* 29: 650-659 (1999); Ishikawa H et al., *Int Immunol* 12: 1267-1274 (2000); and Ranson T et al., *J Immunol* 175: 1137-1144 (2005). NKT cell activation has been reported to lead to enhanced CD4 and CD8 T cell responses, and to induce dendritic cell (DC) maturation. Nishimura T et al., *Int Immunol* 12: 987-994 (2000) and Silk J D et al., *J Clin Invest* 114: 1800-1811 (2004).

Unlike conventional T cells that recognize MHC-bound peptides, NKT cells are specific for lipid antigens presented by the MHC class I-like protein CD1d. Several glycolipid antigens, including self-derived and bacterial-derived glycolipids, which can be presented by CD1d to activate NKT cells, have been identified to date. Tsuji M *Cell Mol Life Sci* 63: 1889-1898 (2006). NKT cells that have T-cell receptors with invariant Vα14-Jα18 rearrangements (iNKT cells) possess reactivity to a glycosphingolipid, α-galactosylceramide (αGalCer), when presented by CD1d. Kronenberg M and Gapin L, *Nat Rev Immunol* 2: 557-568 (2002); Kronenberg M, *Annu Rev Immunol* 23: 877-900 (2005). Recent studies have shown that vaccines against Plasmodia, *Leishmania donovanii*, *Listeria monocytogenes* and HIV could be improved by activating iNKT cells through co-administration of αGalCer as an adjuvant. Gonzalez-Aseguinolaza G et al., *J Exp Med* 195: 617-624 (2002); Dondji B et al., *European Journal of Immunology* 38: 706-719 (2008); Huang Y X et al., *Vaccine* 26: 1807-1816 (2008); and Enomoto N et al., *FEMS Immunol Med Microbiol* 51: 350-362 (2007).

As a therapeutic, αGalCer has been shown to reduce malarial parasite load in mice and prolong the survival of *M. tuberculosis* infected mice. Gonzalez-Aseguinolaza G et al., *Proc Natl Acad Sci USA* 97: 8461-8466 (2000); Chackerian A et al., *Infection and Immunity* 70: 6302-6309 (2002). A single injection of αGalCer in mice induces secretion of IFNγ, IL-12 and IL-4 in serum. Fujii S et al., *Immunol Rev* 220: 183-198 (2007). Stimulation of CD1d-restricted iNKT cells by αGalCer also leads to a rapid cascade of activation of immune and inflammatory cells including NK cells, dendritic cells, B cells, and conventional T cells. Nishimura T et al., *Int Immunol* 12: 987-994 (2000); Kitamura H et al., *J Exp Med* 189: 1121-1128 (1999); Fujii S et al., *J Exp Med* 198: 267-279 (2003). iNKT cells produce large amounts of IL-4 and IFNγ and the production requires direct contact between iNKT cells and DCs through CD40-CD40 ligand interactions. Nishimura T et al., *Int Immunol* 12: 987-994 (2000). IFNγ produced by iNKT cells has been shown to have a critical role in the antimetastatic effect of αGalCer in murine tumor models. Hayakawa Y et al., *Eur J Immunol* 31: 1720-1727 (2001); Smyth M J et al., *Blood* 99: 1259-1266 (2002). Thus, activation of iNKT cells may play a role in modulating adaptive immune responses by influencing the early cytokine environment, thereby enhancing host resistance to infectious and inflammatory diseases.

Soluble CD1d proteins loaded with glycolipids such as α-galactosylceramides are being developed as immunotherapeutic agents. However, their utility is limited by the instability of the noncovalent interaction between the glycolipid and the protein, which allows them to rapidly dissociate or be displaced by natural competitive inhibitors and lose activity in vivo. Webb T J et al. *Cancer Res* 72: 3744-3752 (2012). There remains a need to develop a method for covalently linking the glycolipid to the CD1d protein to create stable and long-lived complexes that maintain potent NKT-cell activating properties.

SUMMARY OF THE INVENTION

The present invention is directed to modified glycolipids comprising a functional group that allows for a stable covalent linkage to a protein, such as CD1d, complexes, cells, and vaccines comprising the same, and methods for producing and using the same. Modified glycolipid/protein complexes comprise a modified glycolipid physically associated with a protein (e.g., CD1d). In some embodiments, the modified glycolipids comprise a benzophenone group. Thus, in some embodiments, the modified glycolipid/protein complexes comprise a glycolipid covalently bound to a protein (e.g., CD1d) via a benzophenone linkage. Modified glycolipids find use in serving as a means for covalently binding glycolipids to other molecules, such as proteins. Modified ceramide-like glycolipid/CD1d complexes find use in methods for enhancing or eliciting an immune response, methods for enhancing the activity of Natural Killer T cells, and methods for treating or preventing a disease.

The following embodiments are encompassed by the present invention.

1. A modified glycolipid comprising a photoreactive group.

2. The modified glycolipid of embodiment 1, wherein said photoreactive group is covalently bound to a lipophilic moiety of said glycolipid.

3. The modified glycolipid of embodiment 1, wherein said photoreactive group is covalently bound to a lipophilic acyl chain of said glycolipid.

4. The modified glycolipid of embodiment 3, wherein said photoreactive group is covalently bound to the terminus of the acyl chain of said glycolipid.

5. The modified glycolipid of embodiment 4, wherein said acyl chain is a linear acyl chain.

6. The modified glycolipid of embodiment 5, wherein said linear acyl chain has at least 11 atoms, excluding hydrogens.

7. The modified glycolipid of embodiment 5, wherein said linear acyl chain has about 11 to about 14 atoms, excluding hydrogens.

8. The modified glycolipid of embodiment 5, wherein said acyl chain is selected from the group consisting of:

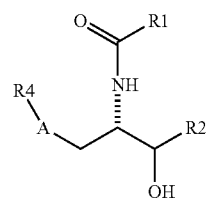

(Formula I)

wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or

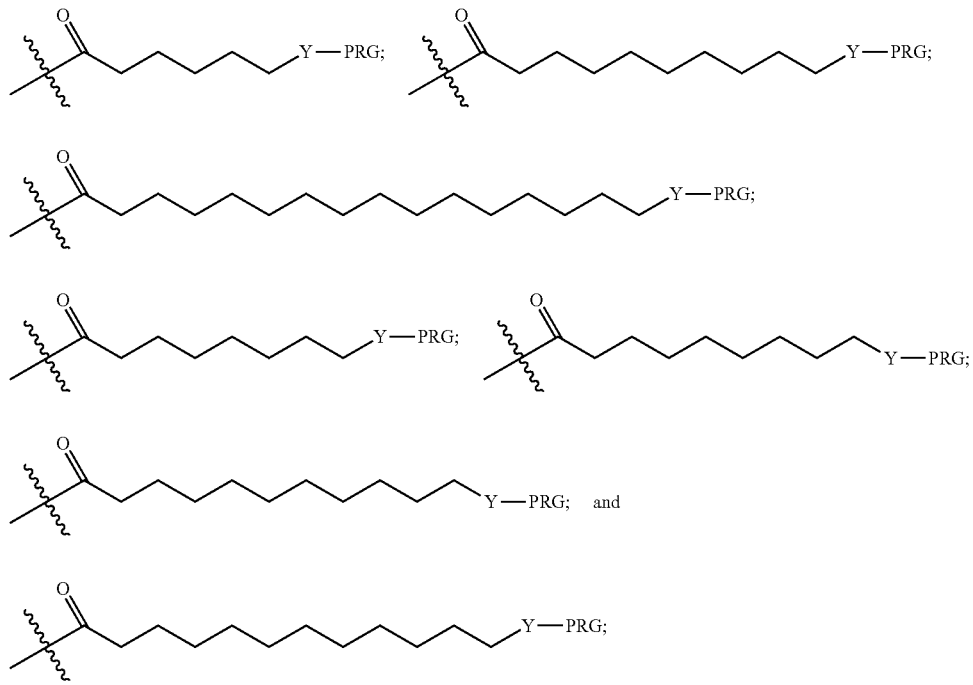

wherein Y if present is —O—, —CH$_2$—, —S—, —OCH$_2$—, —SCH$_2$—, —CH$_2$CH$_2$—; or a bond, and PRG is a photoreactive group.

9. The modified glycolipid of any one of embodiments 1-8, wherein said photoreactive group is a benzophenone group.

10. The modified glycolipid of any one of embodiments 1-9, wherein said glycolipid comprises a ceramide-like glycolipid, and wherein said photoreactive group is covalently bound to the N-acyl lipophilic moiety of said ceramide-like glycolipid.

11. The modified glycolipid of embodiment 10, wherein said ceramide-like glycolipid comprises a glycosylceramide or an analog thereof.

12. The modified glycolipid of embodiment 11, wherein said glycosylceramide or analog thereof comprises Formula I:

alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):

(a) —CH$_2$(CH$_2$)$_x$CH$_3$, (b) —CH(OH)(CH$_2$)$_x$CH$_3$, (c) —CH(OH)(CH$_2$)$_x$CH(CH$_3$)$_2$, (d) —CH=CH(CH$_2$)$_x$CH$_3$, (e) —CH(OH)(CH$_2$)$_x$CH(CH$_3$)CH$_2$CH$_3$, wherein X is an integer ranging from 4-17;

R4 is an α-linked or a β-linked monosaccharide, or when R1 is a linear or branched $C_1$-$C_{27}$ alkane, R4 is:

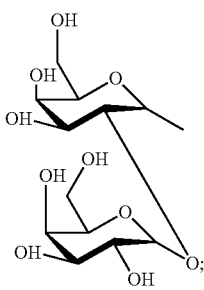

and

A is O or —CH$_2$.

13. The modified glycolipid of embodiment 12, wherein R1 is —(CH$_2$)$_{22}$CH$_3$ or —(CH$_2$)$_{24}$—CH$_3$.

14. The modified glycolipid of embodiment 12 or 13, wherein R2 is —CH(OH)—(CH$_2$)$_{13}$CH$_3$.

15. The modified glycolipid of any one of embodiments 12-14, wherein R4 is galactosyl, mannosyl, fucosyl or glucosyl.

16. The modified glycolipid of embodiment 10, wherein said ceramide-like glycolipid comprises an α-galactosylceramide or an analog thereof.

17. The modified glycolipid of embodiment 16, wherein said α-galactosylceramide or analog thereof comprises Formula II:

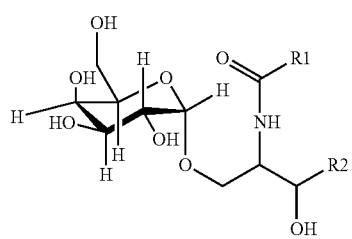

(Formula II)

wherein
R1 is a linear or branched C$_1$-C$_{27}$ alkane or C$_2$-C$_{27}$ alkene; or R1 is —C(OH)—R3 wherein R3 is linear or branched C$_1$-C$_{26}$ alkane or C$_2$-C$_{26}$ alkene; and
R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 4-17.

18. The modified glycolipid of embodiment 17, wherein R2 is —CH(OH)(CH$_2$)$_x$CH$_3$, wherein X is an integer ranging from 4-13.

19. The modified glycolipid of embodiment 18, wherein R2 is —CH(OH)—(CH$_2$)$_{13}$CH$_3$.

20. The modified glycolipid of any one of embodiments 17-19, wherein R1 is selected from the group consisting of (CH$_2$)$_9$CH=CH—CH$_2$—CH=CH(CH$_2$)$_4$CH$_3$, (CH$_2$)$_8$CH=CH—CH$_2$—CH=CH(CH$_2$)$_4$CH$_3$, (CH$_2$)$_7$CH=CH—CH$_2$—CH=CH(CH$_2$)$_4$CH$_3$, (CH$_2$)$_3$CH=CH—CH$_2$—CH=CH—CH$_2$—CH=CH—(CH$_2$)$_4$CH$_3$, (CH$_2$)$_3$CH=CH—CH$_2$—CH=CH—CH$_2$—CH=CH—CH$_2$—CH=CH—CH$_2$CH$_3$, (CH$_2$)$_7$CH=CH—CH$_2$—CH=CH=(CH$_2$)$_4$CH$_3$, (CH$_2$)$_7$CH=CH—CH=CH(CH$_2$)$_5$CH$_3$, (CH$_2$)$_8$CH=CH—CH= CH(CH$_2$)$_4$CH$_3$, (CH$_2$)$_9$CH=CH—CH=CH(CH$_2$)$_5$CH$_3$, (CH$_2$)$_6$CH=CH—CH=CH—CH=CH(CH$_2$)$_4$CH$_3$, (CH$_2$)$_6$CH=CH—CH=CH—CH=CH(CH$_2$)$_4$CH$_3$ and (CH$_2$)$_7$CH=CH—CH=CH—CH=CH(CH$_2$)$_3$CH$_3$.

21. The modified glycolipid of embodiment 20, wherein the double bonds are cis or trans.

22. The modified glycolipid of embodiment 16, wherein said α-galactosylceramide or analog thereof comprises Formula III:

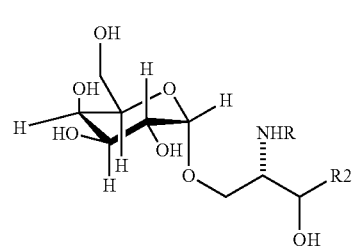

(Formula III)

wherein R is —C(O)R1, wherein R1 is a linear or branched C$_1$-C$_{27}$ alkane or C$_2$-C$_{27}$ alkene; or R1 is —C(OH)—R3 wherein R3 is a linear or branched C$_1$-C$_{26}$ alkane or C$_2$-C$_{26}$ alkene; or R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring; or R1 is an optionally substituted aromatic ring, or an aralkyl, and R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 4-17.

23. The modified glycolipid of embodiment 22, wherein R1 is substituted with oxo; hydroxy; halogen; phenyl; —OC(O)R6; —OR6; —C(O)R6; or N(R6)$_2$, wherein each R6 is independently a C$_1$-C$_6$ substituted alkyl, or a substituted aromatic ring optionally substituted with halogen; hydroxy; —OC(O)R7; —OR7; —C(O)R7 or N(R7)$_2$, and wherein each R7 is a substituted C$_1$-C$_6$ alkyl.

24. The modified glycolipid of embodiment 22, wherein R1 is selected from the group consisting of

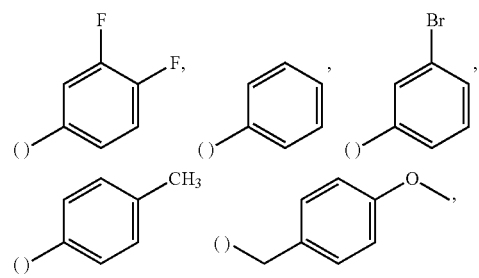

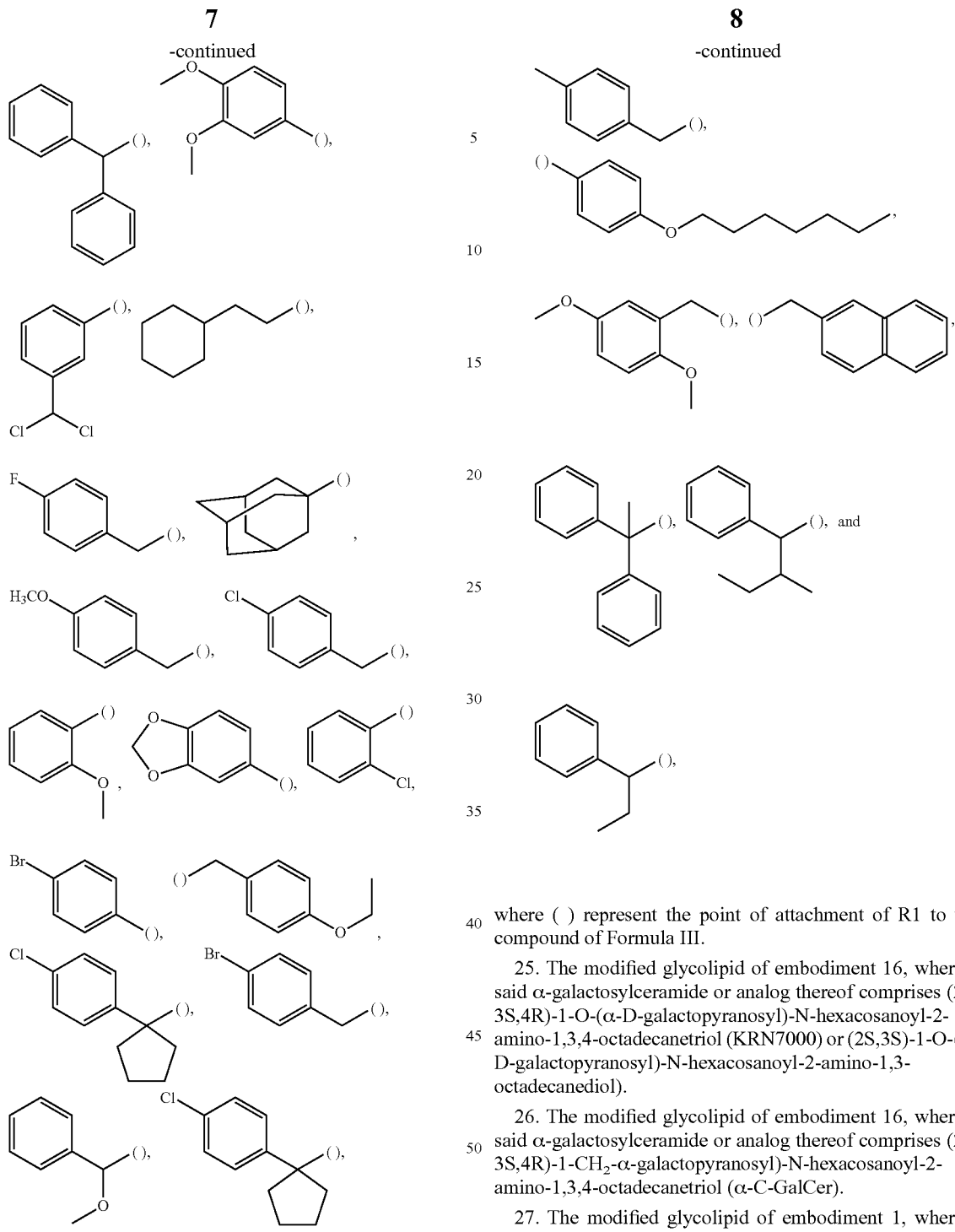

where ( ) represent the point of attachment of R1 to the compound of Formula III.

25. The modified glycolipid of embodiment 16, wherein said α-galactosylceramide or analog thereof comprises (2S,3S,4R)-1-O-(α-D-galactopyranosyl)-N-hexacosanoyl-2-amino-1,3,4-octadecanetriol (KRN7000) or (2S,3S)-1-O-(α-D-galactopyranosyl)-N-hexacosanoyl-2-amino-1,3-octadecanediol).

26. The modified glycolipid of embodiment 16, wherein said α-galactosylceramide or analog thereof comprises (2S,3S,4R)-1-CH$_2$-α-galactopyranosyl)-N-hexacosanoyl-2-amino-1,3,4-octadecanetriol (α-C-GalCer).

27. The modified glycolipid of embodiment 1, wherein said modified glycolipid has the structure:

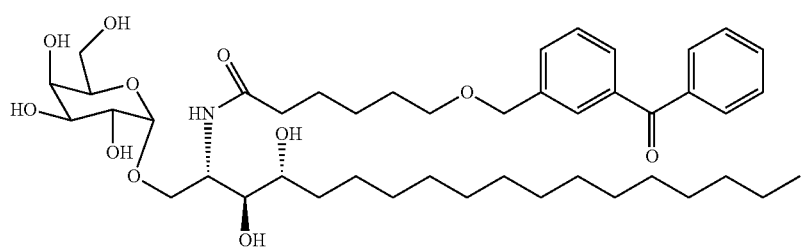 [SMILES: CCCCCCCCCCCCCC[C@@H](O)[C@@H](O)[C@H](COC1OC(CO)C(O)C(O)C1O)NC(=O)CCCCCOCc1cccc(C(=O)c2ccccc2)c1]

28. The modified glycolipid of embodiment 1, wherein said modified glycolipid has the structure:

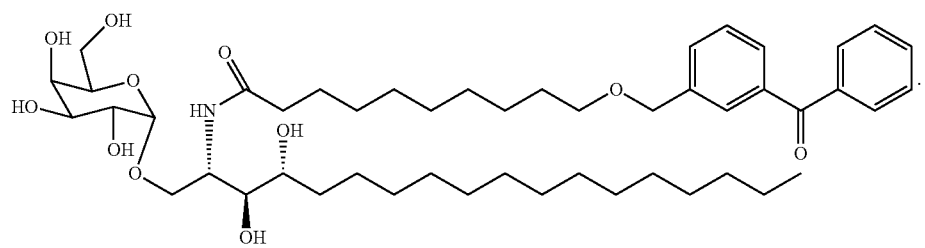 [SMILES: CCCCCCCCCCCCCC[C@@H](O)[C@@H](O)[C@H](COC1OC(CO)C(O)C(O)C1O)NC(=O)CCCCCCCCCOCc1cccc(C(=O)c2ccccc2)c1]

29. The modified glycolipid of embodiment 1, wherein said modified glycolipid has the structure:

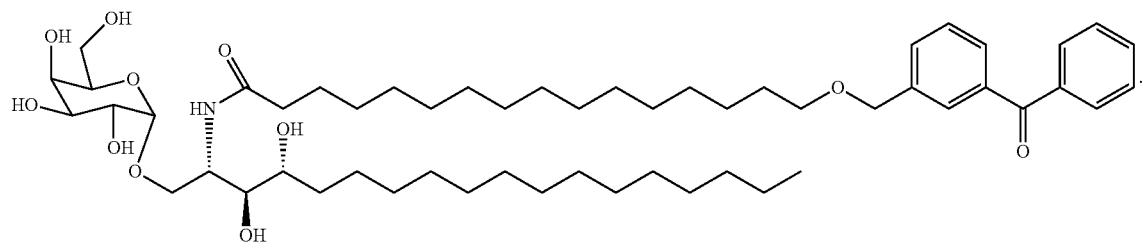 [SMILES: CCCCCCCCCCCCCC[C@@H](O)[C@@H](O)[C@H](COC1OC(CO)C(O)C(O)C1O)NC(=O)CCCCCCCCCCCCCCCOCc1cccc(C(=O)c2ccccc2)c1]

30. The modified glycolipid of embodiment 1, wherein said modified glycolipid has the structure:

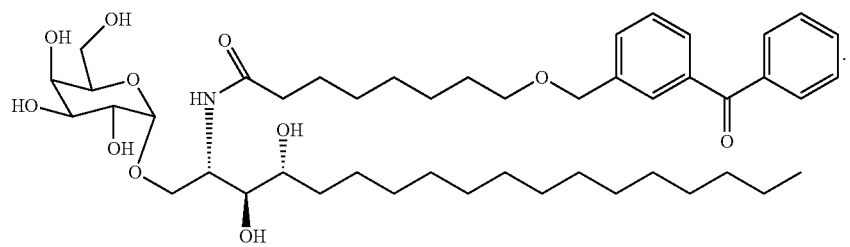 [SMILES: CCCCCCCCCCCCCC[C@@H](O)[C@@H](O)[C@H](COC1OC(CO)C(O)C(O)C1O)NC(=O)CCCCCCCOCc1cccc(C(=O)c2ccccc2)c1]

31. The modified glycolipid of embodiment 1, wherein said modified glycolipid has the structure:

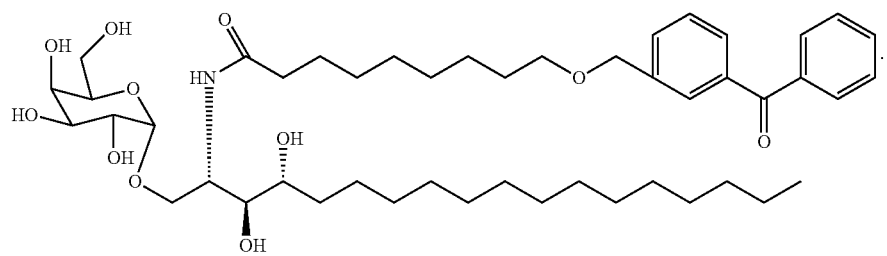 [SMILES: CCCCCCCCCCCCCC[C@@H](O)[C@@H](O)[C@H](COC1OC(CO)C(O)C(O)C1O)NC(=O)CCCCCCCCOCc1cccc(C(=O)c2ccccc2)c1]

32. The modified glycolipid of embodiment 1, wherein said modified glycolipid has the structure:

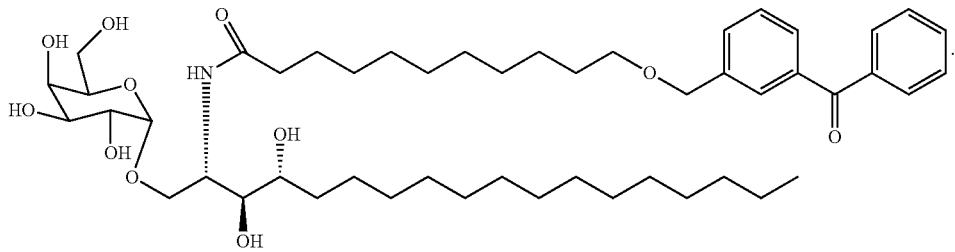 [SMILES: CCCCCCCCCCCCCC[C@@H](O)[C@@H](O)[C@H](COC1OC(CO)C(O)C(O)C1O)NC(=O)CCCCCCCCCCOCc1cccc(C(=O)c2ccccc2)c1]

33. The modified glycolipid of embodiment 1, wherein said modified glycolipid has the structure:

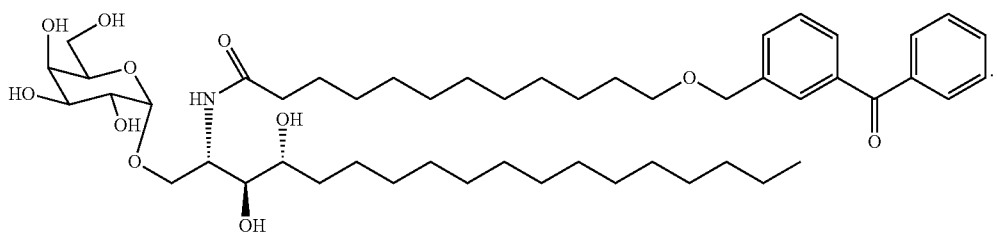 [SMILES: CCCCCCCCCCCCCC[C@@H](O)[C@@H](O)[C@H](COC1OC(CO)C(O)C(O)C1O)NC(=O)CCCCCCCCCCCOCc1cccc(C(=O)c2ccccc2)c1]

34. A modified glycolipid/protein complex comprising: a protein and the modified glycolipid of any one of embodiments 1-33, wherein said modified glycolipid is physically associated with said protein.

35. The modified glycolipid/protein complex of embodiment 34, wherein said modified glycolipid is covalently linked to the protein.

36. The modified glycolipid/protein complex of embodiment 34 or 35, wherein said protein is CD1d.

37. The modified glycolipid/protein complex of embodiment 36, wherein said CD1d has an amino acid sequence selected from the group consisting of:
   a) an amino acid sequence at least 90% identical to amino acids 21 to 295 of SEQ ID NO:1.
   b) the amino acid sequence set forth as amino acids 21 to 295 of SEQ ID NO:1;
   c) an amino acid sequence identical to amino acids 21 to 295 of SEQ ID NO:1, except for at least one but less than 10 conservative amino acid substitutions;
   d) the amino acid sequence set forth as amino acids 1 to 295 of SEQ ID NO:1;
   e) an amino acid sequence at least 90% identical to amino acids 1 to 295 of SEQ ID NO:1;
   f) an amino acid sequence identical to amino acids 21 to 295 of SEQ ID NO:1, except for at least one but less than 10 conservative amino acid substitutions;
   g) the amino acid sequence set forth in SEQ ID NO: 1;
   h) an amino acid sequence at least 90% identical to SEQ ID NO:1; and
   i) an amino acid sequence identical to SEQ ID NO:1, except for at least one but less than 10 conservative amino acid substitutions.

38. The modified glycolipid/protein complex of embodiment 36 or 37, further comprising a β2-microglobulin physically associated with said CD1d.

39. The modified glycolipid/protein complex of embodiment 38, wherein said β2-microglobulin has an amino acid sequence selected from the group consisting of:
   a) an amino acid sequence at least 90% identical to amino acids 21 to 113 of SEQ ID NO:2.
   b) the amino acid sequence set forth as amino acids 21 to 113 of SEQ ID NO:2;
   c) an amino acid sequence identical to amino acids 21 to 113 of SEQ ID NO:2, except for at least one but less than 10 conservative amino acid substitutions;
   d) the amino acid sequence set forth in SEQ ID NO:2;
   e) an amino acid sequence at least 90% identical to SEQ ID NO:2; and
   f) an amino acid sequence identical to SEQ ID NO:2, except for at least one but less than 10 conservative amino acid substitutions.

40. The modified glycolipid/protein complex of any one of embodiments 36-39, wherein said modified glycolipid/protein complex enhances the activity of Natural Killer T (NKT) cells.

41. The modified glycolipid/protein complex of any one of embodiments 36-40, wherein said modified glycolipid/protein complex further comprises an antibody or fragment thereof specific for a target antigen, and wherein said antibody or antigen-binding fragment thereof is linked to said CD1d.

42. The modified glycolipid/protein complex of embodiment 41, wherein said antigen-binding fragment is selected from the group consisting of a F(ab) fragment, a F(ab')2 fragment, and a single-chain antibody.

43. The modified glycolipid/protein complex of embodiment 41 or 42, wherein said target antigen is a cell surface marker of tumor cells.

44. The modified glycolipid/protein complex of embodiment 43, wherein said cell surface marker is selected from the group consisting of CEA, Her2/neu, EGFR type I or type 11, CD19, CD20, CD22, Muc-1, PSMA, or STEAP.

45. The modified glycolipid/protein complex of embodiment 44, wherein said cell surface marker is CEA.

46. The modified glycolipid/protein complex of any one of embodiments 41-45, wherein said CD1d is attached to the heavy chain of said antibody or heavy chain fragment of said antigen-binding antibody fragment.

47. The modified glycolipid/protein complex of any one of embodiments 41-45, wherein said CD1d is attached to the light chain of said antibody or light chain fragment of said antigen-binding antibody fragment.

48. The modified glycolipid/protein complex of any one of embodiments 37-47, further comprising an antigen.

49. The modified glycolipid/protein complex of embodiment 48, wherein said antigen is an immunogenic polypeptide of a virus or a cell selected from the group consisting of a virus, bacterium, fungus, and tumor cell.

50. A composition comprising the modified glycolipid/antibody complex of any one of embodiment 36-47, and a pharmaceutical carrier.

51. The composition of embodiment 50, wherein said pharmaceutical carrier is selected from the group consisting of saline, buffered saline, dextrose, water, glycerol, and combinations thereof.

52. A method of treating or preventing a disease in a subject, comprising administering to a subject in need of said treatment or prevention the modified glycolipid/protein complex of any one of embodiments 36-49 or the composition of embodiment 50 or 51, wherein said modified glycolipid/protein complex is administered in an amount sufficient to alter the progression of said disease.

53. The method of embodiment 52, wherein an immune response is enhanced or modified relative to an immune response produced by the protein not covalently linked to the glycolipid.

54. The method of embodiment 52, wherein said disease is selected from the group consisting of a viral disease, a bacterial disease, a fungal disease, a parasitic disease, a proliferative disease, an autoimmune disease, and an inflammatory disease.

55. The method of embodiment 52, wherein said disease is selected from the group consisting of tuberculosis, pulmonary disease resembling tuberculosis, lymphadenitis, skin disease, disseminated disease, bubonic plague, pneumonic plague, tularemia, Legionairre's disease, anthrax, typhoid fever, paratyphoid fever, foodborne illness, listeriosis, malaria, HIV, SIV, HPV, RSV, influenza, hepatitis (HAV, HBV, and HCV), multiple sclerosis, diabetes, Sjogren's Syndrome, and cancer.

56. A method of inducing an immune response against an antigen in a subject, comprising administering to said subject the modified glycolipid/protein complex of any one of embodiments 36-49 or the composition of embodiment 50 or 51.

57. The method of embodiment 56, wherein said modified glycolipid/protein complex comprises said antigen.

58. The method of embodiment 57, wherein said antigen is covalently bound to said protein.

59. The method of any one of embodiments 56-58, wherein said modified glycolipid/protein complex is administered in an amount sufficient to enhance the activity of Natural Killer T (NKT) cells in said subject.

60. The method of any one of embodiments 53-59, wherein said immune response comprises an antibody response.

61. A method for enhancing an immune response in a subject to a heterologous antigen, wherein said method comprises administering to said subject said heterologous antigen and the modified glycolipid/protein complex of any one of embodiments 36 to 49 or the composition of embodiment 50 or 51 simultaneously, prior to, or subsequent to the administration of said heterologous antigen.

62. The method of any one of embodiments 52-61, wherein said subject is an animal.

63. The method of embodiment 62, wherein said animal is a human.

64. A method for synthesizing a modified glycolipid of Formula (VI) comprising a benzophenone group, said method comprising the steps of:

activating a carboxylic acid derivative of Formula (IV) to form an activated acyl derivative

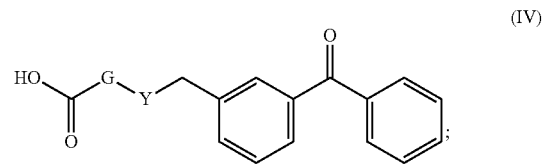

and coupling the activated acyl derivative with a ceramide-like glycolipid of Formula (V)

thereby forming the modified glycolipid comprising a benzophenone group of Formula (VI)

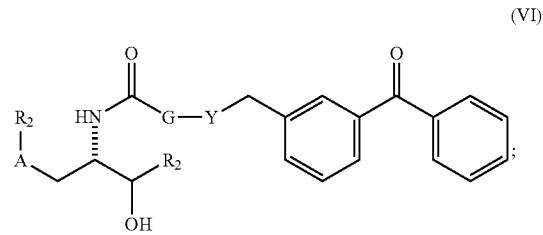

wherein

G is a linear or branched $C_1$-$C_{27}$ alkane or $C_2$-$C_{27}$ alkene; or G is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is an optionally substituted aromatic ring, or an aralkyl;

$R_4$ is a substituted or unsubstituted sugar or analogs thereof;

A if present is —O—, —$CH_2$—; or is a single bond,

Y is —O—, —$CH_2$— or —S—, and $R_2$ is a substituted or an unsubstituted C3-C40 alkyl, alkenyl or alkynyl chain.

65. The method according to embodiment 64, wherein $R_2$ of the modified glycolipid comprising a benzophenone group of Formula (VI) is one of the following (a)-(e):

(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH═CH(CH$_2$)$_x$CH$_3$,
(e) —CH(OH)(CH$_2$)$_x$CH(CH$_3$)CH$_2$CH$_3$, wherein x is an integer ranging from 0-40.

66. The method according embodiment 65, wherein R2 of the modified glycolipid comprising a benzophenone group of Formula (VI) is:
—CH(OH)(CH$_2$)$_x$CH$_3$, wherein x is an integer ranging from 4-17.

67. The method according to embodiment 66, wherein R2 of the modified glycolipid comprising a benzophenone group of Formula (VI) is:
—CH(OH)(CH$_2$)$_{13}$CH$_3$.

68. The method according to any of the embodiments 64-67, wherein G is: —(CH$_2$)n-, wherein n is an integer ranging from 0-20 and Y is O.

69. The method according to any of the embodiments 64-68, wherein:
G is —(CH$_2$)n-, wherein n is an integer ranging from 0-20 and Y is O;
R2-CH(OH)(CH$_2$)$_x$CH$_3$, wherein x is an integer ranging from 4-17;
A is O;
Y is O;
R4 is an α-galactosyl.

70. The method according to embodiment 68, further comprising the steps of synthesis of the carboxylic acid derivative of Formula (IV) wherein Y is O, comprising:
reacting a benzophenone derivative (A)

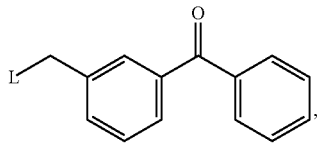

with an alkyl diol derivative (B)

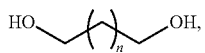

wherein L is a leaving group and n is an integer ranging from 0-20, thereby forming the hydroxyl derivative (C)

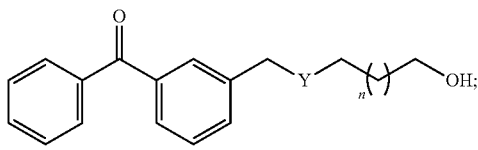

and
oxidizing the hydroxyl derivative to the carboxylic acid derivative of Formula (IV) wherein Y is O.

71. The method according to embodiment 68, further comprising the steps of synthesis of the carboxylic acid derivative of Formula (IV) wherein Y is O, comprising:

converting a benzophenone derivative (A)

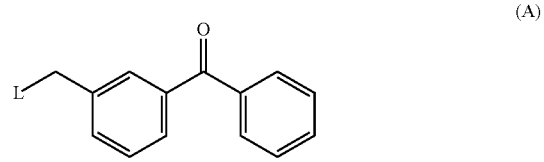

to a hydroxy benzophenone derivative (D)

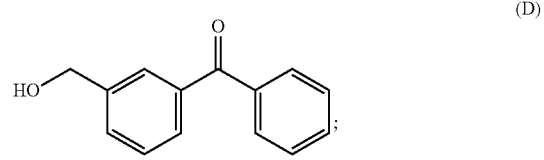 [SMILES: O=C(c1ccccc1)c1cccc(CO)c1]

reacting the hydroxy benzophenone derivative (D) with a carboxylic acid derivative (E)

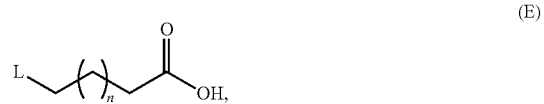

wherein L is a leaving group and n is an integer ranging from 0-20, thereby forming the carboxylic acid derivative of Formula (IV) wherein Y is O.

72. A method for producing a modified glycolipid/protein complex, said method comprising the steps of:
a) contacting the modified glycolipid of any one of embodiments 1-49 or a modified glycolipid produced by the method of any one of embodiments 64-71 with a protein;
b) irradiating said modified glycolipid and said protein with ultraviolet light to produce a modified glycolipid/protein complex.

73. The method of embodiment 72, wherein said protein is CD1d.

74. The method of embodiment 72 or 73, wherein said modified glycolipid and said protein are contacted and irradiated in a solution.

BRIEF DESCRIPTION OF THE FIGURES

FIG. 6A shows samples that had not been irradiated with UV and FIG. 6B shows samples that had been irradiated with UV. ND=not dissociated; D=dissociated FIG. 7A shows samples that had not been irradiated with UV and FIG. 7B shows samples that had been irradiated with UV.

FIG. 8A shows samples that had not been irradiated with UV and FIG. 8B shows samples that had been irradiated with UV. NDiss or NoDiss=not dissociated; Diss=dissociated FIGS. 9A-9B show a direct comparison of DB12-8 and 7DW8-5 complexes with mCD1d.CEA fusion protein by ELISA using mAb L363. FIGS. 9C-9D show the effect of a 10 fold scale-up on UV crosslinking and dissociation of DB12-8:mCD1d.CEA. FIGS. 9A and 9C show samples that had not been irradiated with UV and FIGS. 9B and 9D show samples that had been irradiated with UV. NDiss or NoDiss=not dissociated; Diss=dissociated

DETAILED DESCRIPTION OF THE INVENTION

Figure 1:
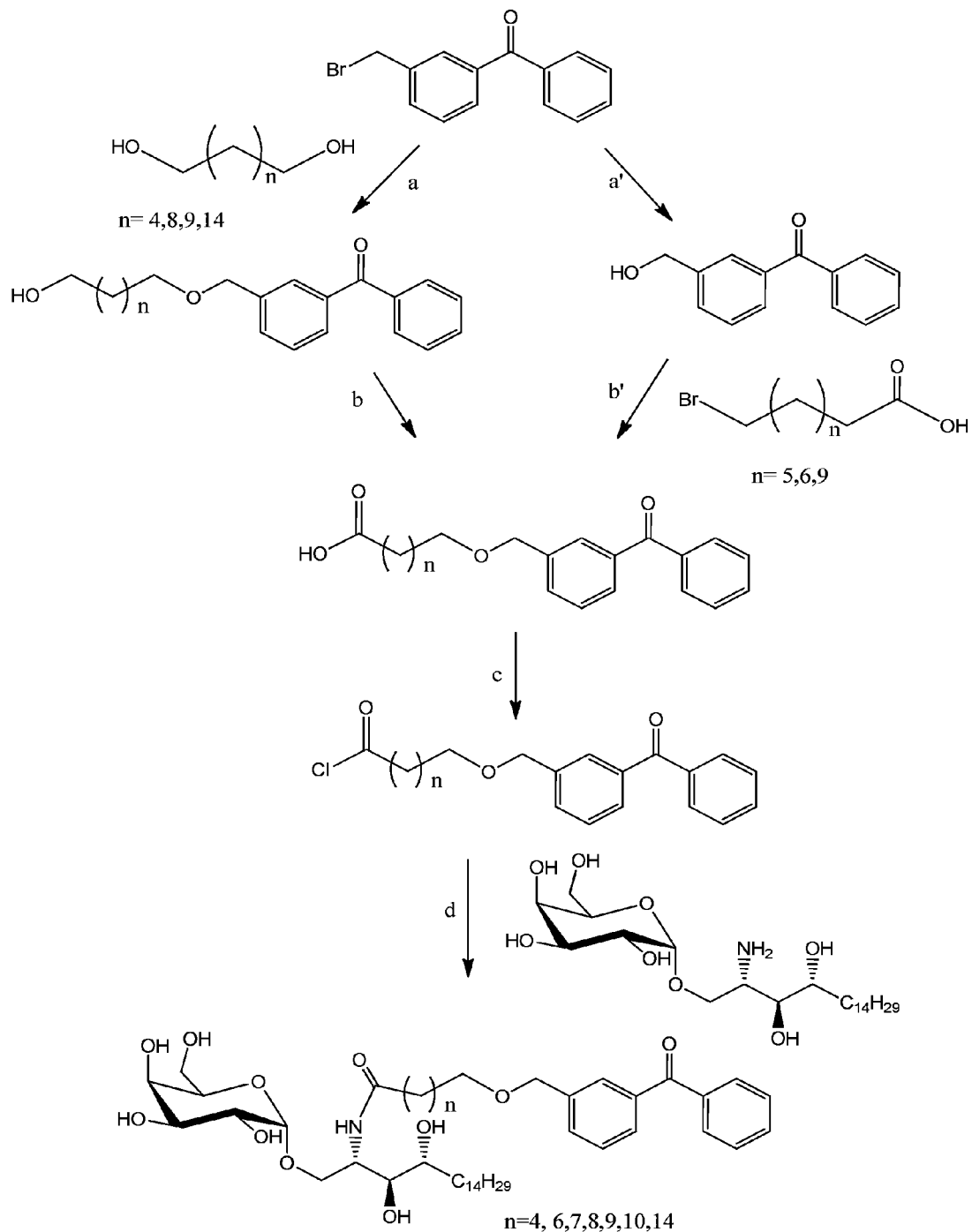
FIG. 1: shows a schematic for the synthesis of αGalCer-benzophenone derivatives.

The present invention provides compositions, isolated cells, vaccines, and methods, which are useful for enhancing, i.e., eliciting, stimulating or increasing, an immune response, e.g., a primary and/or secondary immune response. Described herein are modified glycolipids comprising a functional group, such as benzophenone, that allow for a stable covalent linkage with a protein, such as CD1d. Complexes comprising the modified glycolipids and a physically associated protein (e.g., CD1d) and methods for synthesizing and using the same are also provided herein. In certain embodiments, the modified glycolipid or modified glycolipid/protein complex further enhances an immune response by affecting the activity of CD1d-restricted natural killer T ("NKT") cells. The modified glycolipids and modified glycolipid/protein complexes as described herein are useful for stimulating desirable immune responses, for example, immune responses against mycobacterial antigens, tumors, heterologous antigens, or a targeting molecule. The immune response can be useful for preventing, treating or ameliorating diseases caused by bacterial pathogens; e.g., mycobacteria, e.g., *Mycobacterium tuberculosis*, which causes TB in humans; other infectious agents; or tumors. In some embodiments, employing certain forms of the glycolipid, as described elsewhere, the invention can be employed to redirect an inflammatory or autoimmune response from a predominantly TH1 to a TH2 response. Examples can be found, e.g., in U.S. Patent Appl. Publ. Nos. 2006/0052316 and 2010/0183549; each of which is herein incorporated by reference in its entirety.

The natural immune system strikes a complex balance between highly aggressive, protective immune responses to foreign pathogens and the need to maintain tolerance to normal tissues. In recent years there has been increasing recognition that interactions among many different cell types contribute to maintaining this balance. Such interactions can, for example, result in polarized responses with either production of pro-inflammatory cytokines (e.g., interferon-gamma) by TH1 type T cells or production of interleukin-4 (IL-4) by TH2 type T cells that suppress TH1 activity. In a number of different animal models, T cell polarization to TH1 has been shown to favor protective immunity to tumors or infectious pathogens whereas T cell polarization to TH2 can be a critical factor in preventing development of cell-mediated autoimmune disease. The conditions that determine whether immune stimulation will result in aggressive cell-mediated immunity or in down regulation of such responses are highly localized in the sense that each tissue is comprised of a distinctive set of antigen presenting cells (APC) and lymphocyte lineages that interact to favor different immune responses. For example, under optimal conditions, the dendritic cells (DC) localized in a normal tissue can represent predominantly a lineage and stage of maturation that favors tolerogenic interactions and serves as a barrier to cell-mediated autoimmunity whereas a tumor or site of infection will attract mature myeloid dendritic cells that stimulate potent cell-mediated immune responses.

NKT cells have an unusual ability of secreting both TH1 and TH2 cytokines and potent cytotoxic as well as regulatory functions have been documented in inflammation, autoimmunity and tumor immunity (Bendelac et al., *Science* 268:863 (1995); Chen and Paul, *J Immunol* 159:2240 (1997); and Exley et al., *J Exp Med* 186:109 (1997)). They are also known for their rapid production of large quantities of both IL-4 and IFN-γ upon stimulation through their α-βTCRs (Exley et al., *J. Exp. Med.* 186:109 (1997).

CD1d-restricted NKT cells are a unique class of non-conventional T cells that appear to play an important role in defining the outcome of immune stimulation in the local environment. They share with the larger class of NKT cells the expression of markers of both the T cell and natural killer (NK) cell lineages. As such, NKT cells are considered as part of innate immunity like NK cells and in humans their frequency in normal individuals can be as high as 2.0% of total T lymphocytes (Gumperz et al., *J Exp Med* 195:625 (2002); Lee et al., *J Exp Med* 195:637 (2002)).

CD1d-restricted NKT cells are distinguished from other NKT cells by their specificity for lipid and glycolipid antigens presented by the monomorphic MHC class Ib molecule, CD1d (Kawano et al., *Science* 278:1626-1629 (1997)). CD1d is a non-MHC encoded molecule that associates with β2-microglobulin and is structurally related to classical MHC class I molecules. CD1d has a hydrophobic antigen-binding pocket that is specialized for binding the hydrocarbon chains of lipid tails or hydrophobic peptides. Zeng et al., *Science* 277: 339-345, (1997). CD1d is known to bind a marine sponge derived α-glycosylated sphingolipid, α-galactosylceramide (α-GalCer), and related molecules such as ceramide-like glycolipid antigens with α-linked galactose or glucose but not mannose. Kawano et al., *Science* 278:1626-1629 (1997); and Zeng et al., *Science* 277: 339-345 (1997). As discussed herein, the ability to activate CD1d-restricted NKT cells by stimulation with α-GalCer or related molecules bound to CD1d of antigen presenting cells has greatly facilitated functional analysis of this non-conventional T cell subset. In the absence of inflammation, CD1d-restricted NKT cells have been shown to localize preferentially in certain tissues like thymus, liver and bone marrow (Wilson et al., *Trends Mol Med* 8:225 (2002)) and antitumor activity of NKT cells has been investigated in, for example, mouse liver metastasis.

Among the CD1d-restricted NKT cells is a subset, referred to herein as "iNKT cells," that express a highly conserved αβT cell receptor (TCR). In humans this invariant TCR is comprised of Vα24Jα15 in association with Vβ11 whereas in mice the receptor comprises the highly homologous Vα14Jα18 and Vβ8.2. Other CD1d-restricted NKT cells express more variable TCR. Both TCR invariant and TCR variant classes of CD1d-restricted T cells can be detected by binding of CD1d-tetramers loaded with α-GalCer (Benlagha et al., *J Exp Med* 191:1895-1903 (2000); Matsuda et al., *J Exp Med* 192:741-754 (2000); and Karadimitris et al., *Proc Natl Acad Sci USA* 98:3294-3298 (2001)). CD1d-restricted NKT cells, as defined in this application (CD1d-restricted NKT), include cells that express either invariant or variant TCR and that bind or are activated by CD1d loaded with either α-GalCer or with related ceramide-like glycolipid antigens. CD1d-restricted NKT cells, as defined in this application (CD1d-NKT), include cells that express either invariant or variant TCR and that bind or are activated by CD1d loaded with either α-GalCer or with related sphingolipids that have α-linked galactose or glucose including molecules such as OCH, which differs from α-GalCer by having a shortened long-chain sphingosine base (C5 vs. C14) and acyl chain (C24 vs. C26) (Miyamoto et al., *Nature* 413:531-4 (2001)).

CD1d-restricted NKT have been shown to have direct cytotoxic activity against targets that express CD1d. It is likely, however, that the effect of CD1d-restricted NKT on immune responses is amplified through recruitment of other lymphocytes either by direct interaction or, perhaps even more importantly, by indirect recruitment through interaction with DC. CD1d-restricted NKT have the unique ability to secrete large quantities of IL-4 and IFN-γ early in an immune response. Secretion of IFN-γ induces activation of DC which produces interleukin-12 (IL-12). IL-12 stimulates further IFN-γ secretion by NKT cells and also leads to activation of NK cells which secrete more IFN-γ.

Since CD1d-restricted NKT are able to rapidly secrete large amounts of both IL-4 and IFN-γ, the polarization of immune responses will depend on whether the effect of pro-inflammatory IFN-γ or anti-inflammatory IL-4 cytokines predominate. This has been reported to be, in part, a function of the relative frequency of different subsets of CD1d-restricted NKT. These subsets include (i) an invariant CD1d-restricted NKT population that is negative for both CD4 and CD8 and that gives rise to predominantly a TH1 type response including secretion of pro-inflammatory IFN-γ and TNF-α and (ii) a separate population of CD1d-restricted NKT that is CD4+ and that gives rise to both a TH1 type and TH2 type response including secretion of the anti-inflammatory Th2-type cytokines IL-4, IL-5, IL-10 and IL-13 (Lee et al., *J Exp Med* 195:637-41 (2002); and Gumperz et al., *J Exp Med* 195:625-36 (2002)). In addition, NKT cell activity is differentially modulated by depending on the particular ceramide-like glycolipid bound to CD1d (see, e.g., U.S. Pat. No. 7,772,380)). Compositions of the present invention include embodiments with selective association of CD1d with these functionally different ceramide-like glycolipids and the related α-glycosylceramides. Local factors that influence activation of CD1d-restricted NKT subsets include the cytokine environment and, importantly, the DC that are recruited to that environment.

A family of ceramide-like glycolipids (i.e., α-galactosylceramide (α-GalCer) and related α-glycosyl ceramides), have been shown to stimulate strong CD1d-restricted responses by murine NKT cells (Kawano et al., 1997). These compounds contain an α-anomeric hexose sugar (galactose or glucose being active for NKT cell recognition), distinguishing them from the ceramides that commonly occur in mammalian tissues which contain only β-anomeric sugars. These compounds are known to occur naturally in marine sponges, the source from which they were originally isolated, and became of interest to immunologists when it was demonstrated that α-GalCer induced dramatic tumor rejection as a result of immune activation when injected into tumor bearing mice (Kobayashi et al., *Oncol. Res.* 7:529-534 (1995)). Subsequently, this activity was linked to the ability of α-GalCer to rapidly activate NKT cells through a CD1d dependent mechanism. It has now been shown that α-GalCer binds to CD1d, thus creating a molecular complex that has a measurable affinity for the TCRs of NKT cells (Naidenko et al., *J Exp. Med.* 190:1069-1080 (1999); Matsuda et al., *J Exp. Med.* 192:741 (2000); Benlagha et al., J Exp. Med. 191:1895-1903 (2000)). Thus, α-GalCer provides a potent agent that can enable activation of the majority of NKT cells both in vitro and in vivo.

The most extensively studied NKT activating α-GalCer, called KRN7000 in the literature, is a synthetic molecule that has a structure similar to natural forms of α-GalCer that were originally isolated from a marine sponge on the basis of their anti-cancer activity in rodents (Kawano et al., *Science* 278: 1626-1629 (1997); Kobayashi et al., 1995; Iijima et al., *Bioorg. Med. Chem.* 6:1905-1910 (1998); Inoue et al., *Exp. Hematol.* 25:935-944 (1997); Kobayashi et al., *Bioorg. Med. Chem.* 4:615-619 (1996a) and *Biol. Pharm. Bull.* 19:350-353 (1996b); Uchimura et al., *Bioorg. Med. Chem.* 5:2245-2249 (1997a); Uchimura et al., *Bioorg. Med. Chem.* 5:1447-1452 (1997b); Motoki et al., *Biol. Pharm. Bull.* 19:952-955 (1996a); Nakagawa et al., *Oncol. Res.* 10:561-568 (1998); Yamaguchi et al., *Oncol. Res.* 8:399-407 (1996)). One synthetic analogue of KRN7000 with a truncated sphingosine base showed an enhanced ability to suppress autoimmunity in a mouse model of experimental allergic encephalomyelitis (EAE) (Miyamoyo et al., *Nature* 413:531-534 (2001)). Other variants altered in the α-GalCer sphingosine base are identified in U.S. Pat. No. 5,936,076.

A large body of literature dating from November 1997 to the present time has studied the mechanism by which KRN7000 activates the immune system of mammals (Kawano et al., *Science* 278:1626-1629 (1997); Benlagha et al., *J Exp. Med.* 191:1895-1903 (2000); Burdin et al., *Eur. J Immunol.* 29:2014-2025 (1999); Crowe et al., *J. Immunol.* 171:4020-4027 (2003); Naidenko et al., *J Exp. Med.* 190: 1069-1080 (1999); Sidobre et al., *J. Immunol.* 169:1340-1348 (2002); Godfrey et al., *Immunol. Today* 21:573-583 (2000); Smyth and Godfrey, *Nat. Immunol.* 1:459-460 (2000)). These studies uniformly show that the proximal mechanism for the effect of KRN7000 is the binding of this compound to a CD1d protein, which is expressed on most hematopoietic cells, as well as some epithelial and other cell lineages. The binding of KRN7000 to CD1d creates a molecular complex that is recognized with high affinity by the T cell antigen receptors (TCRs) of a subset of T lymphocytes called natural killer T cells (NKT cells). Recognition of the KRN7000/CD1d complex leads to rapid activation of the NKT cells, which reside in the liver, spleen and other lymphoid organs and have the potential to traffic to potentially any tissue. Activated NKT cells rapidly secrete a wide range of chemokines and cytokines, and also have the capability of activating other cell types such as dendritic cells and natural killer (NK) cells. The chain of events that follows the activation of NKT cells by KRN7000/CD1d complexes has been shown to have many potential downstream effects on the immune system. For example, in the setting of certain types of infections this can lead to an adjuvant effect that boosts the adaptive immunity to the infection and promotes healing. Or, in the setting of certain types of autoimmune diseases, the activation of NKT cells by KRN7000 can alter the course of the autoimmune response in a way that suppresses tissue destruction and ameliorates the disease.

A number of indirect mechanisms contribute to the protective effect of CD1d-restricted NKT cells. Activation of NKT cells by administration of α-GalCer in vivo results in concomitant activation of NK cells (Eberl and MacDonald, *Eur. J. Immunol.* 30:985-992 (2000); and Carnaud et al., *J. Immunol.* 163:4647-4650 (1999)). In mice deficient in NKT cells, α-GalCer is unable to induce cytotoxic activity by NK cells. NKT cells also enhance the induction of classical MHC class I restricted cytotoxic T cells (Nishimura et al., *Int Immunol* 12:987-94 (2000); and Stober et al., *J Immunol* 170:2540-8 (2003)).

As discussed in more detail below, the present invention includes a glycolipid. As used herein, a "glycolipid" refers to a chemical compound comprising a carbohydrate moiety bound to a lipophilic moiety represented by general structure:

G-L where L is a lipid and G is a carbohydrate. As used herein, a "lipid" refers to an organic compound that is soluble in fats, oils, and non-polar solvents, such as organic solvents. The term "lipophilic" refers to the property of an organic compound to dissolve in fats, oils, lipids, and non-polar solvents, such as organic solvents. Lipophilic compounds are sparingly soluble or insoluble in water. In some embodiments, G is a saccharide, which may be a hexose or pentose, and may be a mono-, di-, tri-, oligo or polysaccharide, or a derivative thereof. The sugars of interest include allose, altrose, glucose, mannose, gulose, idose, galactose, talose, fructose, maltose, lactose and sucrose. The linkage between the sugar and the lipid may be at any of the O atoms, usually at position 1, 2, 3 or 4, more usually at position 1. The linkage may be in the alpha or beta configuration. In some specific embodiments, the linkage is in the alpha configuration.

In some embodiments, the glycolipids may have the structure:

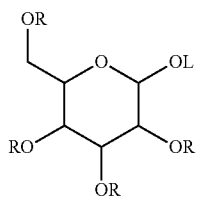

where L is a lipid, and R is selected from the group consisting of H, a pentose sugar, a hexose sugar, an oligo- or polysaccharide; or an alkyl, aryl or alkenyl group, such as a C1 to C6 lower alkyl, which alkyl is optionally substituted, which substituent may include, without limitation, an alkyl, aryl, alkenyl, aralkyl, aralkenyl, cycloalkyl, cycloalkylalkyl or cycloalkylalkenyl group; and may contain one or more N, S or O heteroatoms. Each of the O atoms may be in the α or β orientation, e.g. glucose, galactose, mannose, etc.

A number of lipids find use as L, including C8 to C30 fatty acids, long chain secondary alcohols, long chain amino alcohols, amides of fatty acids with long-chain di- or trihydroxy bases; and the like. For example, a glycosyl moiety (one or several units) may be linked to one hydroxyl group of a fatty alcohol or hydroxy fatty alcohol, or to a carbonyl group of a fatty acid. Non-limiting examples of suitable lipids include ceramides, sphingomyelin, cerebrosides, and the like, including sphiongosine, dihydrosphingosine, C20-dihydrosphingosine, phytosphingosine, C20-phytosphingosine, dehydrophytosphingosine, and sphingadienine.

In some embodiments, the glycolipid is a ceramide-like glycolipid, e.g., an α-galactosylceramide, also referred to herein as α-GalCer, or an analog thereof, such as α-C-GalCer, which contains a C-glycoside bond instead of an β-glycosidic linkage between the sugar and the sphingoid base.

Ceramides are N-acyl lipophilic derivatives of a long chain base or sphingoid, the commonest in animals being sphingosine and in plants phytosphingosine. Generally, the N-acyl lipophilic moiety is a fatty acid, which in some embodiments, comprise C3-C27 long carbon chains. These fatty acid carbon chains can be substituted, unsubstituted, saturated, unsaturated, branched, unbranched alkyl, alkenyl or alkynyl chains. As used herein, the term "ceramide" will include any of the ceramide analogs, synthetic or natural.

As used herein, the terms "ceramide-like glycolipid" and "glycolipid ceramide" are used interchangeably. A ceramide-like glycolipid is a glycolipid comprising an N-acyl lipophilic moiety and a sphingosine moiety or an analog thereof (e.g., a ceramide), and is represented by the general Formula (VII), wherein R2 of Formula (VII) can be a linear or branched, substituted or unsubstituted alkyl, alkenyl or alkynyl chain, or substituted or unsubstituted, saturated or unsaturated cyclic ring, or a substituted or unsubstituted aryl ring:

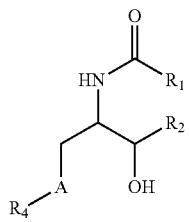

Formula (VII)

In this Formula (VII), R4 is a carbohydrate and the rest of the molecule is a ceramide or an analog thereof. In some embodiments, R4 can be a saccharide. Ceramide-like glycolipids wherein the R4 is a saccharide is referred to herein as a glycosylceramide. In some embodiments, the saccharide may be a hexose or pentose or analogs thereof. In some other embodiments, the hexose or pentose or analogs thereof can be mono-, di-, tri-, oligo or polysaccharide, or a derivative thereof. Ceramide-like glycolipids wherein the saccharide of R4 is a galactoside (α- or β-linked) are referred to herein as galactosylceramides. In some embodiments, R4 is an α-galactoside. In some embodiments, A, if present can be —O—, —CH2- or —S; or is a single bond. In some particular embodiments, A is O.

R1 and R2 can be the same or different. In some embodiments R1, R2, or both can be a substituted or unsubstituted alkane, alkene, cycloalkyl; alkanes or alkenes substituted with heteroatoms; or substituted or unsubstituted aryls or heteroaryls. In some particular embodiments, R1, R2, or both can be substituted or unsubstituted alkyl or alkenyl chains with heteroatoms, cyclic rings, or aryl rings incorporated within the chain. In some embodiments R1, R2, or both contain contiguous or non-contiguous double bonds. These double bonds can be of E/Z configuration. In some embodiments, R2 is a saturated or unsaturated long chain C3-C27 alkyl or alkene group with at least one hydroxyl group attached therein.

In particular embodiments, R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is an optionally substituted aromatic ring, or an aralkyl.

In some of the above embodiments, R2 is a substituted or unsubstituted, branched or unbranched alkyl, alkenyl or alkynyl chain. In some particular embodiments, R2 is one of the following (a)-(e):
  (a) —$CH_2(CH_2)_xCH_3$,
  (b) —$CH(OH)(CH_2)_xCH_3$,
  (c) —$CH(OH)(CH_2)_xCH(CH_3)_2$,
  (d) —$CH=CH(CH_2)_xCH_3$,
  (e) —$CH(OH)(CH_2)_xCH(CH_3)CH_2CH_3$,
wherein x is an integer ranging from 0-40.

In some other embodiments, R2 is —$CH(OH)(CH_2)_xCH_3$, wherein x is an integer ranging from 4-17. In some particular embodiments, R2 is —$CH(OH)(CH_2)_xCH_3$.

Non-limiting examples of ceramide-like glycolipids are described herein and also can be found, e.g., in Porcelli, U.S. Patent Appl. Publ. No. 2006/0052316, Tsuji, U.S. Patent Appl. Publ. No. 2006/0211856, Jiang, U.S. Patent Appl. Publ. No. 2006/0116331, Hirokazu et al., U.S. Patent Appl. Publ. No. 2006/0074235, Tsuji et al., U.S. Patent Appl. Publ. No. 2005/0192248, Tsuji, U.S. Patent Application No. 2004/0127429, and Tsuji et al., U.S. Patent Application No. 2003/0157135, all of which are incorporated by reference herein in their entireties.

In certain embodiments, a modified ceramide-like glycolipid comprises a glycosylceramide or analog thereof or an α-galactosylceramide or analog thereof.

In some embodiments, the glycosylceramide or analog thereof comprises Formula I:

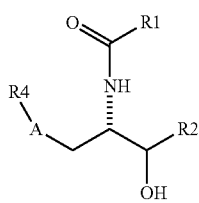

(Formula I)

wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):
  (a) —$CH_2(CH_2)_xCH_3$,
  (b) —$CH(OH)(CH_2)_xCH_3$,
  (c) —$CH(OH)(CH_2)_xCH(CH_3)_2$,
  (d) —$CH=CH(CH_2)_xCH_3$,
  (e) —$CH(OH)(CH_2)_xCH(CH_3)CH_2CH_3$,
wherein X is an integer ranging from 4-17;

R4 is an α-linked or a β-linked monosaccharide, or when R1 is a linear or branched $C_1$-$C_{27}$ alkane, R4 is:

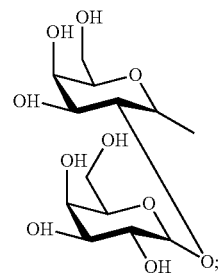

and

A is O or —$CH_2$.

In another embodiment, the α-galactosylceramide or analog thereof comprises Formula II:

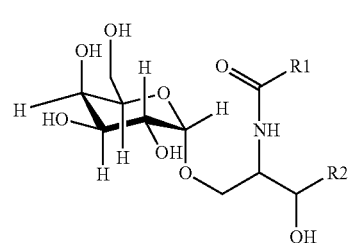

(Formula II)

wherein

R1 is a linear or branched $C_1$-$C_{27}$ alkane or $C_2$-$C_{27}$ alkene; or R1 is —C(OH)—R3 wherein R3 is linear or branched $C_1$-$C_{26}$ alkane or $C_2$-$C_{26}$ alkene; and R2 is one of the following (a)-(e):
  (a) —$CH_2(CH_2)_xCH_3$,
  (b) —$CH(OH)(CH_2)_xCH_3$,
  (c) —$CH(OH)(CH_2)_xCH(CH_3)_2$,
  (d) —$CH=CH(CH_2)_xCH_3$,
  (e) —$CH(OH)(CH_2)_xCH(CH_3)CH_2CH_3$,
wherein X is an integer ranging from 4-17.

In another embodiment, the modified ceramide-like glycolipid comprises an α-galactosylceramide or analog thereof comprising Formula III:

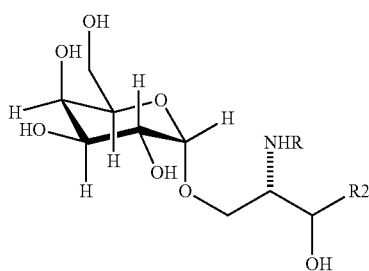
(Formula III)

wherein R is —C(O)R1, wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is an optionally substituted aromatic ring, or an aralkyl, and R2 is one of the following (a)-(e):

(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$, wherein X is an integer ranging from 4-17.

In a further embodiment, R1 is selected from the group consisting of

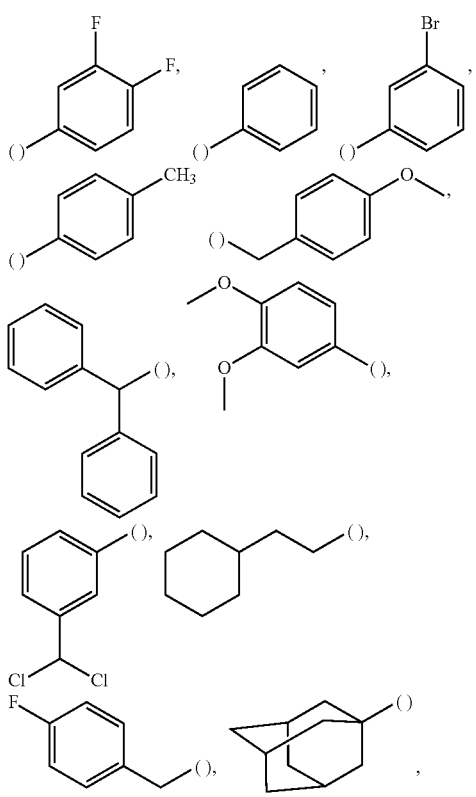

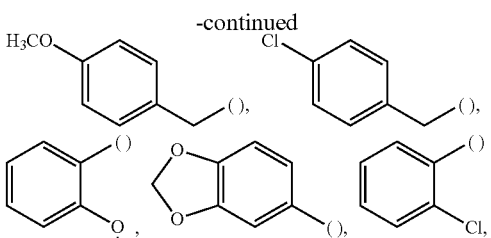
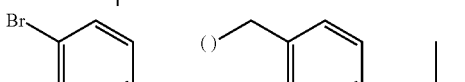
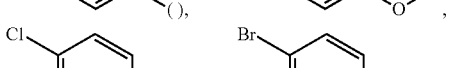
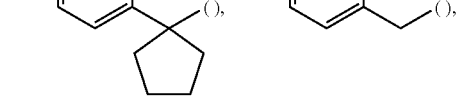
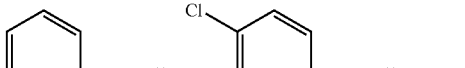
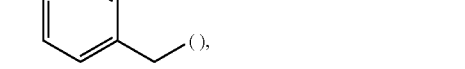
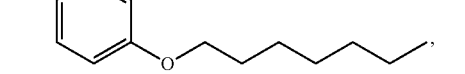
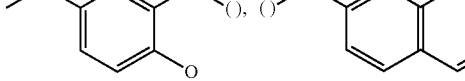
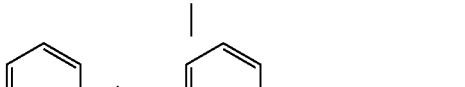
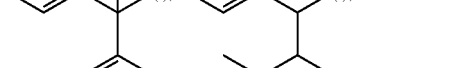

where ( ) represent the point of attachment of R1 to the compound of Formula III. In some embodiments, the R1 is substituted with a photoreactive group. The photoreactive group is attached to the R1 group at any appropriate position of the R1 group. For example, in some embodiments, the photoreactive group is attached to the phenyl ring of the R1 group. In some other embodiments, the photoreactive group is attached to the pendent substitutents of the phenyl ring.

In another embodiment, the α-galactosylceramide or analog thereof comprises (2S,3S,4R)-1-O-(α-D-galactopyranosyl)-N-hexacosanoyl-2-amino-1,3,4-octadecanetriol (KRN7000) or (2S,3S)-1-O-(α-D-galactopyranosyl)-N-hexacosanoyl-2-amino-1,3-octadecanediol).

In another embodiment, the α-galactosylceramide or analog thereof comprises (2S,3S,4R)-1-CH$_2$— (α-galactopyranosyl)-N-hexacosanoyl-2-amino-1,3,4-octadecanetriol (α-C-GalCer).

Other non-limiting examples of ceramide-like glycolipids are described in U.S. Pat. No. 7,273,852; U.S. Pat. No. 6,531,453; and U.S. Pat. No. 5,936,076, U.S. Pat. No. 7,772,380, all of which are incorporated herein by reference in their entirety.

"Modified glycolipids" as referred to herein include glycolipids that comprise a functional group that allows for a stable covalent linkage to a protein (e.g., CD1d). The term encompasses naturally-occurring glycolipids that have been modified through human intervention to comprise such a functional group and also refers to synthetic glycolipids.

The modified glycolipid of the present invention may comprise a functional group that allows for a stable covalent linkage to a protein (e.g., CD1d) within or at the terminus of an acyl chain of the glycolipid. In some of those embodiments wherein the modified glycolipid is a ceramide-like glycolipid, the ceramide-like glycolipid is modified within or at the terminus of the N-acyl lipophilic moiety, such as an acyl chain.

In some embodiments, a functional group that forms a stable covalent linkage to a protein such as CD1d, is a group that can be activated photochemically or thermally. In some embodiments, such a functional group can be activated photochemically. As used herein, the term "photoreactive group" or "photoreactive functional group" refers to a functional group that is chemically inert, but becomes reactive when exposed to energy from a light source. The photoreactive group can become reactive when irradiated with visible light or in some embodiments, ultraviolet light.

In particular embodiments, photoreactive groups that can be activated using an UV light are chosen because a compound possessing such a group (for example, a glycolipid with a photoreactive group) can be added to the protein (e.g., CD1d) and the timing of covalent bond formation can be controlled by UV irradiation at any given timepoint.

Any photoreactive functional group can be used in the present invention. In some embodiments, the photoreactive groups that can be used to form a covalent bond between a glycolipid and the CD1d protein include any one of aryl azides, azidomethyl coumarins, benzophenones, anthraquinones, certain diazo compounds, diazirines and psoralen derivatives. Generally, a photoactivated reaction between a compound possessing a photoreactive functional group and CD1d protein can be illustrated as follows in Scheme 1.

Scheme 1

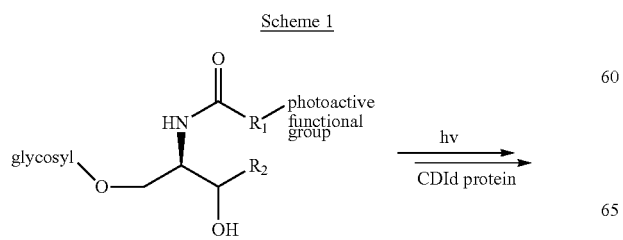

-continued

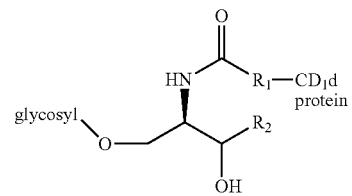

In some embodiments, aryl azides and diazirines can be used as photoreactive functional groups. In some of the specific embodiments, the following photoreactive functional groups can be used (Scheme 2)

Scheme 2

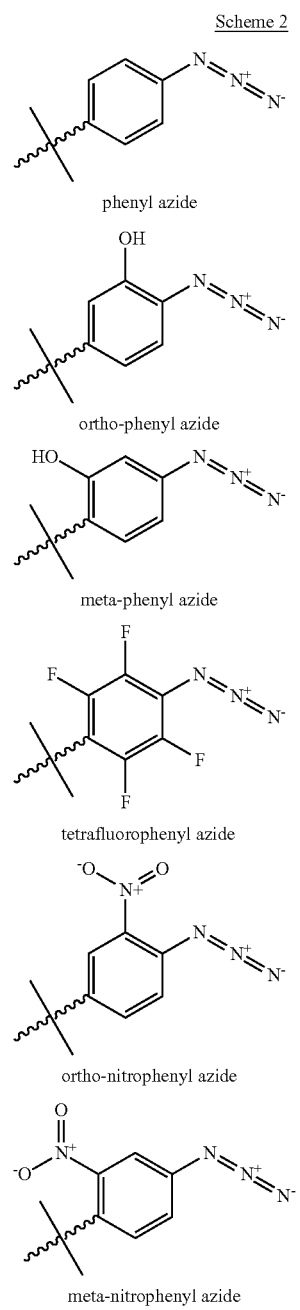

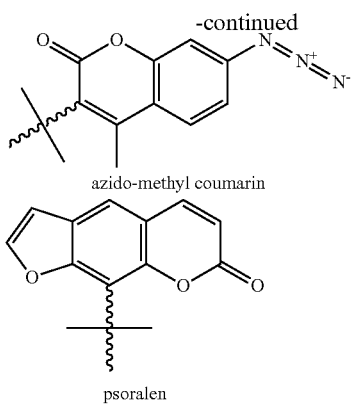

azido-methyl coumarin psoralen

Squiggle bonds represent position of attachment of these photoreactive functional groups to the glycolipid, such as within or at the terminus of an acyl side chain of the glycolipid.

In some embodiments, photoreactive functional groups that can be activated with long ultraviolet irradiation (e.g., 300 to 460 nm) are used in the presently disclosed methods and compositions.

In some embodiments of the present invention, the lipophilic group of a glycolipid is connected to the carbohydrate group via an acyl bond. The acyl bond could be either through an O or N or the like. In that respect, the "acyl side chain" is shown as below:

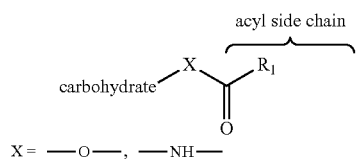

X = —O—, —NH—

The acyl side chain can be linear or branched. In those embodiments wherein the acyl side chain is linear, when referring to the length of the linear acyl side chain (not including the functional group that allows for a stable covalent linkage to a protein), the carbonyl carbon is included. In some embodiments, the linear acyl side chain has about 5, 6, 7, 8, 9, 10, 11, 12, 13, 14, 15, 16, 17, 18, or more atoms (excluding the hydrogens), which can include one or more heteroatoms.

In some of these embodiments, the linear acyl side chain has at least 11 atoms (excluding the hydrogens), which can include one or more heteroatoms. In certain embodiments, the acyl side chain comprises about 11 to about 14 atoms (excluding the hydrogens).

In certain embodiments, the linear acyl side chain has one of the following structures:

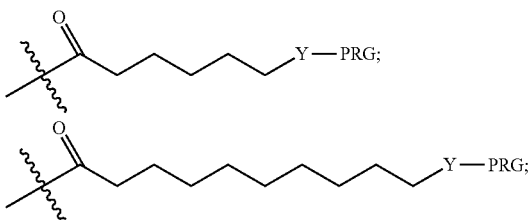

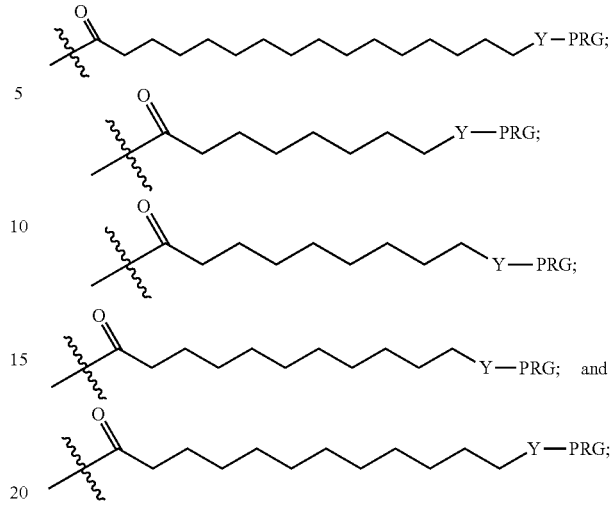

wherein Y if present is —O—, —CH$_2$—, —S—, —OCH$_2$—, —SCH$_2$—, —CH$_2$CH$_2$—; or a bond, and PRG is a photoreactive group.

In some embodiments, the glycolipid is a ceramide-like glycolipid. In some of the above embodiments, wherein the glycolipid is a ceramide-like glycolipid, the photoreactive functional group is attached to the N-acyl lipophilic moiety of the ceramide-like glycolipid. In particular embodiments, the photoreactive functional group is attached within or at the terminus of the fatty acid acyl side chain. In particular embodiments, the ceramide-like glycolipid is a glycosylceramide or an analog thereof. In other embodiments, the ceramide-like glycolipid is an α- or β-linked galactosylceramide or an analog thereof.

In particular embodiments, the photoreactive functional group that is added to a glycolipid is a benzophenone group. The term "benzophenone" is well-understood by a person skilled in the art. Generally, benzophenones are represented by the general formula $C_6H_5$—CO—$C_6H_5$ as shown below.

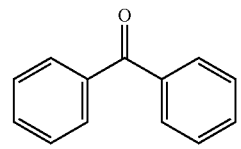

As used herein, benzophenones or analogs thereof can be used in certain embodiments of the present inventions. For example, in some embodiments isosteres of phenyl groups (i.e. thiophenes and the like) can be used in the place of phenyl groups. In some other embodiments, the phenyl groups of analogs thereof can be substituted with other functional groups. In some other embodiments, the phenyl groups and analogs thereof are unsubstituted.

Thus, the modified glycolipid of the present invention may comprise a benzophenone group. In some of these embodiments, the glycolipid comprises a benzophenone group on an acyl chain of the glycolipid. In particular embodiments, the benzophenone group is covalently bound to the N-acyl lipophilic moiety of a ceramide-like glycolipid. In some of these embodiments, the benzophenone group is found at the terminus of the acyl chain of a ceramide-like glycolipid. Non-limiting examples of said modified glycolipids are provided in Table 1.

TABLE 1

Non-limiting examples of benzophenone-modified ceramide-like glycolipids.

| Compound | CHO group | Structure |
|---|---|---|
| DB11-1 | α-D-Gal | 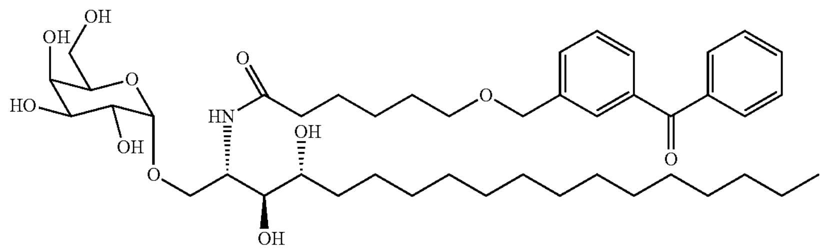 [SMILES: CCCCCCCCCCCCCC[C@@H](O)[C@@H](O)[C@H](COC1OC(CO)C(O)C(O)C1O)NC(=O)CCCCCOCc1cccc(C(=O)c2ccccc2)c1] |
| DB11-2 | α-D-Gal | 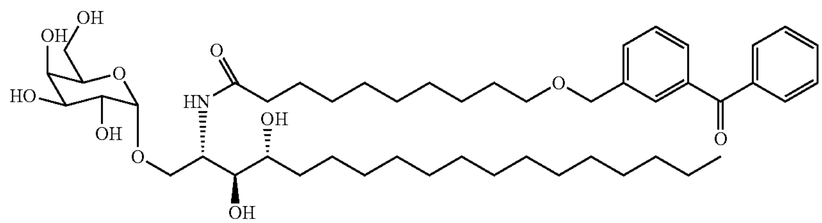 [SMILES: CCCCCCCCCCCCCC[C@@H](O)[C@@H](O)[C@H](COC1OC(CO)C(O)C(O)C1O)NC(=O)CCCCCCCCCOCc1cccc(C(=O)c2ccccc2)c1] |
| DB11-3 | α-D-Gal | 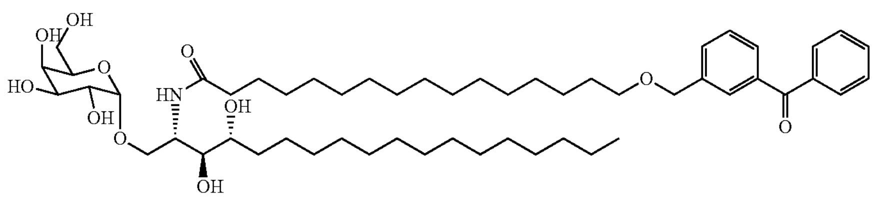 [SMILES: CCCCCCCCCCCCCC[C@@H](O)[C@@H](O)[C@H](COC1OC(CO)C(O)C(O)C1O)NC(=O)CCCCCCCCCCCCCCCOCc1cccc(C(=O)c2ccccc2)c1] |
| DB12-6 | α-D-Gal | 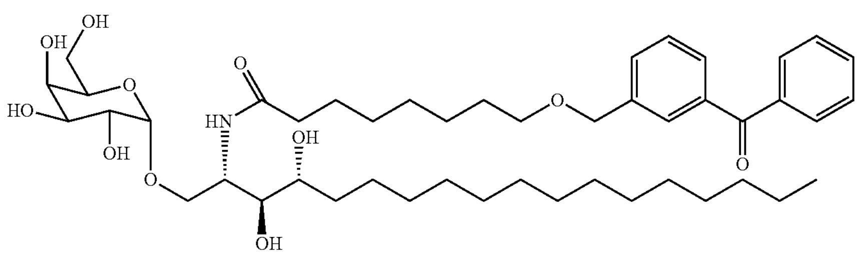 [SMILES: CCCCCCCCCCCCCC[C@@H](O)[C@@H](O)[C@H](COC1OC(CO)C(O)C(O)C1O)NC(=O)CCCCCCCOCc1cccc(C(=O)c2ccccc2)c1] |
| DB12-7 | α-D-Gal | 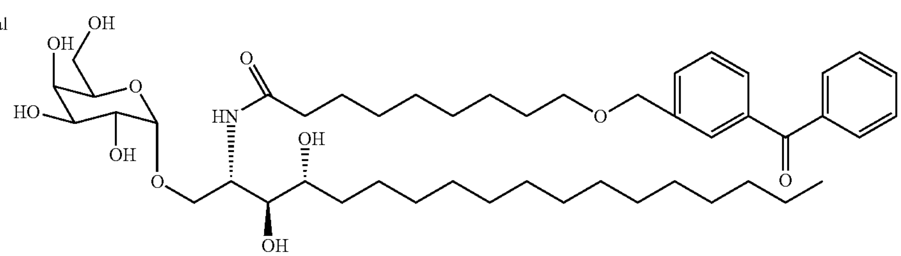 |
| DB12-8 | α-D-Gal | 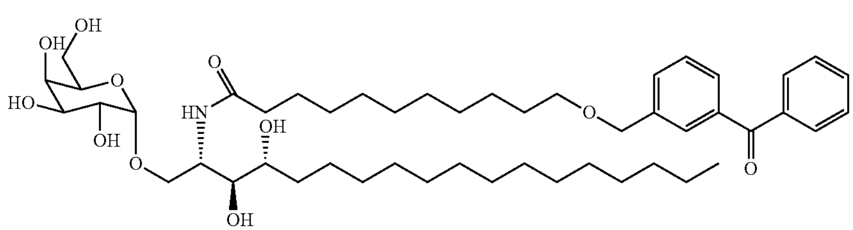 [SMILES: CCCCCCCCCCCCCC[C@@H](O)[C@@H](O)[C@H](COC1OC(CO)C(O)C(O)C1O)NC(=O)CCCCCCCCCCOCc1cccc(C(=O)c2ccccc2)c1] |

TABLE 1-continued

Non-limiting examples of benzophenone-modified ceramide-like glycolipids.

| Compound | CHO group | Structure |
|---|---|---|
| DB12-9 | α-D-Gal | 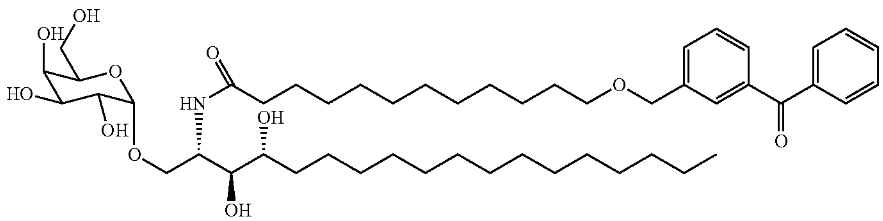 [SMILES: CCCCCCCCCCCCCC[C@@H](O)[C@@H](O)[C@H](COC1OC(CO)C(O)C(O)C1O)NC(=O)CCCCCCCCCCCOCc1cccc(C(=O)c2ccccc2)c1] |

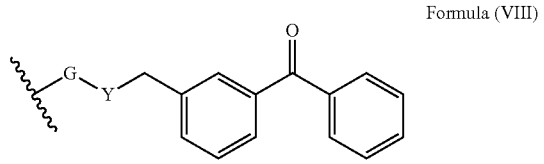

Thus, in some embodiments, R1 of Formula (VII) is substituted with a benzophenone moiety. In particular embodiments, the benzophenone moiety is substituted at the terminus. In some other embodiments, R1 of Formula (VII) is represented by the following Formula (VIII):

Formula (VIII)

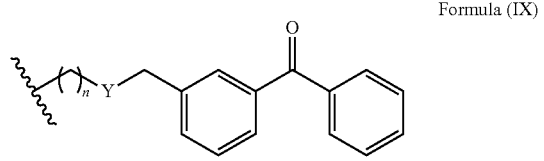

where Y is —O—, —CH$_2$— or —S—, and G is a linear or branched C$_1$-C$_{27}$ alkane or C$_2$-C$_{27}$ alkene; or G is —C(OH)—R3 wherein R3 is a linear or branched C$_1$-C$_{26}$ alkane or C$_2$-C$_{26}$ alkene; or R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring; or R1 is an optionally substituted aromatic ring, or an aralkyl.

In some embodiments, R1 of Formula (VII) is represented by the following Formula (IX):

Formula (IX)

where Y is —O—, —CH$_2$— or —S—, and n is an integer ranging from 0-30. In some embodiments, n is an integer ranging from 3-17.

The presently disclosed modified glycolipids and modified glycolipid/protein complexes can be synthesized using any method known in the art, including those methods disclosed herein.

According to one embodiment of the invention, the general synthesis of benzophenone modified glycolipids is shown in Scheme 3. Accordingly, a benzophenone carboxylic acid derivative of Formula (IV) is activated with a suitable activating agent and reacted via peptide coupling with a ceramide-like glycolipid of Formula (V) to afford the desired benzophenone-modified glycolipids. Any activating agents, reagents and solvents known in the skill of art as suitable for a peptide coupling between an amine and a carboxylic acid can be used for the coupling reaction of benzophenone carboxylic acid derivative (IV) and the ceramide-like glycolipid (V).

Scheme 3

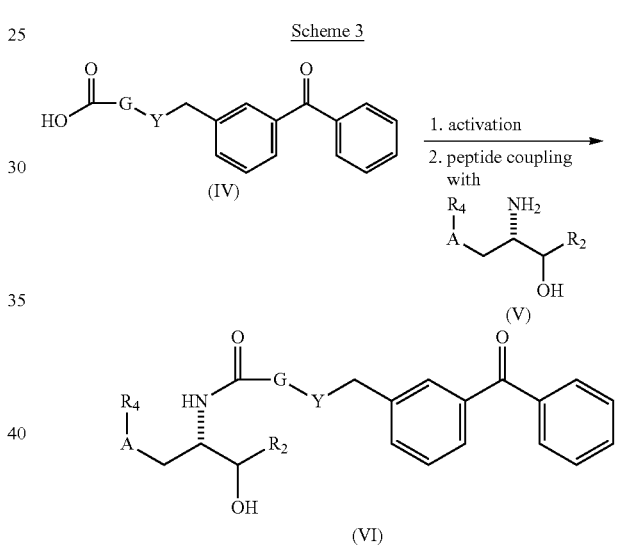

In some embodiments, Y is —O—, —CH$_2$— or —S—; G is a linear or branched C$_1$-C$_{27}$ alkane or C$_2$-C$_{27}$ alkene; or G is —C(OH)—R3 wherein R3 is a linear or branched C$_1$-C$_{26}$ alkane or C$_2$-C$_{26}$ alkene; or R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring; R$_4$ is a substituted or unsubstituted sugar or analogs thereof; A, if present, is —O—, —CH$_2$—; or is a single bond; and R$_2$ is substituted or unsubstituted C3-C40 alkyl, alkenyl or alkynyl chain. In some embodiments, G is —(CH$_2$)$_n$—, wherein n is an integer ranging from 0-20 and Y is O. In some other embodiments, R2 of the modified glycolipid comprising a benzophenone group of Formula (VI) is one of the following (a)-(e):

(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$, wherein x is an integer ranging from 0-40.

In some of the other embodiments, R2 of the modified glycolipid comprising a benzophenone group of Formula (VI) is —CH(OH)(CH$_2$)$_x$CH$_3$, wherein x is an integer ranging from 4-17. In some particular embodiments, R2 of the modified glycolipid comprising a benzophenone group of Formula (VI) is —CH(OH)(CH$_2$)$_{13}$CH$_3$. In some other embodiments, R4 is an α-galactosyl.

According to some embodiments of the invention, the benzophenone carboxylic acid derivative of Formula (IV) wherein G is —(CH$_2$)$_n$—, wherein n is an integer ranging from 0-20 and Y is O, can be synthesized according to the Schemes 4 and 5.

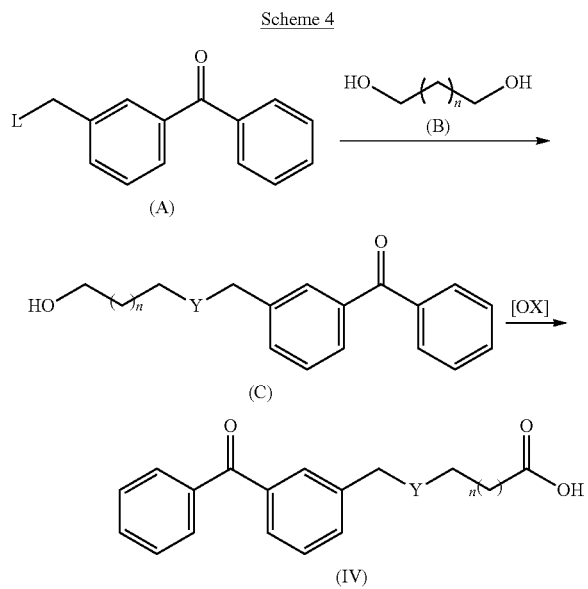

Accordingly, a benzophenone derivative (A) comprising a suitable leaving group is reacted with a diol derivative (B) to form the hydroxyl derivative (C). Any suitable leaving group L known in the skill of art can be used for this reaction. In some embodiments, the leaving group L can be Br, Cl, I, tosyl, mesyl and the like. In some particular embodiments, the leaving group L is bromine. The hydroxyl derivative is then oxidized to the carboxyl acid derivative (IV) wherein Y is O using any of the oxidization reagents suitable for oxidizing an alcohol to an acid. In particular, oxidizing agents that oxidize primary alcohol to acids are well known in the art. In some embodiments, the oxidizing agent is pyridinium dichromate (PDC).

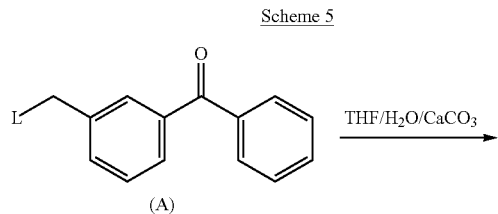

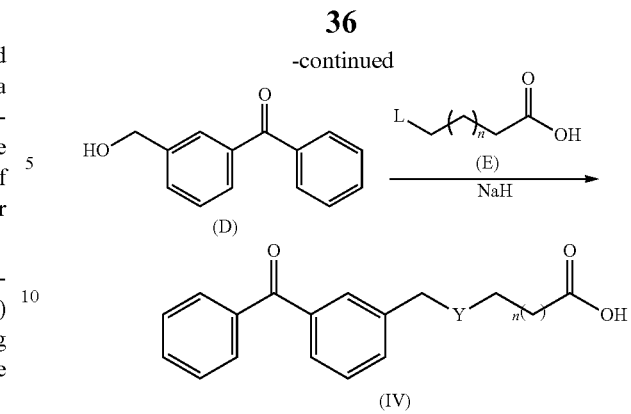

In some embodiments, the benzophenone carboxylic acid derivative of formula (V) wherein G is —(CH$_2$)$_n$—, wherein n is an integer ranging from 0-20 and Y is O can be synthesized as illustrated in Scheme 3. Accordingly, benzophenone derivative (A) is reacted with THF/H$_2$O in the presence of CaCO$_3$ to form the corresponding alcohol derivative (D). The alcohol derivative D is then reacted with a carboxylic acid derivative comprising a leaving group L under basic conditions to yield the benzophenone carboxylic acid derivative (IV) wherein Y is O. Any suitable leaving group L known in the skill of art can be used for this reaction. In some embodiments, the leaving group L can be Br, Cl, I, tosyl, mesyl and the like. In some particular embodiments, the leaving group L is bromine.

In a modified glycolipid/protein complex of the invention, a modified glycolipid is "physically associated" with a protein, e.g., CD1d protein, to produce a "modified glycolipid/CD1d complex." In certain embodiments, the modified glycolipid/CD1d complex further comprises a heterologous antigen or a targeting molecule. By "physically associated" is meant a direct interaction with the CD1d protein. In certain embodiments, the ceramide-like glycolipid is physically associated with a CD1d protein through covalent means. In some embodiments, the heterologous antigen or targeting molecule, or both are physically associated with a CD1d protein (e.g., through covalent means).

A modified glycolipid comprising a photoreactive group can be covalently bound to a protein (e.g., CD1d) by contacting the modified glycolipid with the protein and irradiating the modified glycolipid with light (e.g., visible light or ultraviolet light. In some embodiments wherein the photoreactive group is a benzophenone group, the modified glycolipid comprising the benzophenone group can be covalently bound to a protein (e.g., CD1d) by contacting the modified glycolipid with the protein and irradiating the benzophenone-modified glycolipid and the protein with ultraviolet light (i.e., light having a wavelength of about 10 nm-about 400 nm). In particular embodiments, the modified glycolipid is contacted with the protein by incubating the two molecules in a solution. In some of these embodiments, the solution comprises a buffered saline solution. In certain embodiments, the modified glycolipid and protein are irradiated with ultraviolet light with a long wavelength (i.e., about 300 nm to about 460 nm, including but not limited to about 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, and 460 nm). In certain embodiments, the modified glycolipid and protein are irradiated with UV with a wavelength of about 365 nm. In some embodiments, the modified glycolipid and protein are irradiated using a UV lamp that is placed about 1 inch above the sample. In some embodiments, the modified glycolipid and protein are irradiated for about 5 minutes, about 10 minutes, about 15 minutes, about 30 minutes, about 40 minutes, about 50 minutes, about 1 hour, about 2 hours, or longer. In particular embodiments, the modified glycolipid and protein are irradiated for about 1 hour.

Detection of the modified glycolipid physically associated with the protein can be accomplished by methods known to one of skill in the art. By stably binding a modified glycolipid to a protein, e.g., CD1d protein, a modified glycolipid/CD1d complex can be made. In certain embodiments, the compositions of the invention allow for simultaneous administration of a glycolipid and a protein, e.g., CD1d protein, to an antigen presenting cell.

A modified glycolipid/protein complex of the present invention can comprise a single glycolipid, or can comprise heterogeneous mixtures of glycolipids. That is, a protein or multiple proteins can be physically associated with a single glycolipid or can be physically associated with a mixture of glycolipids.

The term "optionally substituted" as used herein means either unsubstituted or substituted with one or more substituents including halogen (F, Cl, Br, I), alkyl, substituted alkyl, aryl, substituted aryl, or alkoxy.

The term "alkyl", as used herein by itself or part of another group refers to a straight-chain or branched saturated aliphatic hydrocarbon typically having from one to eighteen carbons or the number of carbons designated. In one such embodiment, the alkyl is methyl. Non-limiting exemplary alkyl groups include ethyl, n-propyl, isopropyl, and the like.

The term "substituted alkyl" as used herein refers to an alkyl as defined above having one or more halogen (F, Cl, Br, I) substitutes.

The term "heterocycle" as used herein means a 3- to 10-membered monocyclic or bicyclic heterocyclic ring which is either saturated, unsaturated non-aromatic, or aromatic containing up to 4 heteroatoms. Each heteroatom is independently selected from nitrogen, which can be quaternized; oxygen; and sulfur, including sulfoxide and sulfone. The heterocycle can be attached via a nitrogen, sulfur, or carbon atom. Representative heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, and the like. The term heterocycle also includes heteroaryls.

The term "aryl" as used herein by itself or part of another group refers to monocyclic and bicyclic aromatic ring systems typically having from six to fourteen carbon atoms (i.e., $C_6$-$C_{14}$ aryl) such as phenyl, 1-naphthyl, and the like.

The term "substituted aryl" as used herein refers to an aryl as defined above having one or more substitutes including halogen (F, Cl, Br, I) or alkoxy.

The term "aralkyl" as used herein by itself or part of another group refers to an alkyl as defined above having one or more aryl substituents. Non-limiting exemplary aralkyl groups include benzyl, phenylethyl, diphenylmethyl, and the like.

The term "alkoxy" as used herein by itself or part of another group refers to an alkyl attached to a terminal oxygen atom. Non-limiting exemplary alkoxy groups include methoxy, ethoxy and the like.

The term "alkane" as used herein means a straight chain or branched non-cyclic saturated hydrocarbon. Representative straight chain alkane include -methyl, -ethyl, -n-propyl, -n-butyl, -n-pentyl, -n-hexyl, -n-heptyl, -n-octyl, -n-nonyl and -n-decyl. Representative branched alkane include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

The term "alkene" as used herein means a straight chain or branched non-cyclic hydrocarbon having at least one carbon-carbon double bond. Representative straight chain and branched alkene include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "cycloalkane" as used herein means a saturated cyclic hydrocarbon having from 3 to 15 carbon atoms. Representative cycloalkanes are cyclopropyl, cyclopentyl and the like.

The term "alkylcycloalkene" as used herein by itself or part of another group refers to an alkyl as defined above attached a cylcoalkane as defined above.

The term "cylcoalkene" as used herein means refers to a mono-cyclic non-aromatic hydrocarbon having at least one carbon-carbon double bond in the cyclic system and from 5 to 15 carbon atoms. Representative cycloalkenes include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl -cyclononadienyl, -cyclodecenyl, -cyclodecadienyl and the like. The term "cycloalkene" also include bicycloalkenes and tricycloalkenes. The term "bicycloalkene" as used herein means a bicyclic hydrocarbon ring system having at least one carbon-carbon double bond in one of the rings and from 8 to 15 carbon atoms. Representative bicycloalkenes include, but are not limited to, -indenyl, -pentalenyl, -naphthalenyl, -azulenyl, -heptalenyl, -1,2,7,8-tetrahydronaphthalenyl, and the like. The term "tricycloalkene" as used herein, means a tri-cyclic hydrocarbon ring system having at least one carbon-carbon double bond in one of the rings and from 8 to 15 carbon atoms. Representative tricycloalkenes include, but are not limited to, -anthracenyl, -phenanthrenyl, -phenalenyl, and the like.

The term "aromatic ring" as used herein means a 5 to 14 membered aromatic carbocyclic ring, including both mono, bicyclic, and tricyclic ring systems. Representative aromatic rings are phenyl, napthyl, anthryl and phenanthryl.

The term "oxo" as used herein, means a double bond to oxygen. i.e., C=O.

The term "monosaccharide" as used herein means any of the simple sugars that serve as building blocks for carbohydrates. Examples of monosaccharides include glucose, fucose, galactose, and mannose.

The term "hydroxyl" as used herein refers to a functional group composed of one oxygen bonded to one hydrogen, with the oxygen covalently bonded to another atom, e.g., a carbon. A "hydroxyl-protected glycolipid" of the invention includes a glycolipid, e.g., a synthetic glycolipid, having a hydroxyl group coupled to a protection group.

The modified glycolipids of the invention have been modified to comprise a functional group that can form a stable covalent linkage to a protein (e.g., CD1d). In those embodiments wherein the protein is CD1d and the modified glycolipid is a ceramide-like glycolipid, a "stable modified ceramide-like glycolipid/CD1d complex" is one wherein the modified ceramide-like glycolipid is covalently bound to CD1d and the complex is able to retain significant Natural Killer T (NKT) cell-stimulating activity or the ceramide-like glycolipid remains associated with CD1d in a conformation detected by an antibody such as L363 which is specific for a biologically functional complex after an in vitro incubation (Yu et al. (2007) *J Immunol Methods* 323:11-23, which is herein incorporated by reference in its entirety). In some embodiments, a stable modified ceramide-like glycolipid/CD1d complex retains at least about 50%, at least about 55%, at least about 60%, at least about 65%, at least about 70%, at least about 75%, at least about 80%, at least about 85%, at least about 95%, or more NKT cell-stimulating activity or functional complex detected by an antibody such as L363 after about a 1 day, about 2 days, about 3 days, about 4 days, about 5 days, about 6 days, about 1 week, or longer in vitro incubation. In some of these embodiments, the in vitro incubation occurs at room temperature. In particular embodiments, the in vitro incubation occurs in a buffered saline solution (e.g., PBS+0.05% Triton X-100). In certain embodiments, a stable modified ceramide-like glycolipid is covalently bound to CD1d and the complex is able to retain at least about 75% NKT cell-stimulating activity after an in vitro incubation at room temperature for about 2 or about 3 days.

The modified glycolipid is able to physically associate with a protein, e.g., CD1d, through covalent interactions. "Modified glycolipid complex" or "modified glycolipid/protein complex", as referred to herein include modified glycolipids that are physically associated with a protein, such as CD1d. As used herein, the term "physically associated" refers to an interaction between two molecules wherein the two molecules are bonded to each other directly or indirectly (e.g., via intervening molecules) either through covalent or non-covalent interactions (e.g., hydrogen bonds, ionic bonds, van der Waals forces, hydrophobic interactions). In some embodiments, the modified glycolipid/protein complex comprises a modified glycoprotein that is covalently bound to the protein through the functional group of the modified glycoprotein that allows for the covalent interaction (e.g., a benzophenone group). The modified glycolipids of the invention can be physically associated with (e.g., covalently bound to) any protein. In some embodiments, the modified glycolipid (e.g., modified ceramide-like glycolipid) is physically associated with (e.g., covalently bound to) CD1d. A modified glycolipid/protein complex wherein the protein is CD1d is referred to herein as a "modified glycolipid/CD1d complex".

As used herein, the term "CD1d protein" encompasses a full-length CD1d protein, fragments, or variants thereof that are capable of binding to a glycolipid and β2-microglobulin or a fragment or variant thereof. The CD1d molecule is a member of the family of major histocompatibility complex antigen-like glycoproteins which associate with $\beta_2$-microglobulin and are expressed at the surface of cortical thymocytes, B cells, dendritic cells, Langerhans cells in the skin, and gastrointestinal epithelial cells. CD1d is mainly expressed on dendritic cells or epithelial cells of the gastrointestinal tract. The CD1 family members are involved in the presentation of glycolipids as antigens. In particular, CD1d regulates cytokine tone through activation of a distinct subset of T-lymphocytes, namely NK1 T cells which secrete IL-4 and INF-γ. All of the CD1 glycoproteins have been cloned and analyzed. For a detailed discussion of CD1 glycoproteins, and in particular CD1d, see, e.g., Balk et al., *Proc. Natl. Acad. Sci. USA* 86:252-256 (1989); Kojo et al., *Biochem. Biophy. Res. Comm.* 276:107-111 (2000); Kojo et al., *J. Rheumatology* 30:2524-2528 (2003); Kang and Cresswell, *Nature Immunology* 5:175-181 (2004); Im et al., *J. Biol. Chem.* 279:299-310 (2004); Dutronc and Porcelli, *Tissue Antigens* 60:337-353 (2002) which are incorporated by reference herein in their entirety.

Full-length CD1d consists of a signal sequence, an extracellular domain, a transmembrane domain and a cytoplasmic domain. The full-length CD1d polypeptide is 335 amino acids in length.

The human CD1d sequence is known in the art and has the accession number NP_001757 in Genbank, which is set forth in SEQ ID NO: 1.

A variant of human CD1d includes, but is not limited to, a polypeptide with the following mutation: T64S.

The sequence of mouse CD1d can be found on Genbank with the following accession number: NP_031665. The sequence of rat CD1d can be found on Genbank with the following accession number: NP_058775. The sequence of sheep CD1d can be found on Genbank with the following accession numbers: O62848 and Q29422. The sequence of chimpanzee CD1d can be found on Genbank with the following accession number: NP_001065272. The sequence of rabbit CD1d can be found on Genbank with the following accession number: P23043.

The extracellular domain of CD1d consists of three domains: the α1 domain, the α2 domain, and the α3 domain. The α1 and α2 domains comprise the antigen binding sites. The α3 domain includes a $\beta_2$-microglobulin association site.

The CD1d domain designations used herein are defined as in Table 2.

TABLE 2

| CD1d domains | |
| --- | --- |
| Domain | CD1d (human) |
| Signal Seq. | 1-19 |
| Extracellular | 20-301 |
| α1 domain | 20-108 |
| α2 domain | 109-201 |
| α3 domain | 202-295 |
| Transmembrane | 302-322 |
| Cytoplasmic | 323-335 |

As one of skill in the art will appreciate, the beginning and ending residues of the domains listed above may vary depending upon the computer modeling program used or the method used for determining the domain.

Some embodiments of the invention provide a modified glycolipid/CD1d complex, which comprises a soluble CD1d polypeptide. Table 1 above describes the various domains of the CD1d polypeptide. Soluble CD1d polypeptides generally comprise a portion or all of the extracellular domain of the polypeptides, including the α1, α2, and α3 domains. Soluble CD1d polypeptides generally lack some or all of the transmembrane domain and cytoplasmic domain. As one of skill in the art would appreciate, the entire extracellular domain of CD1d may comprise additional or fewer amino acids on either the C-terminal or N-terminal end of the extracellular domain polypeptide.

CD1d polypeptides for use in the methods and compositions of the present invention include, but are not limited to, a CD1d polypeptide comprising, consisting essentially of, or consisting of an amino acid sequence identical to a reference amino acid sequence, except for up to twenty amino acid substitutions. In some embodiments, the reference amino acid sequence is selected from the group consisting of amino acids a to 295 of SEQ ID NO:1, amino acids 21 to b of SEQ ID NO:1, and a to b of SEQ ID NO:1, wherein a is any integer from 1 to 100, and b is any integer from 201 to 301, and wherein the CD1d polypeptide associates with $\beta_2$-microglobulin and binds a ceramide-like glycolipid. In one embodiment, the soluble CD1d polypeptide comprises amino acids 21 to 295 of SEQ ID NO:1. In another embodiment, the soluble CD1d polypeptide comprises amino acids 20-295, 20-296, 20-297, 20-298, 20-299, 20-300 and 20 to 301 of SEQ ID NO:1.

For the purposes of the presently disclosed methods and compositions, in those embodiments wherein the modified glycolipid/protein complex comprises a CD1d protein, the complex further comprises a β2-microglobulin physically associated (e.g., covalently bound) with the CD1d protein. In some of these embodiments, the β2-microglobulin is covalently linked to the amino terminus of CD1d.

In certain embodiments, a CD1d complex of the invention comprises a $\beta_2$-microglobulin polypeptide, which associates with a soluble CD1d polypeptide or polypeptide fragment. $\beta_2$-microglobulin is present on the surface of all nucleated cells as the small extracellular subunit of the major histocompatibility complex (MHC) class I molecule and actively participates in the immune response. For a detailed discussion of $\beta_2$-microglobulin, see, e.g., Peterson et al., *Adv. Cancer Res.* 24:115-163 (1977); Sege et al., *Biochemistry* 20:4523-4530 (1981); which are incorporated by reference herein in their entirety.

Full-length $\beta_2$-microglobulin is a secreted protein which comprises a signal sequence and Ig-like domain. The full-length CD1d polypeptide is 119 amino acids in length.

The human $\beta_2$-microglobulin sequence is known in the art and has the accession number NP_004039 in Genbank, which is set forth herein as SEQ ID NO: 2.

Variants of human $\beta_2$-microglobulin include, but are not limited to, polypeptides with one or more of the following mutations: A20G, P52Q, S55V, and Y86YS.

The sequence of mouse $\beta_2$-microglobulin can be found on Genbank with the following accession number: NP_033865. The sequence of pig $\beta_2$-microglobulin can be found on Genbank with the following accession number: NP_999143. The sequence of rat $\beta_2$-microglobulin can be found on Genbank with the following accession number: NP_036644. The sequence of chimpanzee $\beta_2$-microglobulin can be found on Genbank with the following accession number: NP_001009066. The sequence of rabbit $\beta_2$-microglobulin can be found on Genbank with the following accession number: P01885. The sequence of sheep $\beta_2$-microglobulin can be found on Genbank with the following accession number: NP_001009284. All of the above Genbank accession numbers are incorporated herein by reference.

The $\beta_2$-microglobulin domain designations used herein are defined as in Table 3.

TABLE 3

| Domain | $\beta_2$-microglobulin (human) |
|---|---|
| Signal Seq. | 1-20 |
| $\beta_2$-microglobulin | 21-119 |
| Ig domain | 25-113 22-116 |

$\beta_2$-microglobulin domains

As one of skill in the art will appreciate, the beginning and ending residues of the domains listed above may vary depending upon the computer modeling program used or the method used for determining the domain.

Modified glycolipid/CD1d complexes of the invention may comprise fragments, variants, or derivative thereof of a $\beta_2$-microglobulin polypeptide. Table 3 above describes the various domains of the $\beta_2$-microglobulin polypeptide. $\beta_2$-microglobulin polypeptides of the invention generally comprise a portion or all of the secreted portion of the polypeptides.

Human $\beta_2$-microglobulin polypeptides for use in the methods of the present invention include, but are not limited to, a $\beta_2$-microglobulin polypeptide comprising, consisting essentially of, or consisting of an amino acid sequence identical to a reference amino acid sequence (e.g., SEQ ID NO: 2), except for up to twenty amino acid substitutions. In some embodiments, the reference amino acid sequence is selected from the group consisting of amino acids a to 119 of SEQ ID NO:2, amino acids 21 to b of SEQ ID NO: 2, and a to b of SEQ ID NO:2, wherein a is any integer from 15 to 25, and b is any integer from 100 to 119, wherein said $\beta_2$-microglobulin polypeptide associates with CD1d and supports binding of ceramide-like glycolipids. In one embodiment, the $\beta_2$-microglobulin polypeptide comprises amino acids 21 to 113 of SEQ ID NO:2. In one embodiment, the $\beta_2$-microglobulin polypeptide comprises amino acids 21 to 119 of SEQ ID NO:2.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

CD1d or β2-microglobulin polypeptides described herein may have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of CD1d or β2-microglobulin polypeptides at least 70%, 75%, 80%, 85%, 90%, or 95% identical to the polypeptides and reference polypeptides described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

A soluble CD1d polypeptide may contain some or all of the amino acids from the transmembrane domain, provided that the polypeptide is still capable of remaining soluble in an aqueous, e.g., a physiological solution. Preferably, not more than about 20, 19, 18, 17, 16, 15, 14, 13, 12, 11, 10, 9, 8, 7, 6, 5, 4, 3, 2 or 1, and preferably none of the amino acids of the transmembrane domain will be included.

Additionally, fragments of $\beta_2$-microglobulin are useful in the present invention. To be useful in the present invention, the fragment of $\beta_2$-microglobulin would have to retain the ability to associate with the CD1d molecule. Preferably, not more than about 20, 19, 18, 17, 16, 15, 14, 13, 12, 11, 10, 9, 8, 7, 6, 5, 4, 3, 2 or 1, and preferably none of the amino acids of $\beta_2$-microglobulin will be deleted.

One may wish to introduce a small number of amino acids at the polypeptide termini of either the soluble CD1d polypeptide or the $\beta_2$-microglobulin polypeptide, usually not more than 20, 19, 18, 17, 16, 15, 14, 13, 12, 11, 10, 9, 8, 7, 6, 5, 4, 3, 2 or 1. The deletion or insertion of amino acids will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about 10, 9, 8, 7, 6, 5, 4, 3, 2 or 1 amino acids in any one domain.

The CD1d and β2-microglobulin may be autologous to any mammalian or avian species, for example, primates (esp. humans), rodents, rabbits, equines, bovines, canines, felines, etc. β2-microglobulin is typically not inflammatory in vivo. However, it is preferable to employ β2-microglobulin derived from the same species as is to be administered the modified glycolipid/CD1d complex so as to reduce the risk of a xenogeneic immune response.

The soluble CD1d polypeptide and $\beta_2$-microglobulin polypeptide may be separately produced and allowed to associate to form a stable heteroduplex complex, or both of the subunits may be expressed in a single cell.

Soluble CD1d polypeptides and $\beta_2$-microglobulin polypeptides for use in the methods and compositions of the present invention may be isolated from a multiplicity of cells, e.g., transformed cell lines JY, BM92, WIN, MOC, and MG, and CHO using a variety of techniques known to those skilled in the art. It is also possible to construct a functional fusion molecule in which the carboxyl terminus of $\beta_2$-microglobulin or a fragment thereof is connected through a linker to the amino terminus of CD1d or a fragment thereof.

Additionally, the amino acid sequences of CD1d and β2-microglobulin from a variety of species are known, and the polynucleotides encoding these polypeptides have been cloned, therefore, the polypeptides can be made using recombinant methods. The coding regions for the CD1d and $\beta_2$ microglobulin chains or their fusion products are inserted into expression vectors, expressed separately in an appropriate host, such as *E. coli*, yeast, insect cells, mammalian cells or other suitable cells.

The term "vaccine" refers to a composition, which when administered to an animal is useful in stimulating an immune response, e.g., against an antigen, e.g., a heterologous antigen. As used herein, a "heterologous" antigen is an antigen that originates from a foreign species, or, if from the same species, is substantially modified from its native form in composition by deliberate human intervention.

In certain embodiments, a modified glycolipid complex may be administered with a heterologous antigen or a targeting molecule. In other embodiments, a modified glycolipid/protein complex of the invention is used as an "antigen carrier" for the delivery of a heterologous antigen, e.g., an immunogenic polypeptide, or a targeting molecule. For example, a modified glycolipid/protein complex can be used as an antigen carrier for the delivery of antigens from another pathogen (e.g., bacterial (e.g., *Salmonella, Listeria, Bacillus anthracis*, and *Shigella* antigens), fungal, parasitic (e.g., a malarial antigen from *Plasmodium*), or viral antigens (e.g., a viral antigen from HIV, SIV, HPV, RSV, influenza or hepatitis (HAV, HBV, and HCV)) or tumor specific antigens.

Compositions of the invention include cells (e.g., viral, fungal, bacterial cells) physically associated with a modified glycolipid. As described in U.S. Application Publication No. 2010/0183549, which is herein incorporated by reference in its entirety, glycolipids, such as ceramide-like glycolipids can be physically associated with bacterial cells by culturing the bacterial cells with the glycolipid. Thus, in some embodiments, the modified glycolipid can be physically associated with a bacterial cell by first culturing the bacterial cell with a modified glycolipid comprising a photoreactive group to allow for association of the modified glycolipid with the cell wall of the bacterial cell, followed by irradiation with a light source (e.g., ultraviolet light) to allow for covalent linkage of the modified glycolipid to the surface of the bacterial cell.

In some embodiments, the modified glycolipid/protein complexes of the invention comprise a targeting molecule (e.g., an antibody, including but not limited to a monoclonal, chimeric, humanized, human, bifunctional antibody, or antigen-binding fragment thereof, such as, for example, Fab and F(ab')2 portions and Fv fragments, and single-chain antibodies) that serves to target the complex to a particular cell, tissue, organ, or region of a subject's body. In some of these embodiments, the targeting molecule is an antibody or an antigen-binding fragment that specifically binds to a target antigen, such as a cell surface marker, as taught in U.S. Application Publication No. 2006/0269540, which is herein incorporated by reference in its entirety. The protein (e.g., CD1d) may be directly linked or fused to the targeting molecule (e.g., antibody or antigen-binding fragment thereof), either directly or through a linker sequence or molecule. In certain embodiments, the protein (e.g., CD1d) is linked to the targeting molecule (e.g., antibody or fragment thereof) through a multivalent compound.

In those embodiments wherein the protein is CD1d, the targeting molecule can either be linked to the CD1d molecule or the β2 microglobulin. In those embodiments wherein the targeting molecule is an antibody, the protein (e.g., CD1d or β2 microglobulin) may be linked to either the light chain or the heavy chain of the antibody. As taught by International Application Publication No. WO 9964597 and incorporated herein by reference in its entirety, it is possible to introduce mutations into β2-microglobulin that increase affinity for the class I heavy chain so as to facilitate assembly and increase stability of the fusion protein.

The protein (e.g., CD1d or β2 microglobulin) may be linked to either the carboxyl or amino terminus of the antibody, or it may be linked to the antibody at a site other than the carboxyl or amino termini. In some embodiments wherein CD1d is the protein within the modified glycolipid/protein complex, the antibody or antigen-binding fragment thereof is linked to the carboxyl terminus of CD1d. In some of these embodiments, the amino terminus of a single chain Fv fragment (scFv) is linked to the carboxyl terminus of CD1d.

In one embodiment, the targeting molecule (e.g., antibody or antigen-binding fragment thereof) is specific for a cell surface marker of a tumor cell. In some embodiments of the present invention, the cancer is a head and neck cancer, gastric cancer, esophageal cancer, stomach cancer, colorectal cancer, colon carcinoma, cancer of liver and intrahepatic bile ducts, pancreatic cancer, lung cancer, small cell lung cancer, cancer of the larynx, breast cancer, malignant melanoma, multiple myeloma, sarcomas, rhabdomyosarcoma, lymphomas, follicular non-Hodgkin-lymphoma, leukemias, T- and B-cell-leukemias, Hodgkin-lymphoma, B-cell lymphoma, ovarian cancer, cancer of the uterus, cervical cancer, prostate cancer, genital cancer, renal cancer, cancer of the testis, thyroid cancer, bladder cancer, plasmacytoma or brain cancer.

Tumor associated antigens comprise pan-carcinoma antigens like CEA (Sundblad Hum. Pathol. 27, (1996) 297-301, Ilantzis Lab. Invest. 76 (1997), 703-16), EGFR type I (Nouri, Int. J. Mol. Med. 6 (2000), 495-500) and EpCAM (17-1A/KSA/GA733-2, Balzar J. Mol. Med. 77 (1999), 699-712). EGFR type I is especially overexpressed in glioma and EpCAM in colon carcinoma. EGFR type II (Her-2/neu, ERBB2 Sugano Int. J. Cancer 89 (2000), 329-36) and TAG-72 glycoprotein (sTN antigen, Kathan Arch. Pathol. Lab. Med. 124 (2000), 234-9) are upregulated in breast cancer. EGFR deletion neoepitope might also play a role as tumor associated antigen (Sampson Proc. Natl. Acad. Sci. USA 97 (2000), 7503-8). The antigens A33 (Ritter Biochem. Biophys. Res. Commun. 236 (1997), 682-6), Lewis-Y (DiCarlo Oncol. Rep. 8 (2001), 387-92), Cora Antigen (CEA-related Cell Adhesion Molecule CEACAM 6, CD66c, NCA-90, Kinugasa Int. J. Cancer 76 (1998), 148-53) and MUC-1 (Mucin) are associated with colon carcinoma (Iida Oncol. Res. 10 (1998), 407-14). Thomsen-Friedenreich-antigen (TF, Gal1B-3GalNAca1-0-Thr/Ser) is not only found in colon carcinoma (Baldus Cancer 82 (1998), 1019-27) but also in breast cancer (Glinsky Cancer. Res. 60 (2000), 2584-8). Overexpression of Ly-6 (Eshel J. Biol. Chem. 275 (2000), 12833-40) and desmoglein 4 in head and neck cancer and of E-cadherin neoepitope in gastric carcinoma has been described (Fukudome Int. J. Cancer 88 (2000), 579-83). Prostate-specific membrane antigen (PSMA, Lapidus Prostate 45 (2000), 350-4), prostate stem cell antigen (PSCA, Gu Oncogene 191 (2000) 288-96) and STEAP (Hubert, Proc Natl Acad Sci USA 96 (1999), 14523-8) are associated with prostate cancer. The alpha and gamma subunit of the fetal type acetylcholine receptor (AChR) are specific immunohistochemical markers for rhabdomyosarcoma (RMS, Gattenlohner Diagn. Mol. Pathol. 3 (1998), 129-34).

Association of CD20 with follicular non-Hodgkin lymphoma (Yatabe Blood 95 (2000), 2253-61, Vose Oncology (Huntingt) 2 (2001) 141-7), of CD19 with B-cell lymphoma (Kroft Am. J. Clin. Pathol. 115 (2001), 385-95), of Wue-1 plasma cell antigen with multiple myeloma (Greiner Virchows Arch 437 (2000), 372-9), of CD22 with B cell leukemia (dArena Am. J. Hematol. 64 (2000), 275-81), of CD7 with T-cell leukemia (Porwit-MacDonald Leukemia 14 (2000), 816-25) and CD25 with certain T and B cell leukemias has been described (Wu Arch. Pathol. Lab. Med. 124 (2000), 1710-3). CD30 is associated with Hodgkin-lymphoma (Mir Blood 96 (2000), 4307-12). Expression of melanoma chondroitin sulfate proteoglycan (MCSP, Eisenmann Nat. Cell. Biol. 8 (1999), 507-13) and ganglioside GD3 is observed in melanoma (Welte Exp Dermatol 2 (1997), 64-9), while GD3 is also found in small cell lung cancer (SCLC, Brezicka Lung Cancer 1 (2000), 29-36). Expression of ganglioside GD2 is, also upregulated in SCLC and in neuroblastoma (Cheresh et al. Cancer Res. 10 (1986), 5112-8). Ovarian carcinoma is associated with Muellerian Inhibitory Substance (MIS) receptor type II (Masiakos Clin. Cancer Res. 11 (1999), 3488-99) and renal as well as cervical carcinoma with expression of carboanhydrase 9 (MN/CAIX, Grabmaier Int. J. Cancer 85 (2000) 865-70). Elevated expression levels of CA 19-9 were found in pancreatic cancer (Nazli Hepatogastroenterology 47 (2000), 1750-2).

Other examples of tumor cell surface antigens are Her2/neu, expressed in breast and ovarian carcinomas (Zhang, H. et al., *Experimental & Molecular Pathology* 67:15-25 (1999)); CM-1, expressed in breast cancer (Chen, L. et al., *Acta Academiae Medicinae Sinicae* 19(2):150-3); 28K2, expressed in lung adenocarcinoma and large cell carcinoma (Yoshinari, K. et al., *Lung Cancer* 25:95-103 (1999)); E48 and U 36 expressed in head and neck squamous cell carcinoma (Van Dongen, G. A. M. S. et al., *Anticancer Res.* 16:2409-14 (1996)); NY-ESO-1, expressed in esophageal carcinoma, and melanoma Jager, E. et al., *J. Exp. Med.* 187:265-70 (1998); Jager, E. et al., *International J. Cancer* 84:506-10 (1999)); KU-BL 1-5, expressed in bladder carcinoma (Ito, K. et al., *AUA* 2000 *Annual Meeting*, Abstract 3291 (2000)); NY CO 1-48, expressed in colon carcinoma (Scanlan, M. J. et al., *International J. Cancer* 76:652-8 (1998)); HOM MEL 40, expressed in melanoma (Tureci, O. et al., *Cancer Res.* 56:4766-72 (1996)); OV569, expressed in ovarian carcinoma (Scholler, N. et al., *Proc. Natl. Acad. Sci. USA* 96:11531-6 (1999)); ChCE7, expressed in neuroblastoma and renal cell carcinoma (Meli, M. L. et al., *International J. Cancer* 83:401-8 (1999)); CA19-9, expressed in colon carcinoma (Han, J. S. et al., *Cancer* 76:195-200 (1995)); CA125, expressed in ovarian carcinoma (O'Brien, T. J. et al., *International J. Biological Markers* 13:188-95 (1998)); and Gangliosides (GM2, GD2,9-o-acetyl-GD3, GD3), expressed in melanoma and neuroblastoma (Zhang, S. et al., *Cancer Immunol. Immunotherapy* 40:88-94 (1995)).

In particular embodiments of the presently disclosed methods, the tumor-associated antigen is selected from the group consisting of Lewis Y, CEA, Muc-1, erbB-2, -3 and -4, EpCAM, E-cadherin neoepitope, EGF-receptor (e.g. EGFR type I or EGFR type II), EGFR deletion neoepitope, CA19-9, Muc-1, LeY, TF-, Tn- and sTn-antigen, TAG-72, PSMA, STEAP, Cora antigen, CD7, CD19 and CD20, CD22, CD25, Ig-a and Ig-B, A33 and G250, CD30, MCSP and gp100, CD44-v6, MT-MMPS, (MIS) receptor type II, carboanhydrase 9, F19-antigen, Ly6, desmoglein 4, PSCA, Wue-1, TM4SF-antigens (CD63, L6, CO-29, SAS), the alpha and gamma subunit of the fetal type acetylcholine receptor (AChR), CM-1, 28K2, E48, U36, NY-ESO-1, KU-BL 1-5, NY CO 1-48, HOM MEL 40, OV569, ChCE7, CA19-9, CA125, GM2, GD2,9-o-acetyl-GD3, and GD3.

In another embodiment, the targeting molecule (e.g., antibody or antigen-binding fragment thereof) is specific for a cell surface marker of CD1d-restricted NKT cells. Non-limiting examples of suitable NKT cell markers to which to target specific antibodies are CD161, CD56, or (for NKT subsets) CCR4 on CD4+ CD1d-restricted NKT or CCR1 or CCR6 on double negative (CD4 and CD8 negative) CD1d-restricted NKT. This is particularly useful in treating diseases or symptoms which are the result of low NKT activity such as cancer or infection. In addition, since NKT cell activity is differentially modulated depending on the particular ceramide-like glycolipid bound to CD1d (see, e.g., U.S. Pat. No. 7,772,380, which is herein incorporated by reference in its entirety), compositions of the present invention include embodiments with selective association of CD1d with these functionally different ceramide-like glycolipids and the related α-glycosylceramides which may modulate diseases which are a result of high or deleterious NKT activity (e.g. excessive Th1 activity) such as myasthenia gravis (Reinhardt et al. Neurology 52:1485-87, 1999), psoriasis (Bonish, J. Immunol. 165:4076-85, 2000), ulcerative colitis (Saubermann et al. Gastroenterology 119:119-128, 2000), and primary biliary cirrhosis (Kita et al. Gastroenterology 123:1031-43, 2002).

In another embodiment, the targeting molecule (e.g., antibody or antigen-binding fragment thereof) is specific for a cell surface marker of a target tissue of autoimmune disease or inflammatory response. In a preferred embodiment, the modified glycolipid/CD1d complex is targeted to such sites by coupling the complex to a targeting molecule (e.g., an antibody or antigen binding-fragment thereof) specific for a local tissue antigen. The modified glycolipid/CD1d complex concentrated on local tissue cells will then lead to recruitment and activation of CD1d-restricted NKT cells and trigger a cascade of events that regulate the autoimmune or inflammatory response. The relevant specific tissue antigens may be different for different autoimmune and inflammatory diseases.

In the case of demyelinating diseases including, most especially, multiple sclerosis, the targeting molecule (e.g., antibody or antigen-binding fragment thereof) is specific for MBP (myelin basic protein), PLP (myelin proteolipid protein), or MOG (myelin oligodendrocyte glycoprotein). In particular embodiments, the targeting molecule (e.g., antibody or antigen-binding fragment thereof) is specific for MOG.

In the case of juvenile onset type I diabetes which follows from destruction of insulin-producing pancreatic islet beta cells, the targeting molecule (e.g., antibody or antigen-binding fragment thereof) is specific for target antigens of the islet beta cells such as GT3 ganglioside, IGRP (islet-specific glucose-6-phosphatase related protein), or SUR1 (Proks P et al., Diabetes: 51 Suppl 3:S368-76, 2002). Recently, peri-islet Schwann cells have been described as an early target of autoimmune destruction in this disease (Winer S et al: Nature Medicine 9:198-205, 2003). In another preferred embodiment of the invention, therefore, the targeting molecule (e.g., antibody or antigen-binding fragment thereof) is specific for Schwann cell specific antigens glial fibrillary acidic protein (GFAP), and S100beta for treatment or diagnosis of juvenile onset type I diabetes.

In other embodiments of the presently disclosed methods for treatment of autoimmune and inflammatory diseases, conjugates comprising modified glycolipid/CD1d complexes and targeting molecules (e.g., antibodies or antigen-binding fragment thereof) specific for type II collagen are injected into affected joints for treatment of rheumatoid arthritis; targeting molecules specific for thyroglobulin or TSH receptor are targeted to the thyroid for treatment of Hashimoto's thyroiditis and Graves' disease; and targeting molecules specific for the K+/H+ ATPase are employed for treatment of pernicious anemia or atrophic gastritis (targeting the gastric parietal cells).

In other embodiments, the targeting molecule (e.g., antibody or antigen-binding fragment thereof) is specific for a cell surface marker of an infected cell or tissue. In a preferred embodiment, a modified glycolipid/CD1d complex is targeted to the site of infection by coupling the complex to a targeting molecule (e.g., antibody or antigen-binding fragment thereof) specific for an antigen encoded by the infectious agent. The relevant antigens are different in the case of different infectious agents. In particular embodiments of the presently disclosed methods, the surface marker for an infected cell is selected from the group consisting of viral envelope antigens, e.g. of human retroviruses (HTLV I and II, HIV1 and 2) or human herpes viruses (HSV1 and 2, CMV, EBV), haemagglutinin e.g. of influenza virus (influenza A, B or C), glycoproteins E1 and E2 from rubella virus or RGP of rabies virus.

In other embodiments, the targeting molecule is specific for antigens encoded by other infectious viruses, bacteria, fungi, protozoa or helminthes.

In one embodiment, the targeting molecule (e.g., antibody or antigen-binding fragment thereof) is specific for a cell surface marker of a professional antigen presenting cell. In some of these embodiments, the targeting molecule is specific for a cell surface marker of a dendritic cell, for example, CD83, DEC205, CMRF-44 (Fearnley D B et al. Blood 89:3708-16, 1997), CMRF-56 (Hock B D et al. Tissue Antigens 53:320-34, 1999), BDCA-1, BDCA-2, BDCA-3, and BDCA-4 (Dzionek A et al. J. Immunol. 165:6037-6046, 2000). In other embodiments, the targeting molecule is specific for markers of antigen presenting cells including Toll-like receptors (TLR1, TLR2, TLR3, TLR4, TLR5, TLR7, TLR9) mannose receptor, and mannan-binding lectin (MBL); as well as additional markers specific to dendritic cells, including, DC-SIGN (the C-type lectin, non-integrin, ICAM-3 receptor on DC), ALCAM, DC-LAMP, and any of a number of other receptors for apoptotic cells including phosphatidylserine receptor. The targeting molecule may be specific for a cell surface marker of another professional antigen presenting cell, such as a B cell or a macrophage. CD19, CD20 and CD22 are expressed on B cells, and other markers have been described for other antigen presenting cells.

In other embodiments, the targeting molecule (e.g., antibody or antigen-binding fragment thereof) is specific for a cell surface marker of a dendritic cell subset. In a particular embodiment of the invention, a modified glycolipid/CD1d complex is targeted to DC by coupling the complex to a targeting molecule specific for a surface antigen marker of DC such as CD83, DEC205, CMRF-44, CMRF-56, DC-SIGN, Toll-like Receptors (TLR) including TLR1, TLR2, TLR3, TLR4, TLR5, TLR7, TLR9, mannose receptor, mannan-binding lectin (MBL), ALCAM, DC-LAMP, phosphatidylserine receptor, BDCA-1, BDCA-2, BDCA-3 or BDCA-4 (neuropilin, Tordjman R et al. Nature Immunol. 3:477-82, 2002).

The term "antigen" and the related term "antigenic" as used herein refer to a substance that binds specifically to an antibody or to a T-cell receptor.

The term "immunogen" and the related term "immunogenic" as used herein refer to the ability to induce an immune response, including an antibody and/or a cellular immune response in an animal, for example a mammal. It is likely that an immunogen will also be antigenic, but an "antigen," because of its size or conformation, may not necessarily be an "immunogen." An "immunogenic composition" induces an immune response in a subject, e.g., antibodies that specifically recognize one or more antigens, contained within that "immunogenic composition." In certain embodiments, the immunogenic composition of the invention comprises a modified glycolipid/CD1d complex and a heterologous antigen or a targeting molecule.

The term "immune response" is meant to include an activity of cells of the immune system in response to an antigen or immunogen. Such activities include, but are not limited to production of antibodies, cytotoxicity, lymphocyte proliferation, release of cytokines, inflammation, phagocytosis, antigen presentation, and the like. An immune response which is highly specific to a given antigen or immunogen, e.g., production of specific antibodies or production of specific T lymphocytes is referred to herein as an "adaptive immune response." An immune response which is not specific to a given antigen, e.g., release of cytokines by NK and NKT cells, is referred to herein as an "innate immune response." Examples of immune responses include an antibody response or a cellular, e.g., cytotoxic T-cell or NKT cell, response.

The terms "protective immune response" or "therapeutic immune response" refer to an immune response to an immunogen, which in some way prevents or at least partially arrests disease symptoms, side effects or progression. By "protective" is meant that the immune response is induced in a subject animal which has not contracted a disease, where the immune response alleviates, reduces, moderates or, in some cases fully prevents disease symptoms if the animal later contracts or is susceptible to that disease, e.g., exposure to *M. tuberculosis*. By "therapeutic" is meant that the immune response is induced in a subject animal which has the disease, e.g., a human with tuberculosis, where the immune response alleviates, reduces, moderates, or in some cases fully eliminates disease symptoms. In certain embodiments, the presently disclosed compositions are used to induce a therapeutic immune response in an animal, e.g., a human, having an infectious disease or cancer or an autoimmune or inflammatory disease.

The term "modulating an immune response" is meant to refer to any way in which a given immune response is increased, decreased, or changed by a composition or treatment relative to the immune response without that composition or treatment. For example, use of an adjuvant, e.g., a modified glycolipid/CD1d complex comprising a heterologous antigen or a targeting molecule of the invention, to increase an immune response to an antigen, e.g., the heterologous antigen, is considered modulation of that immune response. Decrease in an immune response, e.g., prevention of autoimmunity, is also a modulation. In addition, changing an immune response, e.g., from a primary TH2 response to a primary TH1 response or vice versa, is a modulation of an immune response. The present invention provides methods of modulating an immune response by administering to an animal a composition which comprises a modified glycolipid/protein complex (e.g., modified glycolipid/CD1d complex) and a heterologous antigen or a targeting molecule.

The present invention provides compositions and methods useful for enhancing both primary and secondary immune responses. In one aspect, the primary and/or secondary immune response is against a heterologous antigen or a targeting molecule that is administered together with, prior to, or soon after the modified glycolipid/protein complex of the invention (e.g., modified glycolipid/CD1d complex). In one aspect, the modified glycolipid/protein complex is used as an antigen carrier for delivery of antigens, e.g., heterologous antigens or targeting molecules that enhance an immune response against an infectious agent or tumor.

The term "adjuvant" refers to a material having the ability to (1) alter or increase the immune response to a particular antigen or (2) increase or aid an effect of a pharmacological agent. In certain embodiments, a ceramide-like glycolipid functions as an adjuvant upon simultaneous administration with a CD1d protein. In certain embodiments, the ceramide-like glycolipid, e.g., αGalCer or analog thereof, functions as an adjuvant when administered with a CD1d protein and heterologous antigen or a targeting molecule. In another embodiment, a second adjuvant is included. Other suitable adjuvants include, but are not limited to, LPS derivatives (e.g., monophosphoryl lipid A (MPL)), TLR9 agonists (e.g., CPG ODNS), TLR7/8 agonists (e.g., imiquimod), cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which can increase the expression, antigenicity or immunogenicity of an immunogen is a potential adjuvant. Other potential adjuvants of the invention include, but are not limited to: glycolipids; chemokines; compounds that induces the production of cytokines and chemokines; interferons; inert carriers, such as alum, bentonite, latex, and acrylic particles; pluronic block polymers, such as TiterMax® (block copolymer CRL-8941, squalene (a metabolizable oil) and a microparticulate silica stabilizer); depot formers, such as Freunds adjuvant; surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; non-ionic surfactants; poly(oxyethylene)-poly(oxypropylene) tri-block copolymers; mLT; MF59™; SAF; Ribi™ adjuvant system; trehalose dimycolate (TDM); cell wall skeleton (CWS); Detox™; QS21; Stimulon™; complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, and combinations of more than one adjuvant.

In certain embodiments, the adjuvant is a cytokine A composition of the present invention can comprise one or more cytokines, chemokines, or compounds that induce the production of cytokines and chemokines Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In certain embodiments, compositions of the invention further comprise another component, e.g., a polypeptide with immunological activity. For example, the protein with immunological activity is a costimulatory molecule, such as a toll-like receptor ("TLR"), B7.1 or B7.2. "B7" is used herein to generically refer to either B7.1 or B7.2. A costimulatory molecule, e.g., the extracellular domain of B7-1 (CD80) or B7-2 (CD86) that interacts with CD28 on T- and NK-cells can be administered as an amino terminal fusion to β2-microglobulin incorporated into the structure of a soluble CD1d complex for use in the present invention. See, e.g., WO 9964597, published 16 Dec. 1999. In certain embodiments, incorporation of a costimulatory molecule, e.g., a B7 signaling molecule, with the compositions of the invention allows more effective and prolonged activation of NKT cells by a modified glycolipid/CD1d complex of the invention.

In other embodiments, the compositions of the invention further comprise additional adjuvant components, e.g., any of the adjuvants described above, such as, LPS derivatives (e.g., MPL), TLR9 agonists (e.g., CPG ODNS), TLR7/8 agonists (e.g., imiquimod), cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, cationic lipids, and Toll-like receptor (TLR) agonists. Examples of TLR agonist adjuvants which can be effective, include, but are not limited to: N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., γ-interferon, α-interferon), interleukins (e.g IL-1, IL-2, IL-3, IL-4, IL-5, IL-6, IL-10, IL-12, IL-15, IL-18), saponins (e.g., QS21), monophosphoryl lipid A (MPL), 3 De-O-acylated monophosphoryl lipid A (3D-MPL), unmethylated CpG sequences, 1-methyl tryptophan, arginase inhibitors, cyclophosphamide, antibodies that block immunosuppressive functions (e.g., anti-CTLA4 antibodies), lipids (such as palmitic acid residues), tripalmitoyl-S-glycerylcystein lyseryl-serine ($P_3$CSS), and Freund's adjuvant. Alternatively or additionally, compositions of the present invention may further comprise a lymphokine or cytokine that modulates immune cell activation such as transforming growth factor (TGF, e.g., TGFα and TGFβ); a interferons (e.g. IFNα); β interferons (e.g. IFNβ); γ interferons (e.g. IFNγ) or lymphocyte function-associated protein, such as LFA-1 or LFA-3; or an intercellular adhesion molecule, such as ICAM-1 or ICAM-2.

Other adjuvant examples include compounds such as isatoribin and it derivatives (Anadys Pharmaceuticals) or imidazoquinolinamines, such as imiquimod and resiquimod (Dockrell & Kinghom, *J. Antimicrob. Chemother.*, 48:751-755 (2001) and Hemmi et al., *Nat. Immunol.*, 3:196-200 (2002), guanine ribonucleosides, such as C8-substituted or N7, C-8-disubstituted guanine ribonucleosides (Lee et al., *Proc. Natl. Acad. Sci. USA*, 100:6646-6651 (2003) and the compounds that are disclosed in Pat. Pub. Nos. JP-2005-089, 334; WO99/32122; WO98/01448 WO05/092893; and WO05/092892, and TLR-7 agonist SM360320 (9-benzyl-8-hydroxy-2-(2-methoxy-ethoxy)adenine) disclosed in Lee et al., *Proc Natl Acad Sci USA*, 103(6):1828-1833 (2006).

In addition to isatoribin, other TLR agonist adjuvants include 9-benzyl-8-hydroxy-2-(2-methoxyethoxy)adenine (SM360320) and Actilon™ (Coley Pharmaceutical Group, Inc.). Other adjuvants which can be used in conjunction with the composition of the present invention are disclosed in PCT Pub. No. WO 2005/000348, U.S. Pat. Pub. No. 2007/0292418, and U.S. Pat. Pub. No. 2007/0287664.

Compositions of the invention can further comprise an immunogenic polypeptide. In certain embodiments, a modified glycolipid/protein complex of the invention (e.g., modified glycolipid/CD1d complex) can be used as antigen carriers for the delivery of heterologous antigens, targeting molecules or immunogens. Heterologous antigens, targeting molecules or immunogens can include, but are not limited to, immunogenic polypeptides.

An "immunogenic polypeptide" is meant to encompass antigenic or immunogenic polypeptides, e.g., poly-amino acid materials having epitopes or combinations of epitopes. As used herein, an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self-polypeptides, for example, tumor-associated antigens.

Modified glycolipid complexes of the invention comprising antigenic or immunogenic polypeptides can be used to prevent or treat, e.g., cure, ameliorate, lessen the severity of, or prevent or reduce contagion of viral, bacterial, fungal, and parasitic infectious diseases, as well as to treat allergies and proliferative diseases such as cancer.

In addition, modified glycolipid/protein complexes of the invention comprising antigenic and immunogenic polypeptides can be used to prevent or treat, e.g., cure, ameliorate, or lessen the severity of cancer including, but not limited to, cancers of oral cavity and pharynx (e.g., tongue, mouth, pharynx), digestive system (e.g., esophagus, stomach, small intestine, colon, rectum, anus, anal canal, anorectum, liver, gallbladder, pancreas), respiratory system (e.g., larynx, lung), bones, joints, soft tissues (including heart), skin, melanoma, breast, reproductive organs (e.g., cervix, endometrium, ovary, vulva, vagina, prostate, testis, penis), urinary system (e.g., urinary bladder, kidney, ureter, and other urinary organs), eye, brain, endocrine system (e.g., thyroid and other endocrine), lymphoma (e.g., Hodgkin's disease, non-Hodgkin's lymphoma), multiple myeloma, leukemia (e.g., acute lymphocytic leukemia, chronic lymphocytic leukemia, acute myeloid leukemia, chronic myeloid leukemia).

Modified glycolipid/protein complexes of the invention comprising antigenic and immunogenic polypeptides can be used to prevent or treat, e.g., cure, ameliorate, or lessen the severity of a disease caused by an infectious agent, e.g., viral, bacterial, fungal, and parasitic agents.

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpes virus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, e.g., immunogenic polypeptides from *Bacillus anthracis*, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of parasitic antigenic and immunogenic polypeptides include, but are not limited to *Balantidium coli* polypeptides, *Entamoeba histolytica* polypeptides, *Fasciola hepatica* polypeptides, *Giardia lamblia* polypeptides, *Leishmania* polypeptides, and *Plasmodium* polypeptides (e.g., *Plasmodium falciparum* polypeptides).

Examples of fungal antigenic and immunogenic polypeptides include, but are not limited to, *Aspergillus* polypeptides, *Candida* polypeptides, *Coccidiodes immitis* or *C. posadasii* polypeptides, *Cryptococcus* polypeptides, *Histoplasma* polypeptides, *Pneumocystis* polypeptides, and *Paracoccidiodes* polypeptides.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), C35, HER2/neu, CD20, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Compositions of the invention can further comprise other therapeutic agents. Examples of therapeutic agents include, but are not limited to, antimetabolites, alkylating agents, anthracyclines, antibiotics, and anti-mitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antibiotics include dactinomycin (formerly actinomycin), bleomycin, mithramycin, and anthramycin (AMC). Antimitotic agents include vincristine and vinblastine (which are commonly referred to as vinca alkaloids). Other cytotoxic agents include procarbazine, hydroxyurea, asparaginase, corticosteroids, mitotane (O,P'-(DDD)), interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid. Analogs and homologs of such therapeutic agents are encompassed by the present invention.

A modified glycolipid/protein complex of the invention, e.g., a benzophenone modified glycolipid/CD1d complex, or a composition or a vaccine composition comprising the same can be labeled, so as to be directly detectable, or can be used in conjunction with secondary labeled immunoreagents which will specifically bind the compound, e.g., for detection or diagnostic purposes. Labels of interest can include dyes, enzymes, chemiluminescers, particles, radioisotopes, or other directly or indirectly detectable agent. Alternatively, a second stage label can be used, e.g. labeled antibody directed to one of the constituents of the compound of the invention.

Examples of suitable enzyme labels include, but are not limited to malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc., Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to glycolipids or polypeptides of the invention are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The ability of a composition of the present invention to modulate an immune response can be readily determined by an in vitro assay. NKT cells for use in the assays include transformed NKT cell lines, or NKT cells which are isolated from a mammal, e.g., from a human or from a rodent such as a mouse. NKT cells can be isolated from a mammal by sorting cells that bind CD1d:α-GalCer tetramers. See, for example, Benlagha et al., *J Exp Med* 191:1895-1903 (2000); Matsuda et al., *J Exp Med* 192:741-754 (2000); and Karadimitris et al., *Proc Natl Acad Sci USA* 98:3294-3298 (2001). A suitable assay to determine if a compound or composition of the present invention is capable of modulating the activity of NKT cells is conducted by co-culturing NKT cells and antigen presenting cells, adding the particular compound or composition of interest to the culture medium that targets either the antigen presenting cells or the NKT cells directly, and measuring IL-4 or IFN-γ production. A significant increase or decrease in IL-4 or IFN-γ production over the same co-culture of cells in the absence of the compound or composition of the invention indicates stimulation or inhibition of NKT cells.

The NKT cells employed in the assays are incubated under conditions suitable for proliferation. For example, an NKT cell hybridoma is suitably incubated at about 37° C. and 5% CO2 in complete culture medium (RPMI 1640 supplemented with 10% FBS, penicillin/streptomycin, L-glutamine and $5 \times 10^{-5}$ M 2-mercaptoethanol). Serial dilutions of the compound can be added to the NKT cell culture medium. Suitable concentrations of the compound added to the NKT cells typically will be in the range of from $10^{-12}$ to $10^{-6}$ M. Use of antigen dose and APC numbers giving slightly submaximal NKT cell activation can be used to detect stimulation or inhibition of NKT cell responses by the compounds of the invention.

Alternatively, rather than measurement of an expressed protein such as IL-4 or IFN-γ, modulation of NKT cell activation can be determined by changes in antigen-dependent T cell proliferation as measured by radiolabelling techniques as are recognized in the art. For example, a labeled (e.g., tritiated) nucleotide can be introduced to an assay culture medium. Incorporation of such a tagged nucleotide into DNA serves as a measure of T cell proliferation. This assay is not suitable for NKT cells that do not require antigen presentation for growth, e.g., NKT cell hybridomas. A difference in the level of T cell proliferation following contact with the compound or composition of the invention indicates the complex modulates activity of the T cells. For example, a decrease in NKT cell proliferation indicates the compound or composition can suppress an immune response. An increase in NKT cell proliferation indicates the compound or composition can stimulate an immune response.

Additionally, the $^{51}$Cr release assay can be used to determine cytotoxic activity.

These in vitro assays can be employed to select and identify modified glycolipids and modified glycolipid/protein complexes and compositions comprising same that are capable of appropriately modulating an immune response. Assays described above, e.g., measurement of IL-4 or IFN-γ production or NKT cell proliferation, are employed to determine if contact with the compound modulates T cell activation.

In addition or alternatively, immunization challenge experiments in animals, e.g., mice, rabbits, non-human primates, can be used to identify modified glycolipids and modified glycolipid/protein complexes and compositions comprising same that are capable of appropriately modulating an immune response and that may be efficacious for treatment and/or prevention of bacterial diseases, e.g., tuberculosis, in humans.

A modified glycolipid and modified glycolipid/protein complex, composition, or vaccine composition of the present invention can be used both to prevent a disease, and also to therapeutically treat a disease, e.g., a viral disease, a bacterial disease, a fungal disease, a parasitic disease, an allergic disease, or a proliferative disease, e.g., cancer, or an autoimmune or inflammatory disease. In individuals already suffering from a disease, the present invention is used to further stimulate or modulate the immune system of the animal, thus reducing or eliminating the symptoms associated with that disease or disorder. As defined herein, "treatment" refers to the use of one or more modified bacteria, compositions, or vaccine compositions of the present invention to prevent, cure, retard, or reduce the severity of given disease symptoms in an animal, and/or result in no worsening of the disease over a specified period of time in an animal which has already contracted the disease and is thus in need of therapy.

The term "prevention" or "prevent" refers to the use of one or more modified glycolipids, modified glycolipid/protein complexes, compositions, or vaccine compositions of the present invention to generate immunity in an animal which has not yet contracted a disease, thereby preventing or reducing disease symptoms if the animal is later disposed to develop that disease. The methods of the present invention therefore can be referred to as therapeutic methods or preventative or prophylactic methods. It is not required that any modified glycolipid, modified glycolipid/protein complex, composition, or vaccine composition of the present invention provide total immunity to a disease agent or totally cure or eliminate all disease symptoms.

As used herein, a "subject in need of therapeutic and/or preventative immunity" refers to an individual for whom it is desirable to treat, i.e., to prevent, cure, retard, or reduce the severity of certain disease symptoms, and/or result in no worsening of disease over a specified period of time.

An "effective amount" is that amount the administration of which to an individual, either in a single dose or as part of a series, is effective for treatment and/or prevention. An amount is effective, for example, when its administration results in a reduced incidence or severity of disease symptoms associated with *M. tuberculosis* relative to an untreated individual, as determined about two weeks after challenge with infectious *M. tuberculosis*. This amount varies depending upon the health and physical condition of the individual to be treated, the taxonomic group of individual to be treated (e.g. human, nonhuman primate, primate, etc.), the responsive capacity of the individual's immune system, the degree of protection desired, the formulation of the vaccine, a professional assessment of the medical situation, and other relevant factors. It is expected that the effective amount will fall in a relatively broad range that can be determined through routine trials.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The invention provides methods of preventing or treating a disease in a subject in need of such treatment or prevention, comprising administering to the subject with that disease, or prone to contract that disease, a composition comprising a modified glycolipid or a modified glycolipid/protein complex, such as a modified ceramide-like glycolipid/CD1d complex as described herein. In further embodiments, the protein of the modified glycolipid/protein complex can be used as an antigen carrier for delivery of heterologous antigens or targeting molecules for a pathogen or a tumor specific antigen.

The present invention also includes a method of modulating, i.e., either stimulating or inhibiting an immune response, comprising administering to an animal an effective amount of a modified glycolipid or a modified glycolipid/protein complex, such as a modified ceramide-like glycolipid/CD1d complex as described herein. In further embodiments, the composition further comprises a heterologous antigen or a targeting molecule from another pathogen or a tumor specific antigen, and the immune response is a priming immune response against the heterologous antigen or a targeting molecule.

In certain embodiments, the methods of the invention include treating a disease, e.g., an infectious or proliferative disease, in a subject with the disease by administering to the subject with the disease a composition of the invention, e.g., a modified glycolipid/CD1d complex of the invention, in an amount sufficient to alter the progression of said disease.

In other embodiments, the methods of the invention include preventing a disease, e.g., an infectious or proliferative disease, in a subject in need of prevention of the disease by administering to the subject in need thereof a composition of the invention, e.g., a modified glycolipid/CD1d complex of the invention, in an amount sufficient to enhance an immune response against an antigen relative to administration of an unmodified glycolipid/CD1d complex (e.g., one lacking a photoreactive group).

In further embodiments, the disease being treated or prevented can be, without limitation a viral, bacterial, fungal, or parasitic infectious disease, an allergy or a proliferative disease such as cancer or an autoimmune or inflammatory disease such as multiple sclerosis, diabetes, or Sjogren's Syndrome. More specifically, the disease can be, e.g., tuberculosis, Hansen's disease, pulmonary disease resembling tuberculosis, lymphadenitis, skin disease, disseminated disease, bubonic plague, pneumonic plague, tularemia, Legionnaire's disease, anthrax, typhoid fever, paratyphoid fever, foodborne illness, listeriosis, malaria, HIV, SIV, HPV, RSV, influenza, hepatitis (HAV, HBV, and HCV).

In another embodiment, the methods of the invention include enhancing an immune response in a subject, comprising administering to the subject a modified glycolipid or modified glycolipid/protein complex of the invention (e.g., modified ceramide-like glycolipid/CD1d complex); and wherein the modified glycolipid or modified glycolipid/protein complex is administered in an amount sufficient to enhance antigen specific CD8 T-cell responses against an antigen and enhance the activity of Natural Killer T (NKT) cells in said animal.

As used herein, a "subject in need thereof" refers to an individual for whom it is desirable to treat, i.e., to prevent, cure, retard, or reduce the severity of the symptoms of a disease, e.g., a bacterial infection, and/or result in no worsening of a disease over a specified period of time.

According to these methods, a modified glycolipid or modified glycolipid/protein complex (e.g., modified ceramide-like glycolipid/CD1d complex), composition, or vaccine composition of the present invention can be administered in an amount sufficient to alter the progression of a disease.

"Immunization" (administration of a vaccine) is a common and widespread procedure and the vaccines of the invention used can be essentially any preparation intended for active immunological prophylaxis, including without limitation preparations of killed microbes of virulent strains and living microbes of attenuated strains. Stedman's Illustrated Medical Dictionary (24th edition), Williams & Wilkins, Baltimore, p. 1526 (1982). In some cases, vaccines must be administered more than once in order to induce effective protection; for example, known anti-toxin vaccines must be given in multiple doses.

The terms "priming" or "primary" and "boost" or "boosting" as used herein refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously. See also, McShane H, *Curr Opin Mol Ther* 4(1):13-4 (2002) and Xing Z and Charters T J, *Expert Rev Vaccines* 6(4):539-46 (2007), both incorporated herein by reference.

In certain embodiments, one or more compositions of the present invention are utilized in a "prime boost" regimen. In certain embodiments, one or more vaccine compositions of the present invention are delivered to a vertebrate, thereby priming the immune response of the vertebrate to a bacterial antigen, e.g., a mycobacterial antigen, or a tumor antigen, and then a second immunogenic composition is utilized as a boost vaccination. In certain embodiments, one or more vaccine compositions of the present invention are delivered to a vertebrate, thereby priming the immune response of the vertebrate to a heterologous antigen or a targeting molecule, e.g., a heterologous antigen or a targeting molecule carried by a modified ceramide-like glycolipid/CD1d complex, and then a second immunogenic composition is utilized as a boost vaccination. In another embodiment, one or more vaccine compositions of the present invention are used to prime immunity, and then a second immunogenic composition, e.g., a recombinant bacterial or tumor vaccine, is used to boost the anti-bacterial or anti-tumor immune response. The vaccine compositions can comprise one or more vectors for expression of one or more genes that encode immunogenic polypeptides as described herein.

The present invention further provides a method for generating, enhancing, or modulating a protective and/or therapeutic immune response to a pathogen, e.g., a bacterial, fungal, viral, or parasitic pathogen, or a tumor antigen, in a vertebrate, comprising administering to a vertebrate in need of therapeutic and/or preventative immunity one or more of the modified glycolipids, modified glycolipid/protein complexes, compositions, or vaccine compositions described herein. In some of these embodiments, the composition includes a modified ceramide-like glycolipid/CD1d complex. In certain embodiments, the modified glycolipid/CD1d complex further comprises a heterologous antigen or a targeting molecule.

In certain embodiments, the modified glycolipids, modified glycolipid/protein complexes, composition, or vaccine composition of the invention can be used to reduce the dose required to obtain a favorable response to the vaccine. This would have the potential benefits of reducing local and systemic toxicity, thus increasing the safety profile of the vaccine. In addition, this could have the benefit of allowing for reduced cost of production.

Certain embodiments of the present invention include a method of reducing or eliminating the anergic response of NKT cells to multiple administrations of ceramide-like glycolipid antigens administered by themselves, for example, those which are presented to NKT cells in the context of a bacterial cell wall. It has been shown that multiple administrations of α-GalCer, administered by itself, causes NKT cells to become non-responsive for an extended period of time. The present invention, in which modified glycolipids such as α-GalCer are administered as part of a modified ceramide-like glycolipid/CD1d complex, may protect NKT cells from anergy in response to antigen, and allow for a prolonged response upon multiple administrations. Accordingly, NKT cells are activated in response to stimulation with modified ceramide-like glycolipid/CD1d complexes loaded with a modified ceramide-like glycolipid of the present invention and furthermore, NKT cells can be reactivated in response to restimulation by modified ceramide-like glycolipid/CD1d complexes loaded with a modified ceramide-like glycolipid of the present invention.

According to the methods of the present invention, a composition comprising a modified glycolipid or modified glycolipid/protein complex (e.g., ceramide-like glycolipid antigen/CD1d complex) as described herein is administered to modulate an immune response in an animal, e.g., a vertebrate, e.g., a mammal, e.g., a human. In certain embodiments, the methods of the present invention result in the enhancement of an immune response, e.g., to an immunogen delivered before, after, or concurrently with a modified glycolipid or modified glycolipid/protein complex (e.g., modified ceramide-like glycolipid/CD1d complex). Administration of a modified glycolipid or modified glycolipid/protein complex of the invention, e.g., with an immunogen, may typically result in the release of cytokines from immune cells, e.g., NKT cells or NK cells. Cytokines released in response to administration of a composition, or vaccine composition of the invention may be those associated with a TH1-type immune response, e.g., interferon gamma and TNF-alpha. Alternatively, or in addition, administration of a modified glycolipid, composition, or vaccine composition of the present invention may result in the release of cytokines associated with a TH2-type immune response, e.g., IL-4, IL-5, IL-10, or IL-13. Alternatively, or in addition, administration of a modified glycolipid, composition, or vaccine composition of the present invention may result in the release of other cytokines, e.g., IL-2, IL-1β, IL-12, IL-17, IL-23, TNF-β/LT, MCP-2, oncostatin-M, and RANTES. Methods to modulate the type of cytokines released include varying the ceramide-like glycolipid antigen of the ceramide-like glycolipid/CD1d protein complex. Choosing and testing various ceramide-like glycolipid antigens for their effect on cytokine release from NKT or other immune cells can be performed using in vitro assays described elsewhere herein and in Porcelli, U.S. Patent Appl. Publ. No. 2006/0052316, as well as by additional methods well-known to those of ordinary skill in the art. Administration of the modified glycolipids and modified glycolipid/protein complexes of the present invention (e.g., modified ceramide-like glycolipid/CD1d complexes) and vaccine compositions comprising the same may further modulate an immune response by inducing proliferation of NKT cells, and also by inducing recruitment and or activation of other immune and inflammatory cells including, but not limited to NK cells, CTLs, other T lymphocytes, e.g., CD8+ or CD4+ T lymphocytes, dendritic cells, B lymphocytes, and others.

In certain embodiments, administration of the modified glycolipids or modified glycolipid/protein complexes of the present invention and compositions comprising the same affects one or more NKT cell activities such as, but not limited to cell proliferation, the production of one or more cytokines, or recruitment and/or activation of non-NKT immune system cells including, but not limited to NK cells, CTLs, other T lymphocytes, e.g., CD8+ or CD4+ T lymphocytes, dendritic cells, B lymphocytes, and others.

In some embodiments, the modified glycolipid is a modified ceramide-like glycolipid that shows a bias towards inducing Type 2 cytokines, i.e., cytokines that have anti-inflammatory effect, (e.g., IL-4) in iNKT cells with blunted Type 1 cytokine (e.g., IFNγ) induction. Non-limiting examples of such ceramide-like glycolipids are described in U.S. Pat. Nos. 7,772,380 and 8,022,043, each of which are herein incorporated by reference in its entirety. In some of these embodiments, the ceramide-like glycolipid has one of the following two structures.

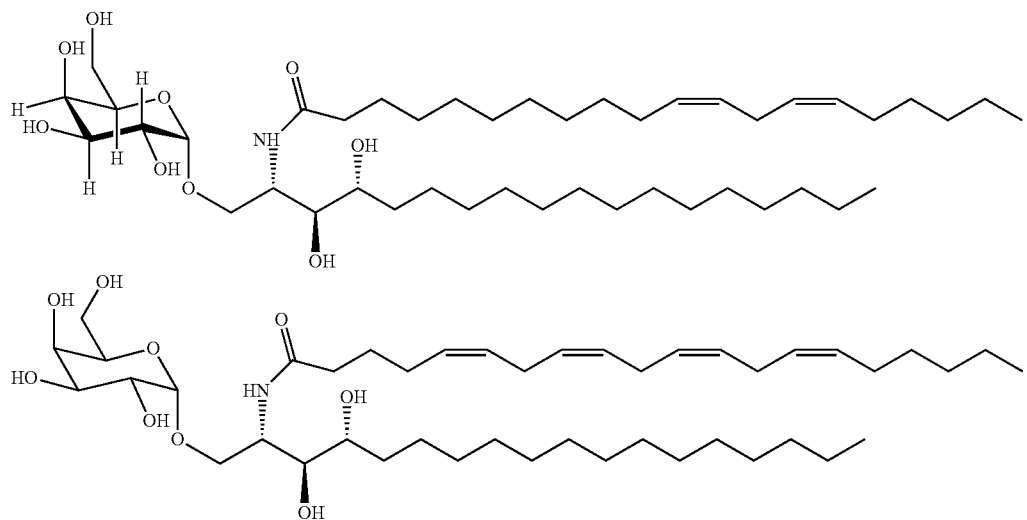

Certain embodiments of the present invention involve the use of modified glycolipids or modified glycolipid/protein complexes of the invention (e.g., modified ceramide-like glycolipid/CD1d complexes) as recombinant vaccines used to modulate an immune response to an immunogen, e.g., a pathogen antigen or tumor antigen, that is administered together or just before or soon after the modified glycolipid or modified glycolipid/protein complex (e.g., modified ceramide-like glycolipid/CD1d complex). Accordingly, the present invention provides a method of inducing an immune response to an immunogen in an animal, where the method comprises administering to an animal in need thereof a composition comprising an immunogen, which is present in a modified glycolipid/protein complex (e.g., modified ceramide-like glycolipid/CD1d complex). According to this embodiment, the modified glycolipid/CD1d complex (e.g., the modified ceramide-like glycolipid/CD1d complex) is administered in an amount sufficient to induce the immune response against the immunogen, e.g., bacterial pathogen or immunogen expressed by recombinant bacteria, relative to administration of the immunogen without the modified glycolipid/CD1d complex (e.g., modified ceramide-like glycolipid/CD1d complex). A modified glycolipid or modified glycolipid/CD1d complex for use as a vaccine can in certain embodiments be targeted to a particular organ, tissue, cell or cell surface marker as described, e.g., in U.S. Patent Appl. Publ. No. 2006/0269540, which is herein incorporated by reference in its entirety.

In certain embodiments, the modified glycolipids or modified glycolipid/protein complexes of the present invention (e.g., modified ceramide-like glycolipid/CD1d complexes) or compositions comprising the same are administered as a therapeutic vaccine, e.g., to an animal already suffering from a disease. According to these methods, the immune response elicited by a modified glycolipid or modified glycolipid/protein complex of the invention is effective in treating, e.g., affecting the outcome of the disease by reducing symptoms or lessening the severity of the disease, and the modified glycolipid or modified glycolipid/protein complex is administered in an amount sufficient to modulate the immune response against the immunogen relative to administration of the immunogen in the absence of the modified glycolipid/protein complex. Alternatively, modified glycolipids or modified glycolipid/protein complexes of the present invention (e.g., modified ceramide-like glycolipid/CD1d complexes) and compositions comprising the same are administered as a prophylactic vaccine, i.e., to prevent, or reduce symptoms to a disease, such as an infectious disease that might be contracted by that animal in the future. According to these methods, the immune response elicited by the modified glycolipids or modified glycolipid/protein complexes (e.g., modified ceramide-like glycolipid/CD1d complexes) is effective in preventing, e.g., affecting the outcome of the disease by reducing symptoms or lessening the severity of the disease, and the modified glycolipid or modified glycolipid/protein complex is administered in an amount sufficient to modulate the immune response against the immunogen relative to administration of the immunogen in the absence of the modified glycolipid or modified glycolipid/protein complex (e.g., modified ceramide-like glycolipid/CD1d complex).

The methods, modified glycolipids, modified glycolipid/protein complexes, compositions, or vaccine compositions as described herein are also useful for raising an immune response against infectious agents, e.g., a modified glycolipid/protein complex wherein the complex comprises a heterologous antigen or a targeting molecule, e.g., a viral antigen, a bacterial antigen, a fungal antigen, or a parasitic antigen. Infectious agents that can cause disease or symptoms that can be treated by the methods, modified glycolipids, modified glycolipid/protein complexes, compositions, or vaccine compositions of the invention include, but are not limited to viral, bacterial, fungal, and parasitic agents. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, measles, mumps, parainfluenza, rabies, the common cold, Polio, leukemia, Rubella, sexually transmitted diseases, skin diseases (e.g., Kaposi's, warts), and viremia.

Similarly, bacterial or fungal agents that can cause disease or symptoms can be treated or prevented by the methods, modified glycolipids, modified glycolipid/protein complexes, compositions, or vaccine compositions of the invention. These include, but are not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Hansen's disease, pulmonary disease resembling tuberculosis, Lymphadenitis, skin disease, disseminated disease, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections.

Moreover, the methods, modified glycolipids, modified glycolipid/protein complexes, compositions, or vaccine compositions of the present invention can be used to treat or prevent diseases caused by parasitic agents. Those that can be treated by the compounds of the invention include, but are not limited to, the following families: amebiasis, babesiosis, coccidiosis, cryptosporidiosis, dientamoebiasis, dourine, ectoparasitic, giardiasis, helminthiasis, leishmaniasis, theileriasis, toxoplasmosis, trypanosomiasis, and trichomonas.

According to the disclosed methods, modified glycolipids, modified glycolipid/protein complexes, compositions, or vaccine compositions for use in the methods of the present invention can be administered, for example, by intramuscular (i.m.), intravenous (i.v.), subcutaneous (s.c.), or intrapulmonary routes. Other suitable routes of administration include, but are not limited to intratracheal, transdermal, intraocular, intranasal, inhalation, intracavity, intraductal (e.g., into the pancreas), and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intraatrial (i.e., into the heart atrium) and sub arachnoid (i.e., into the sub arachnoid spaces of the brain) administration.

Compositions of the present invention further comprise a suitable carrier. Such compositions comprise a therapeutically effective amount of the modified glycolipid or the modified glycolipid/protein complex and a pharmaceutically acceptable carrier or excipient. Such a carrier includes but is not limited to saline, buffered saline, dextrose, water, glycerol, ethanol, and combinations thereof. The formulation should suit the mode of administration.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the compositions and vaccines of the present invention are pharmaceutically acceptable.

Modified glycolipids or modified glycolipid/protein complexes of the present invention (e.g., modified ceramide-like glycolipid/CD1d complexes) can be administered in pharmaceutical compositions, e.g., vaccine compositions, in combination with one or more pharmaceutically acceptable excipients, carriers, or diluents. In certain embodiments, the pharmaceutical compositions, e.g., vaccine compositions of the invention further comprise a heterologous antigen or a targeting molecule. It will be understood that, when administered to a human patient, the total single or daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition of another agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in Remington's Pharmaceutical Sciences (latest edition), Mack Publishing Company, Easton, Pa.

A composition to be used in a given preventative or therapeutic treatment will be formulated and dosed in a fashion consistent with good medical practice, taking into account the clinical condition of the individual patient (especially the side effects of prevention or treatment with the compounds alone), the site of delivery of the compound, the method of administration, the scheduling of administration, and other factors known to practitioners. The "effective amount" of the compounds of the invention for purposes herein is thus determined by such considerations.

Appropriate dosage of the compositions, e.g., vaccine compositions, of the invention to be administered to a patient will be determined by a clinician. However, as a guide, a suitable amount of a composition of the invention can be between about $10^1$ to $10^{12}$ CFU per dose, e.g., $10^1$, $10^2$, $10^3$, $10^4$, $10^5$, $10^6$, $10^7$, $10^8$, $10^9$, $10^{10}$, $10^{11}$, or $10^{12}$ CFU, suspended in 0.05 to 0.1 ml of an immunologically inert carrier, e.g., a pharmaceutical carrier. In one embodiment, an effective amount of a vaccine of the invention to induce immunity sufficient to prevent or treat, i.e., cure, ameliorate, lessen the severity of, or prevent or reduce a diseases described herein is about $10^3$ to about $10^7$ colony forming units (CFU)/kg body weight. A composition of the invention can be administered as a single dose or multiple doses. The vaccine formulations of the present invention can be employed in dosage forms such as capsules, liquid solutions, suspensions, or elixirs, for oral administration, or sterile liquid for formulations such as solutions or suspensions for, e.g., parenteral, intranasal or topical administration.

Compositions of the invention can be administered orally, intravenously, rectally, parenterally, intracisternally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Compositions, e.g, vaccine compositions, of the invention can be formulated according to known methods. Suitable preparation methods are described, for example, in *Remington's Pharmaceutical Sciences*, 16th Edition, A. Osol, ed., Mack Publishing Co., Easton, Pa. (1980), and *Remington's Pharmaceutical Sciences*, 19th Edition, A. R. Gennaro, ed., Mack Publishing Co., Easton, Pa. (1995), both of which are incorporated herein by reference in their entireties. Although the composition can be administered as an aqueous solution, it can also be formulated as an emulsion, gel, solution, suspension, lyophilized form, or any other form known in the art. In addition, the composition can contain pharmaceutically acceptable additives including, for example, diluents, binders, stabilizers, and preservatives. Once formulated, the compositions of the invention can be administered directly to the subject. The subjects to be treated can be animals; in particular, human subjects can be treated.

Compositions of the invention ordinarily will be stored in unit or multi-dose containers, for example, sealed ampules or vials, as an aqueous solution or as a lyophilized formulation for reconstitution. Mycobacterial compositions with directly incorporated glycolipid adjuvant can be lyophilized and the adjuvant activity will be recovered intact when the composition is rehydrated and suspended for injection. As an example of a lyophilized formulation, 10-ml vials are filled with 5 ml of sterile-filtered 1% (w/v) aqueous solution, and the resulting mixture is lyophilized. An infusion solution is prepared by reconstituting the lyophilized composition using water, e.g., bacteriostatic Water-for-Injection.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the compositions of the present invention can be employed in conjunction with other therapeutic compositions.

Suitable preparations of such compositions include, but are not limited to injectables, either as liquid solutions or suspensions; solid forms suitable for solution in, or suspension in liquid prior to injection, can also be prepared. The preparation can also be emulsified, or the polypeptides encapsulated in liposomes. The active ingredients are often mixed with excipients which are pharmaceutically acceptable and compatible with the active ingredient. Suitable excipients are, for example, water, saline, dextrose, glycerol, or the like and combinations thereof. In addition, if desired, the preparation can also include minor amounts of auxiliary substances such as wetting or emulsifying agents, pH buffering agents, and/or adjuvants which enhance the effectiveness of the active ingredient.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

General principles of antibody engineering are set forth in Antibody Engineering, 2nd edition, C. A. K. Borrebaeck, Ed., Oxford Univ. Press (1995). General principles of protein engineering are set forth in Protein Engineering, A Practical Approach, Rickwood, D., et al., Eds., IRL Press at Oxford Univ. Press, Oxford, Eng. (1995). General principles of antibodies and antibody-hapten binding are set forth in: Nisonoff, A., Molecular Immunology, 2nd ed., Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in Immunology, John Wiley & Sons, New York; Stites et al. (eds), Basic and Clinical—Immunology (8th ed.), Appleton & Lange, Norwalk, Conn. (1994) and Mishell and Shiigi (eds), Selected Methods in Cellular Immunology, W.H. Freeman and Co., New York (1980).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Kennett, R., et al., eds., Monoclonal Antibodies, Hybridoma: A New Dimension in Biological Analyses, Plenum Press, New York (1980); Campbell, A., "Monoclonal Antibody Technology" in Burden, R., et al., eds., Laboratory Techniques in Biochemistry and Molecular Biology, Vol. 13, Elsevere, Amsterdam (1984), Kuby Immunnology 4th ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., Cellular and Molecular Immunology Ed. 5, Elsevier Health Sciences Division (2005); Kontermann and Dubel, Antibody Engineering, Springer Verlan (2001); Sambrook and Russell, Molecular Cloning: A Laboratory Manual. Cold Spring Harbor Press (2001); Lewin, Genes VIII, Prentice Hall (2003); Harlow and Lane, Antibodies: A Laboratory Manual, Cold Spring Harbor Press (1988); Dieffenbach and Dveksler, PCR Primer Cold Spring Harbor Press (2003).

All of the references cited above, as well as all references cited herein, are incorporated herein by reference in their entireties.

All technical and scientific terms used herein have the same meaning Efforts have been made to ensure accuracy with respect to numbers used (e.g. amounts, temperature, etc.) but some experimental errors and deviations should be accounted for. It is to be noted that the term "a" or "an" entity refers to one or more of that entity; for example, "a protein" is understood to represent one or more proteins. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

EXPERIMENTAL

Example 1

Synthesis of αGalCer-Benzophenone Derivatives

The basic scheme for synthesis of α-GalCer-benzophenone derivatives is shown in FIG. 1.

Step a: General Method for Monoalkylation Procedure.

To a cold solution of the diol (10 mmol, 4.0 eq) in anhydrous DMF (40 mL) was added sodium hydride (10 mmol, 4.0 eq) in small portions at 0° C. and the mixture allowed to stir for 30 minutes. A solution of 3-bromomethyl-phenylmethanone 1 (2.5 mmol, 1.0 eq) in DMF (20 mL) was then added dropwise. The reaction mixture was allowed to stir overnight at room temperature and then taken up in water (100 mL). The resulting mixture was then extracted with CH$_2$Cl$_2$ (3×30 mL). The combined organic layers were washed with brine (30 mL), dried over anhydrous Na$_2$SO$_4$ and concentrated in vacuo. The residue was then purified by flash chromatography using Hexanes:EtOAc (5:1) as eluent.
Step b: General Method for Oxidation of the Monoalkylated Benzophenone Alcohol Derivatives to the Corresponding Carboxylic Acids.

The monoalkylated benzophenone derivatives (1 mmol) from above were dissolved in THF (20 mL) and pyridinium dichromate (PDC) (3 mmol, 3 eq) was added. The reaction mixture was allowed to stir at room temperature for 48 hours and then taken up in water (20 mL). The resulting mixture was then extracted with CH$_2$Cl$_2$ (3×30 mL). The combined organic layers were washed with brine (30 mL), dried over anhydrous Na$_2$SO$_4$ and concentrated in vacuo. The residue was then purified by flash chromatography using 10% methanol in chloroform as eluent.
Step a': 3-(Hydroxymethyl)Benzophenone 3-(hydroxymethyl)benzophenone (10 mmol) was obtained from 3-(bromomethyl)benzophenone (12 mmol) by refluxing the latter in a mixture of THF:H$_2$O (1:1) in the presence of CaCO$_3$ as described in the reported literature.
Step b': Reaction with Bromoacids.

To a cold solution of 3-(hydroxymethyl)benzophenone (1 mmol, 1 eq) in a mixture of DMF (10 ml) and hexamethylphosphoramide (HMPA) (1 ml) was added sodium hydride (NaH) (60% in mineral oil) (1.2 mmol, 1.2 eq) at 0° C. in small amounts. The reaction mixture was allowed to stir for 20 minutes before the dropwise addition of the respective bromoacids [n=5, 6, 9] (1.2 mmol, 1.2 eq) dissolved in DMF (5 ml). The reaction was left at room temperature overnight and the excess NaH was quenched using methanol. The reaction was then taken up in water (50 mL) and extracted with EtOAc (3×40 ml). The combined organic layers were washed with brine (30 mL), dried over anhydrous Na$_2$SO$_4$ and concentrated in vacuo. The residue was then purified by flash chromatography using 10% methanol in chloroform as eluent.
Step c: Formation of Acid Chloride The benzophenone carboxylic acid derivatives obtained from steps b and b' (0.5 mmol) were added to neat oxalyl chloride (1 mL) and stirred at 70° C. for 2 h, after which time the solution was cooled to room temperature and the unreacted oxalyl chloride was removed under a stream of argon. The residual volatiles were removed under reduced pressure.
Step d: Synthesis of Compounds DB11-1 (n=4), DB12-6 (n=6), DB12-7 (n=7), DB11-2 (n=8), DB12-8 (n=9), DB12-9 (n=10), DB11-3 (n=14)

The resulting crude acyl chlorides from above were dissolved in THF (1 mL) and added to a solution of amine (0.5 mmol, 1 eq) in THF/NaOAc(sat) (1:1, 1 mL). The reaction was stirred vigorously overnight after which the organic phase was removed. The aqueous phase was further extracted with THF (2×1 mL), and the combined organic phases were concentrated. The residue was finally purified by flash chromatography (gradient from CHCl$_3$ to 20% MeOH in CHCl$_3$) to give the acylated target compounds.

Example 2

Synthesis of αGalCer-Benzophenone/CD1d Complex

Figure 2:
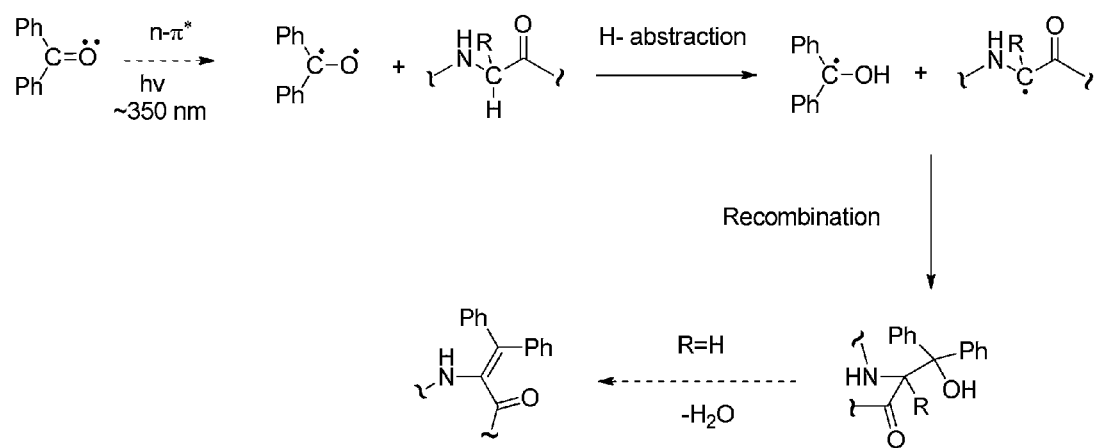
FIG. 2: shows a schematic for the synthesis of αGalCer-benzophenone/CD1d complex.

The basic scheme for synthesis of the α-GalCer-benzophenone derivatives is shown in FIG. 2.

In general, recombinant soluble murine CD1d (mCD1d) was diluted to 400 µg/ml in PBS pH 7.2. Glycolipids (i.e., benzophenone derivatives of alpha-galactosyl ceramide) were dissolved in 100% DMSO to yield 1 mg/ml final concentration and then diluted to 200 µM in PBS containing 0.1% Triton X-100. The glycolipid suspension was then heated to 80° C. for 5 minutes, vortexed for 30 seconds, sonicated in a water bath sonicator for 5 minutes, and finally vortexed for 30 seconds. Equal volumes of CD1d and glycolipid stocks were then added to give final concentrations of 200 µg/ml CD1d (~4 µM), 100 µM glycolipid and 0.05% TritonX-100, and allowed to incubate overnight (16 hrs) at room temperature. CD1d complexes were transferred to low binding 96 well plates (100 µl/well) for covalently linking the protein to the glycolipid present in its ligand binding site. A long wave UV lamp (Schleider & Schuell) emitting at fixed λ 365 was placed 1 inch above the sample level and complexes were irradiated for 1 hr on ice. The end result is that the CD1d protein is covalently bound to the αGalCer-benzophenone glycolipid.

Example 3

Tryptophan Flourescence Spectra of mCD1d with and without Glycolipid Ligands

The effect of glycolipid binding to mouse CD1d was tested. Fluorescence quenching of mCD1d due to glycolipid binding was measured using a Horibo Jobin Yvon Fluoromax-3 fluorescent spectrophotometer and the data were analyzed using FluorEssence software. Protein (0.1 µM) was mixed either with glycolipid antigens (at 4 µM) or the ligand vehicle in a quartz cuvette 1 cm wide, to a final volume of 100 µA and placed in the spectrometer already set at 25° C. The samples were excited at $\lambda_{295}$ and emission measured from $\lambda_{290}$ to $\lambda_{400}$. No shift in wavelength for fluorescence emission maximum was observed, but all of the glycolipids caused fluorescence quenching to various levels indicating that ligand binding leads to observable structural alterations in CD1d.

Figure 3:
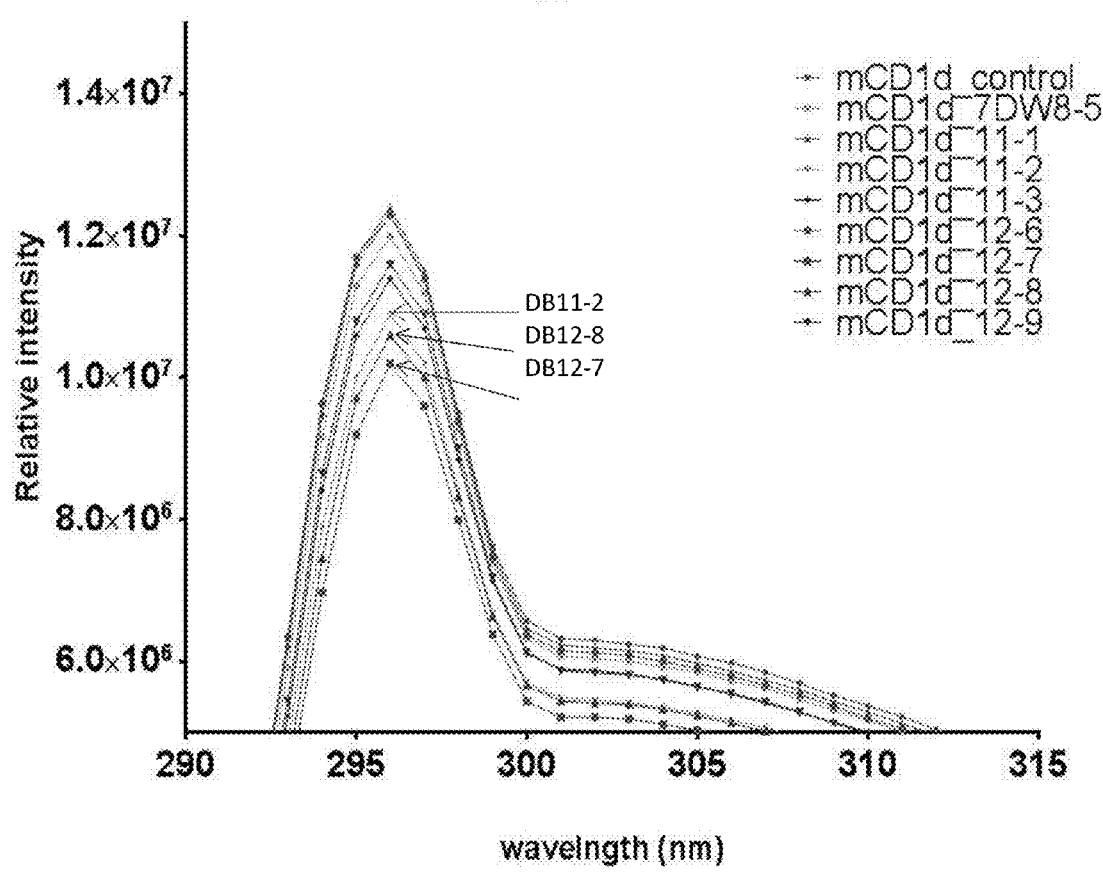
FIG. 3: shows fluorescence spectra of mouse CD1d with and without glycolipid ligands as an approach to estimating glycolipid binding. Structures of the various glycolipid ligands can be found in Table 1. 7DW8-5 is an α-GalCer analogue with a C10-fluoro-phenyl acyl moiety that does not contain photoreactive groups for formation of covalent bonds with CD1d.

The results are shown in FIG. 3. These results show that DB12-7 induced the greatest quenching compared to the other benzophenone-modified glycolipids (BPGCs), suggesting a higher binding affinity for this glycolipid compared to the others tested. Although this indicates that DB12-7 is the most avid binding ligand from this group, this analysis does not provide information on whether the complexes formed by the binding of these glycolipids result in the appropriate structure for recognition by iNKT cell antigen receptors and biological activity.

Example 4

Activation of NKT Cells (with mCD1d Expressing DCs)

The activated natural killer cells were calculated based on those secreting IL-2. Specifically, bone marrow-derived dendritic cells (BMDCs) from C57BL/6 mice (10,000 cells in 100 µA culture medium) were plated in wells of a 96 well tissue culture plate and allowed to adhere to the plates for 30 minutes at 37° C. The cultures were then exposed to varying BPGC concentrations ranging between 5 and 0.01 µg/ml in 100 µl for 3 hrs at 37° C. Glycolipids not taken up by BMDCs were removed by washing with culture medium. To detect the BPGC presentation by CD1d, iNKT hybridoma DN3A4-1.2 (5000 cells in 100 µl volume) was added and the stimulation was detected by the level of IL-2 secreted in the supernatant following 18 hrs of incubation at 37° C.

Figure 4:
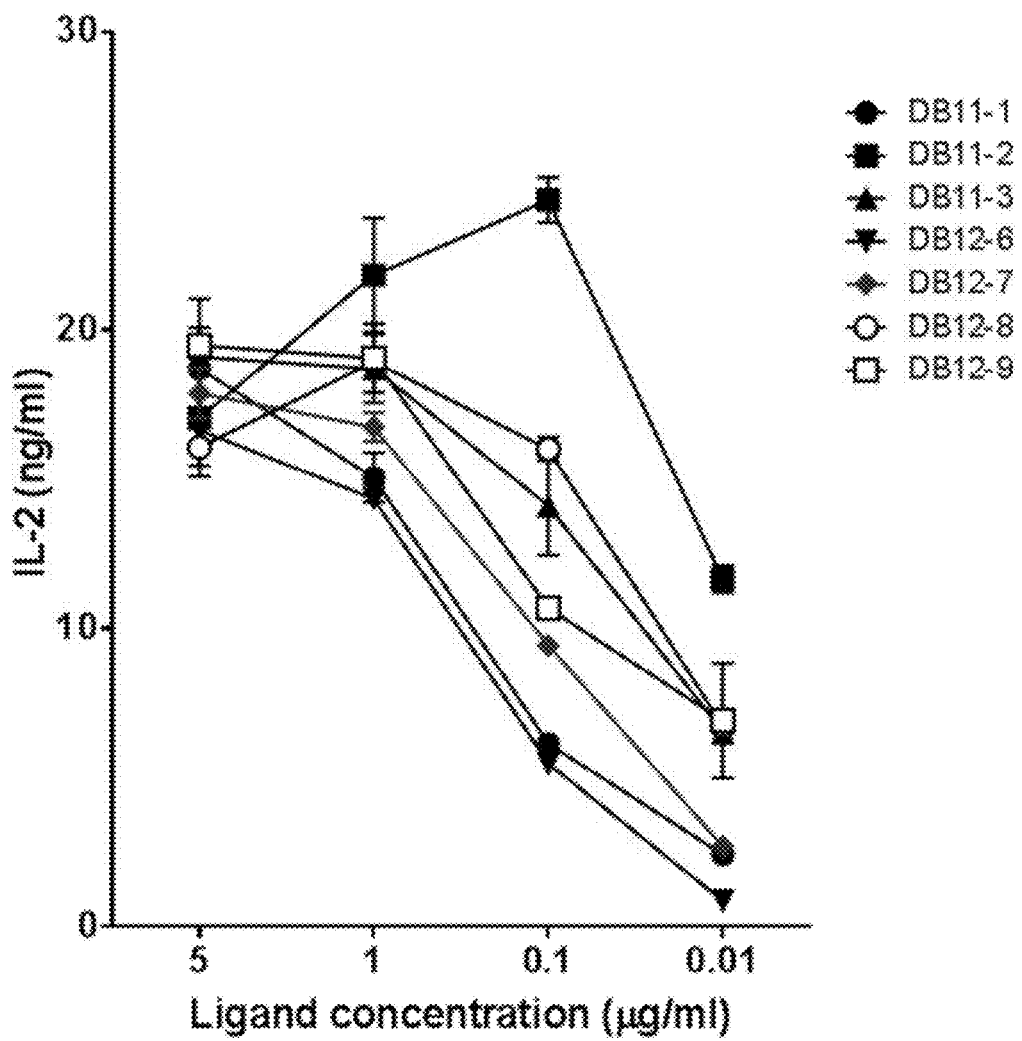
FIG. 4: shows iNKT hybridoma stimulation assay (measuring IL-2 secretion) using murine CD1d-expressing antigen presenting cells.

The results are shown in FIG. 4. These results show that DB11-2 stimulated iNKTs most efficiently at a low concentration of 0.1 µg/ml, and was the most potent in terms of biological activity in this assay among this group of glycolipids. DB12-7 induced lower but still significant IL-2 secretion.

Example 5

Activation of NKT Cells (with hCD1d Expressing HeLa Cells)

The activated natural killer cells were again calculated based on those secreting IL-2. Specifically, plate bound human CD1d transfected HeLa cells (10,000 cells in 100 µl medium) were plated in a 96 well tissue culture plate and allowed to adhere to the plates for 30 minutes at 37° C. Adherent HeLa cells were treated with varying BPGC concentrations ranging between 5 and 0.01 µg/ml in 100 µl for 3 hrs at 37° C. Glycolipid not taken up by cells was removed by washing with medium. To detect the BPGC presentation by CD1d, iNKT hybridoma DN3A4-1.2 (5000 cells in 100 µl volume) was added and the stimulation was detected by the level of IL-2 secreted in the supernatant following incubation at 37° C. for 18 hours.

Figure 5:
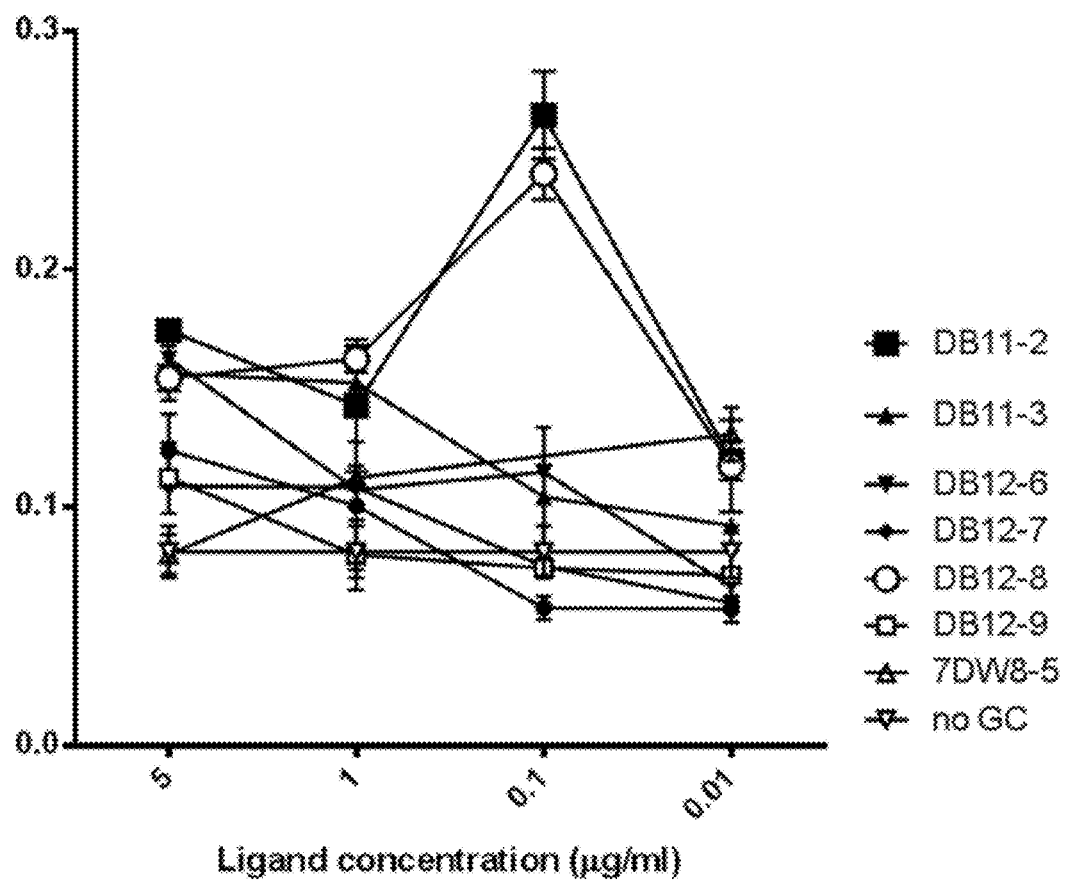
FIG. 5: shows iNKT hybridoma stimulation assay (measuring IL-2 secretion) using human CD1d-expressing HeLa cells.

The results are shown in FIG. 5. These results confirmed that DB11-2 and DB12-8 were stimulatory toward iNKT cells when presented by human CD1d, and these were efficiently presented at a low concentration of 0.1 µg/ml.

Example 6

Detection of Ligand Binding Affinity of Plate Bound mCD1d with and without UV Activation (by ELISA Using mAb L363)

The ligand binding affinity of plate bound mCD1d was measured by ELISA using mAb L363 to detect murine CD1d/αGalCer complexes. ELISA plates were coated with mCD1d (10 µg/ml, 30 µl/well) overnight at 4° C. in PBS pH 8.2. Supernatant was then removed along with any unbound protein. Glycolipids (5 µM, 30 µl/well) were loaded and allowed to incubate overnight at 25° C. Supernatant was again removed and the complexes were washed three times with PBS to remove any unbound glycolipid. For those complexes that underwent UV activation, UV crosslinking was performed in solution (30 µl/well PBS) and at a fixed wavelength of 365 nm from a UV lamp (RAD-FREE long wave UV lamp, Schleicher & Schuell). The UV lamp was placed one inch from the sample and the sample was allowed to sit on ice for 1 hr. Both the complexes that underwent UV activation and those that did not were then allowed to dissociate for three days (i. remove supernatant and add 200 µl of PBS+0.05% Triton X-100 (PBS-Tx), ii. incubate for one day at 25° C., iii. repeat steps i and ii two more times) before ELISA was performed to quantify binding of mAb L363.

Figure 6A:
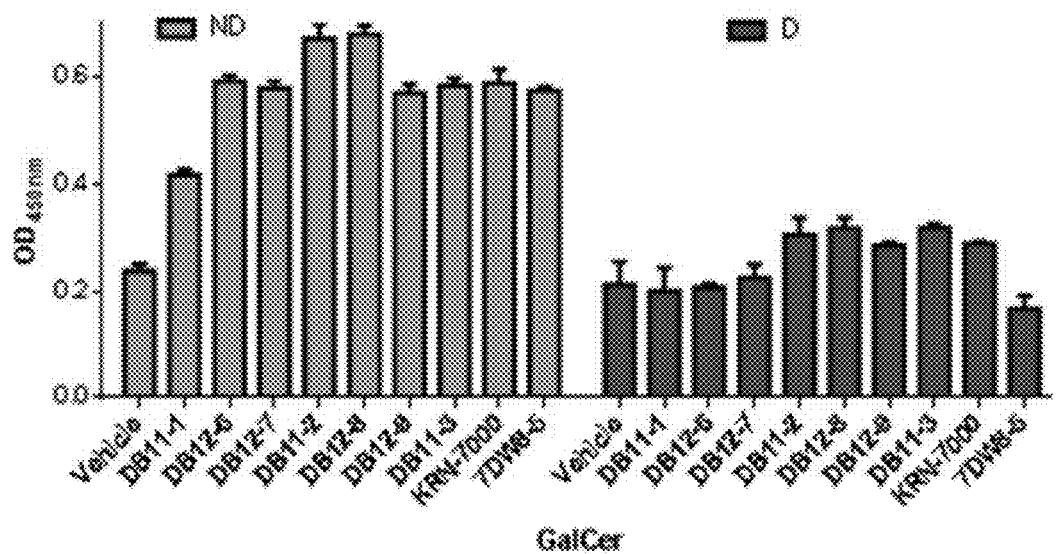
FIGS. 6A-6B: show detection of ligand binding affinity of plate-bound mCD1d by ELISA using mAb L363 to specifically detect murine CD1d/αGalCer complexes.
Figure 6B:
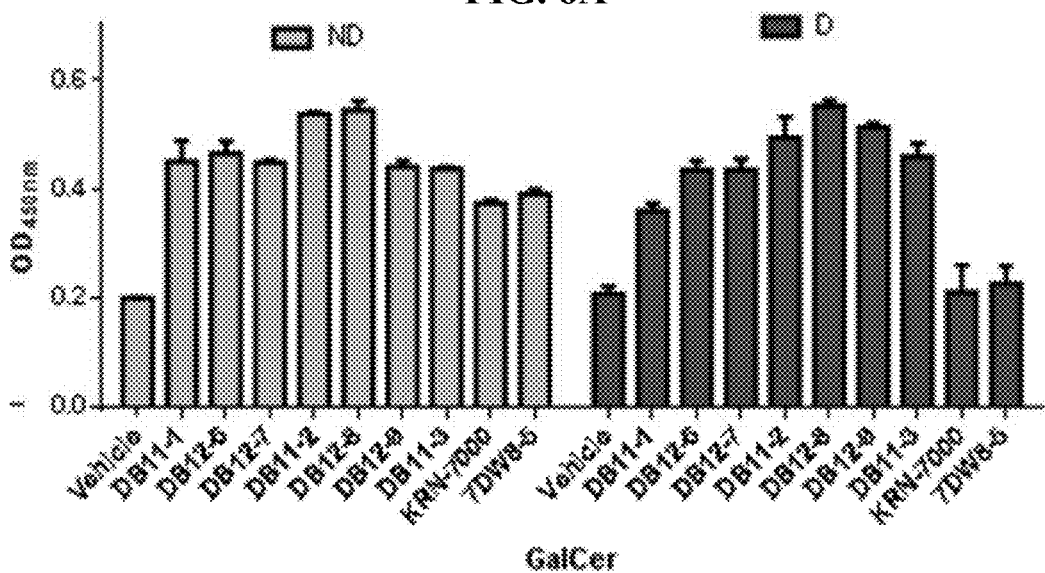

The results are shown in FIGS. 6A-6B. All of the glycolipids showing affinity for CD1d and the complexes could be detected using L363 ELISA. As a result of incubating the plate bound CD1d:GC complexes in PBS-Tx for 3 days, the non-UV crosslinked glycolipid ligands dissociated significantly (FIG. 6A), while UV cross-linked BPGCs did not (FIG. 6B). KRN7000 and 7DW8-5 do not have a UV-activatable group and hence both of them dissociated after 3 days independently of UV exposure. These results show that DB12-8, DB11-2 and DB12-9 had the highest levels of immunoreactive complex formation in this assay and that these complexes showed no significant dissociation after UV exposure.

Example 7

Detection of Ligand Binding Affinity of Plate Bound mCD1d with and without UV Activation (iNKT DN3A4-1.2 Hybridoma Stimulation Assay)

The ligand binding affinity of plate bound mCD1d was detected by iNKT DN3A4-1.2 hybridoma stimulation assay. mCD1d (10 µg/ml) was loaded with glycolipids (5 µM) overnight at 25° C. ELISA plates were coated with mCD1d:GC complexes (2.5 µg/ml, 30 µl/well) for 12-18 hours at 4° C. in PBS pH 8.2. Supernatant was then removed and the complexes were washed three times with PBS to remove any unbound glycolipid and protein. For those complexes that underwent UV activation, UV crosslinking was performed in solution (30 µl/well PBS) and at a fixed wavelength of 365 nm from a UV lamp (RAD-FREE long wave UV lamp, Schleicher & Schuell). The UV lamp was placed one inch from the sample and the sample was allowed to sit on ice for 1 hr. Supernatant was then removed and the complexes were washed three times with PBS to remove any unbound glycolipid and protein. Both the complexes that underwent UV activation and those that did not were then allowed to dissociate for three days (i. remove any residual liquid from wells and add 200 µl per well of PBS+0.05% Triton X-100, ii. incubate for 24 hours at 25° C., iii. repeat steps i and ii two more times). iNKT hybridoma DN3A4-1.2 cells (about 30,000 cells) were then added and allowed to incubate for 24 hours at 37° C. iNKT stimulatory activity of the complexes was determined by IL-2 ELISA of iNKT secretion.

7DW8-5 did not stimulate iNKT post-dissociation as expected, but non-crosslinked mCD1d complexes with DB12-7, DB11-2, DB12-8 and DB12-9 showed some, albeit reduced, iNKT stimulation even after dissociation, perhaps because the dissociation was not absolute because of high binding affinities of these glycolipids.

Figure 7A:
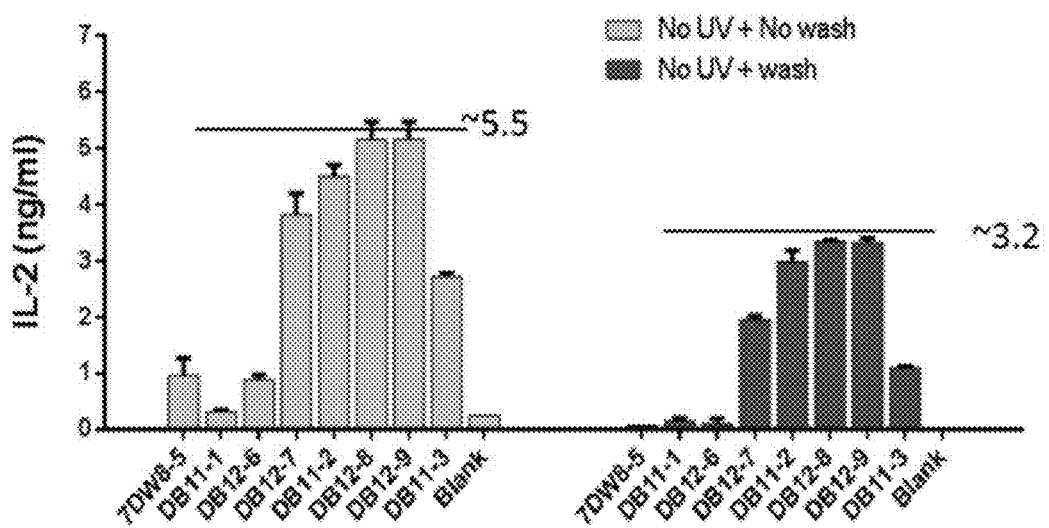
FIGS. 7A-7B: show detection of ligand binding affinity of plate-bound mCD1d by ELISA using iNKT DN3A4-1.2 hybridoma to detect murine CD1d/αGalCer complexes.
Figure 7B:
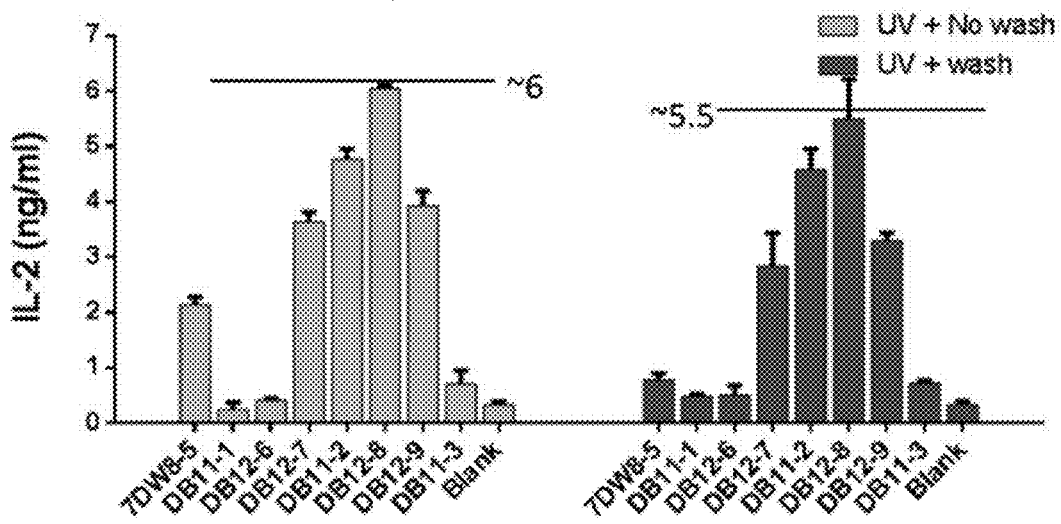

The results are shown in FIGS. 7A-7B. The results of the iNKT stimulation assay following UV crosslinking show that DB12-8 not only bound efficiently to CD1d, it also stimulated iNKT hybridoma better than other glycolipids. DB11-2 is also confirmed here as the second best stimulator of the iNKT hybridoma DN3A4-1.2.

Example 8

Direct Comparison of DB12-8 and 7DW8-5 Complexes with mCD1d (Detection by L363 ELISA)

A soluble recombinant mCD1d protein (10 µg/ml) was loaded with glycolipids (5 µM) overnight at 25° C. in PBS pH8.2 with 0.05% tyloxapol. The mCD1d:GC complexes (10 µg/ml, 30 µl/well) were coated onto the high binding ELISA plates, overnight at 4° C. UV exposure and incubation to allow dissociation over 3 days was performed as described in Examples 6 and 7.

Figure 8A:
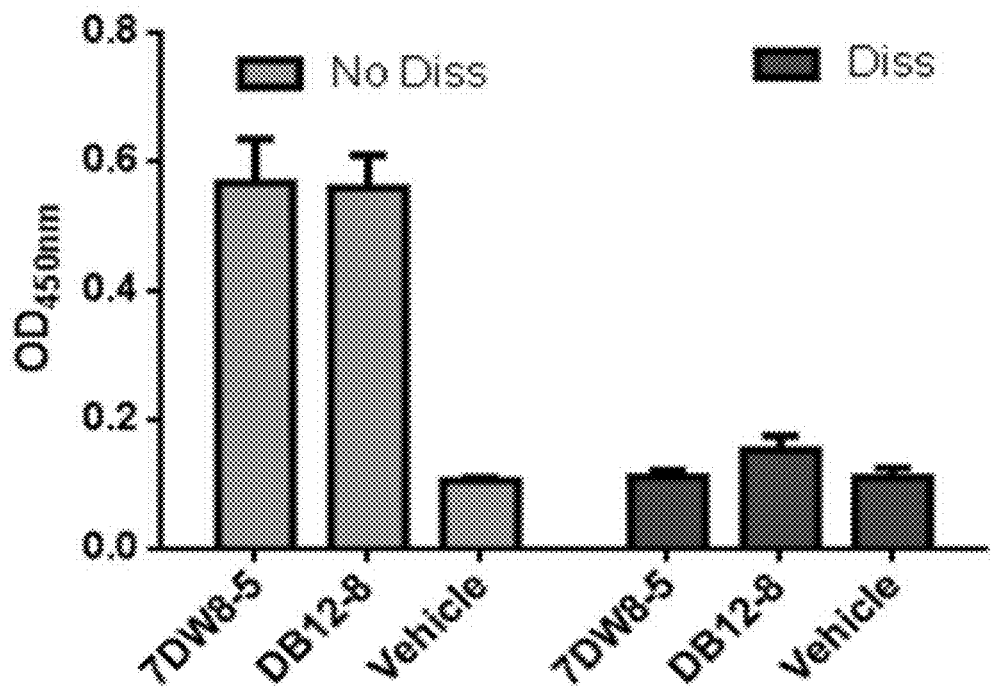
FIGS. 8A-8B: show a direct comparison of DB12-8 and 7DW8-5 complexes with mCD1d by ELISA using mAb L363.
Figure 8B:
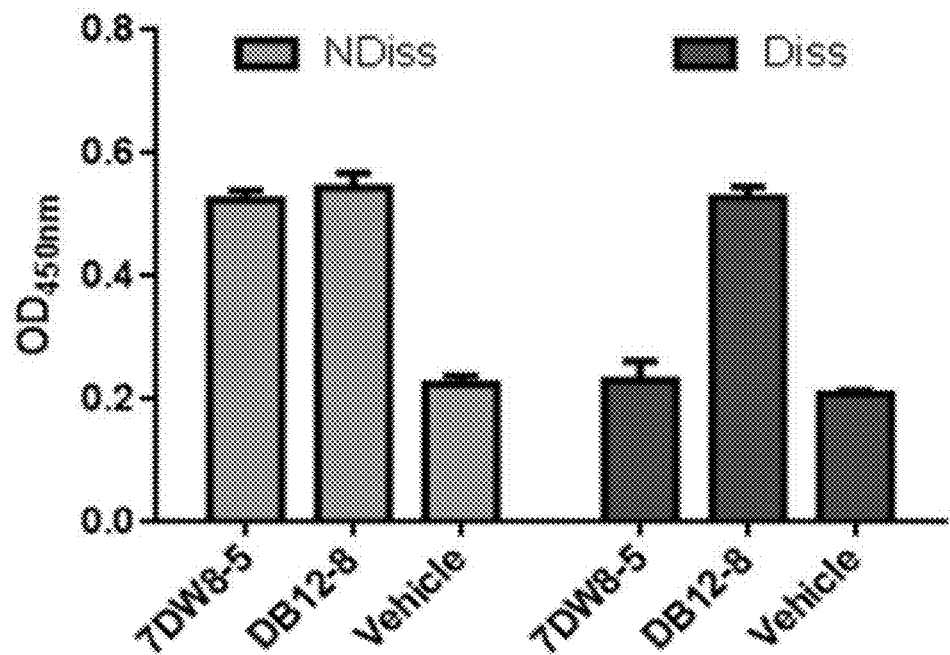

The results are shown in FIGS. 8A-8B. Both DB12-8 and 7DW8-5 showed affinity to CD1d and the complexes could be detected using L363 ELISA. Allowing extended dissociation for 3 days led to almost complete loss of signal for 7DW8-5 irrespective of UV-exposure. DB12-8 also dissociated almost completely but only in non UV-crosslinked state, UV exposure at 365 nm covalently coupled the mCD1d:DB12-8 complex and hence no dissociation was observed in this case.

Example 9

Direct Comparison of DB12-8 and 7DW8-5 Complexes with mCD1d.CEA Fusion Protein (Detection by L363 ELISA)

mCD1d.CEA (10 µg/ml), a recombinant mCD1d protein genetically fused with a single chain Fv antibody fragment specific for the tumor associated antigen CEA, was loaded with glycolipids (5 µM) overnight at 25° C. in PBS pH8.2 with 0.05% tyloxapol. The mCD1d.CEA:GC complexes (10 µg/ml, 30 µl/well) were coated onto wells of high binding ELISA 96 well plates overnight at 4° C. UV exposure and incubation to allow dissociation over 3 days were performed as described in Examples 6 and 7.

Figure 9A:
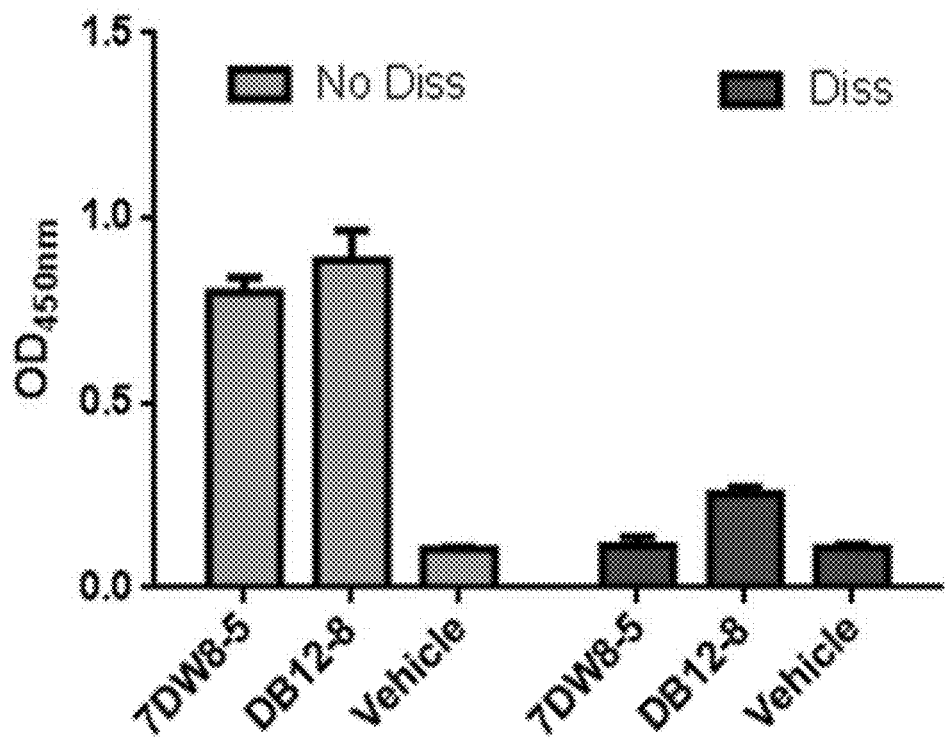
FIGS. 9A-9D.
Figure 9B:
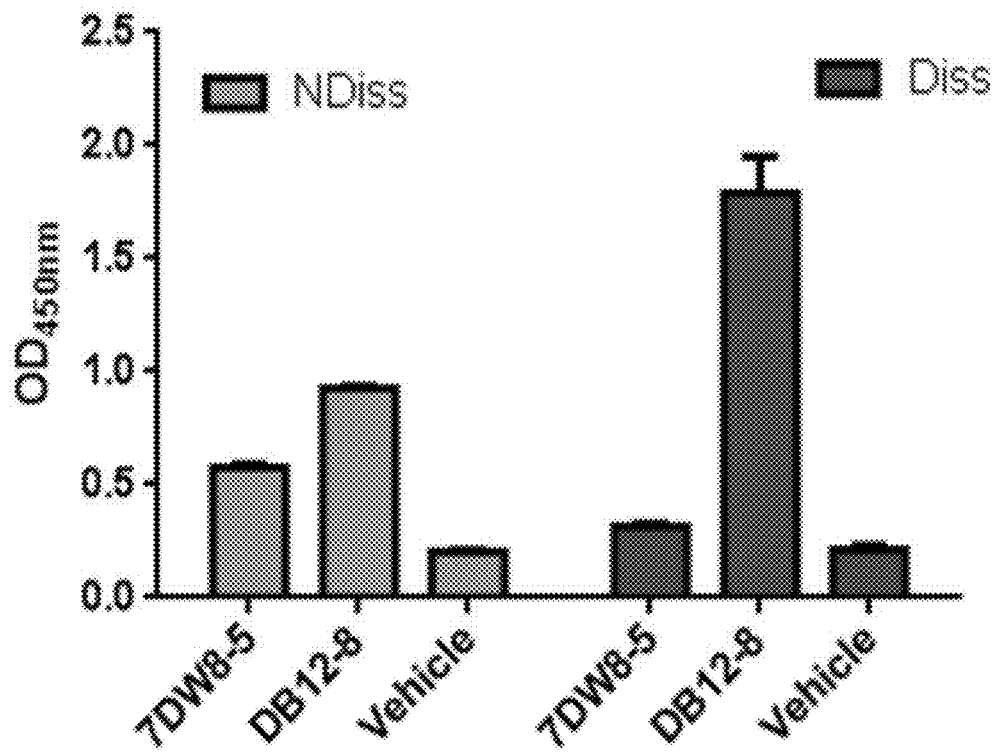

The results are shown in FIGS. 9A-9B. Both DB12-8 and 7DW8-5 showed affinity to CD1d and the complexes could be detected using L363 ELISA. Allowing extended dissociation for 3 days led to almost complete loss of signal for 7DW8-5 irrespective of UV-exposure. DB12-8 also almost completely dissociated but only in non UV-crosslinked state, UV exposure at 365 nm covalently coupled the mCD1d.CEA-DB12-8 complex and hence no dissociation was observed in this case. The results indicate that the DB12-8 signal increases significantly following UV-crosslinking.

Figure 9C:
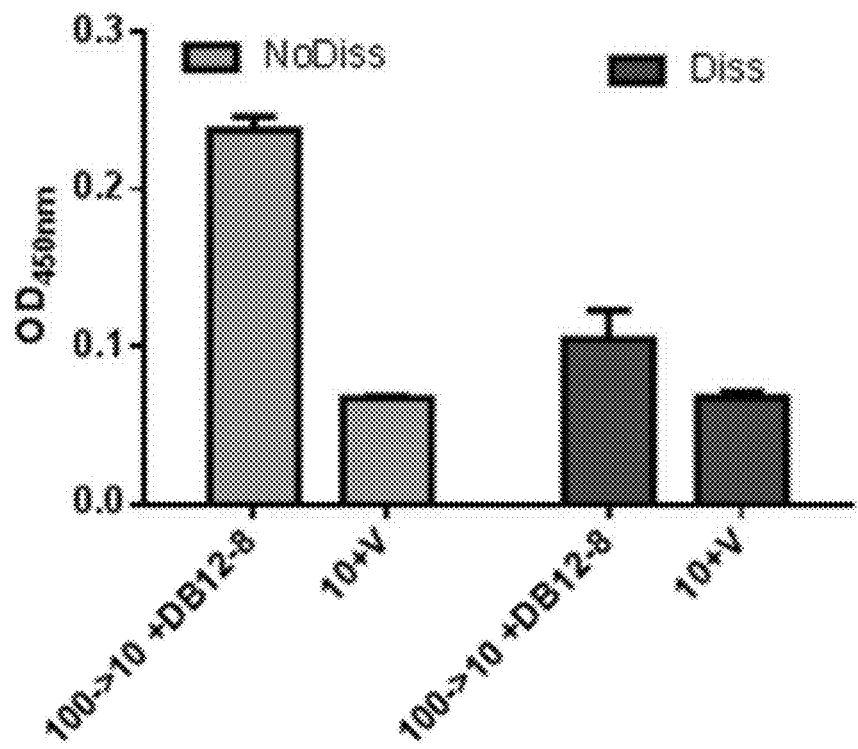
Figure 9D:
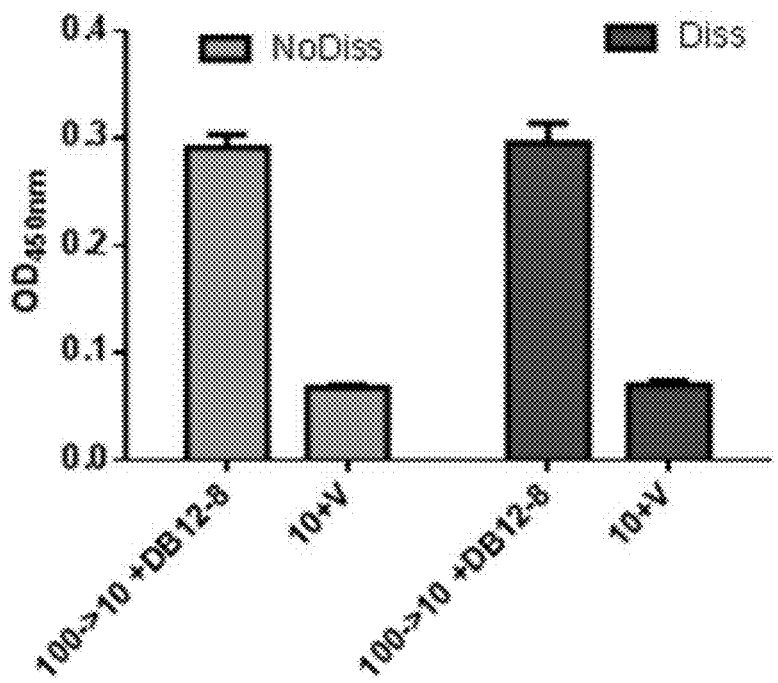

A scale up of the complex formation in solution was performed using a 10-fold increased concentration of protein and glycolipid and the results are shown in FIG. 9C-9D. mCD1d.CEA (100 µg/ml) was loaded with DB12-8 (50 µM respectively) overnight at 25° C. in PBS pH8.2 with 0.05% tyloxapol. DB12-8:mCD1d.CEA complexes were diluted down to 10 µg/ml and were coated onto the high binding ELISA plates (30 µl/well), overnight at 4° C. UV exposure and incubation to allow dissociation over 3 days were performed as described in Examples 6 and 7.

Incubation of non-crosslinked complexes for 3 days led to ~75% decrease in $OD_{450}$ whereas there was no detectable reduction in $OD_{450}$ of UV-crosslinked samples after 3 days.

Example 10

Direct Comparison of Cytokine Release In Vivo after Injection of sCD1d-Anti-CEA Non-Covalently Loaded with αGalCer or UV Cross-Linked with DB12-8

Figure 10:
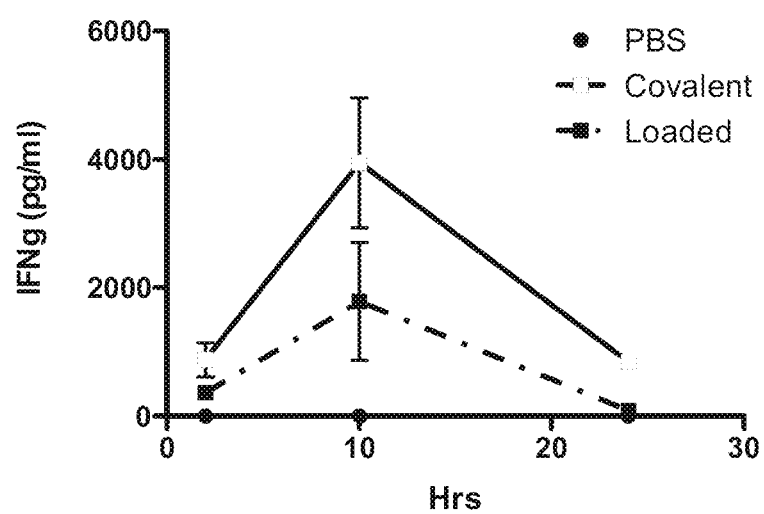
FIG. 10: shows the kinetics and magnitude of interferon γ (IFNg) and Interleukin-2 (IL-2) cytokines in serum of mice 2, 10 and 24 hrs after injection with saline or with 30 µg of either αGalCer non-covalently loaded on sCD1d-anti-CEA or UV cross-linked DB12-8:sCD1d-anti-CEA complexes.

The kinetics and magnitude of interferon γ (IFNg) and Interleukin-2 (IL-2) cytokine release in serum of groups of 3 mice each was determined at 2, 10 and 24 hrs after injection with saline or with 30 µg of either αGalCer non-covalently loaded on sCD1d-anti-CEA or UV cross-linked DB12-8: sCD1d-anti-CEA complexes. The covalently-linked DB12-8 complex with sCD1d-anti-CEA is approximately twice as potent as the non-covalently loaded fusion protein in inducing the release of IFNg and IL-2. As shown in FIG. 10, the covalent fusion protein leads to a longer duration of IFNg release.

Example 11

Sustained Production of IFNγ Upon Repeated Stimulation of iNKT Cells with DB12-8 Covalently-Linked to sCD1d-Anti-CEA Fusion Protein An important biological property of stimulation with αGalCer-loaded sCD1d is the sustained production of IFNg following repeated stimulation. This is in contrast to stimulation with free αGalCer which, as previously described, results in iNKT cell anergy (US Application Publication No. 2008/0254045A1; Stirnemann et al., J Clinical Invest. 118: 994-1005, 2008; each of which is herein incorporated by reference in its entirety). It was important to confirm that this biological property is retained by covalently linked αGalCer-CD1d complexes. Mice from the experiment described in Example 10 were further restimulated on day 2 and again on day 8 with the same agent as at the initiation of the experiment. Mice were sacrificed 1 h after the third injection and spleen iNKT cells were stained for intracellular IFNg with anti-IFNg-APC after fixation and permeabilization with Cytofix/Cytoperm (BD). To determine the percentage of iNKT that produce IFNg, iNKT cells were gated on positive staining for both CD3-FITC and αGalCer-loaded CD1d tetramer-PE and scored for expression of intracellular IFNg by flow cytometry on a FACS Calibur.

Figure 11:
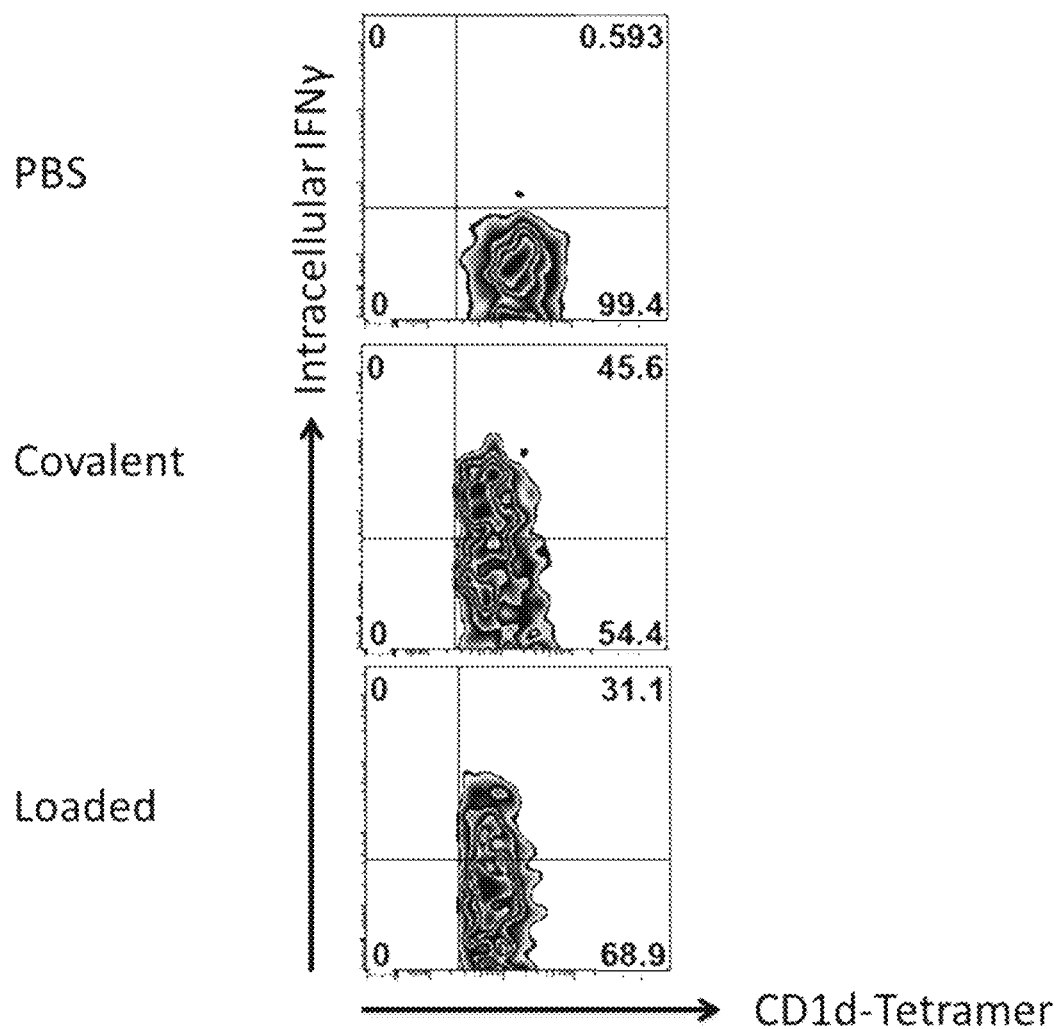
FIG. 11: shows intracellular IFNg production by iNKT cells following three injections with saline or with 30 µg of either αGalCer non-covalently loaded on sCD1d-anti-CEA or UV cross-linked DB12-8:sCD1d-anti-CEA complexes at initiation of the experiment and again on day 2 and day 8. Mice were sacrificed 1 h after the third injection and spleen iNKT cells were stained for intracellular IFNg with anti-IFNg-APC after fixation and permeabilization with Cytofix/Cytoperm (BD). To determine the percentage of iNKT cells that produce IFNg, cells were gated on positive staining for both CD3-FITC and αGalCer-loaded CD1d tetramer-PE and scored for expression of intracellular IFNg by flow cytometry on a FACS Calibur.

As shown in FIG. 11 for representative mice, less than 1% of iNKT cells of control PBS-treated mice stained for IFNg, 31% of iNKT cells of mice stimulated with non-covalently associated αGalCer-loaded sCD1d-anti-CEA, and 46% of iNKT cells of mice stimulated with UV cross-linked DB12-8:sCD1d-anti-CEA complexes stained for intracellular IFNg. These results demonstrate that production of IFNg by iNKT cells is at least as sustained following repeated stimulation with UV cross-linked DB12-8:sCD1d-anti-CEA as with non-covalently associated αGalCer-loaded sCD1d-anti-CEA complexes. Importantly, the increased potency of the covalent fusion protein was not associated with any apparent toxicity even after multiple injections.

Example 12

In Vivo Anti-Tumor Activity of DB12-8 Covalently-Linked to sCD1d-Anti-CEA Fusion Protein and Non-Covalently Loaded αGC/sCD1d-Anti-CEA Fusion Protein Four groups of C57BL/6 mice or C57BL/6 mice transgenic for CEA are grafted s.c. in the flank with $7 \times 10^5$ MC38 tumor cells that have been stably transfected with human CEA (MC38-CEA). When tumors have grown to approximately 100 mm³, mice are treated with i.v. injections of either PBS (control), or equimolar amounts of αGalCer (0.4 µg), αGalCer non-covalently loaded onto sCD1d-anti-CEA fusion protein (40 µg), or DB12-8 covalently-linked to sCD1d-anti-CEA fusion protein (40 µg) each in 200 µl volume. Treatment is repeated every 4-5 days for a total of 5 injections. Mean tumor volume is measured every two days using the formula (length×width×thickness)/2. The kinetics of tumor growth (mm3) is determined as the mean of all mice in each group.

That which is claimed:

1. A modified ceramide-like glycolipid comprising a photoreactive group, wherein said photoreactive group has been covalently bound to the terminus of an acyl chain of the N-acyl lipophilic moiety of a ceramide-like glycolipid, wherein said photoreactive group is a benzophenone group, wherein said ceramide-like glycolipid is an α-galactosylceramide, and wherein said modified ceramide-like glycolipid is capable of binding to CD1d and enhancing the activity of natural killer T (NKT) cells.

2. The modified ceramide-like glycolipid of claim 1, wherein said acyl chain is a linear acyl chain comprising at least 11 atoms, wherein the numbering of said atoms excludes hydrogens.

3. The modified ceramide-like glycolipid of claim 2, wherein said acyl chain is selected from the group consisting of:

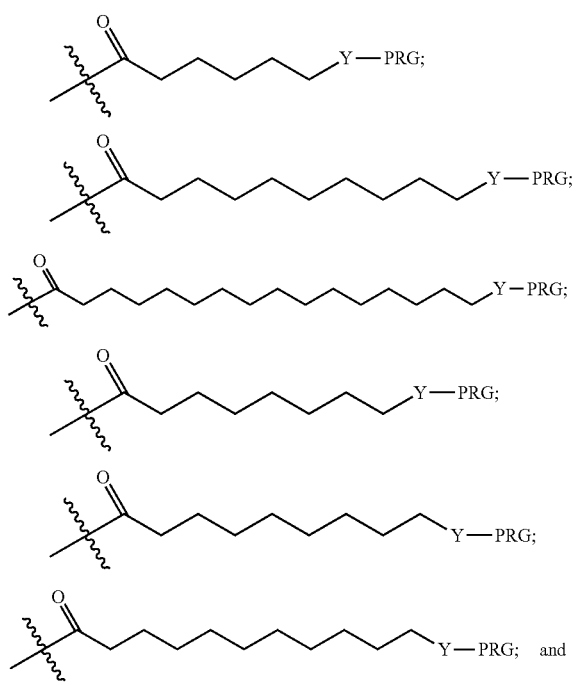

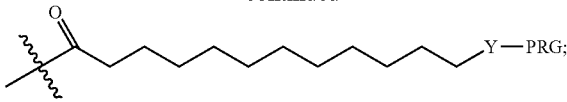

wherein Y is —O—, —CH$_2$—, —S—, —OCH$_2$—, —SCH$_2$—, —CH$_2$CH$_2$—, or a bond; and PRG is the photoreactive group.

4. The modified ceramide-like glycolipid of claim 1, wherein said α-galactosylceramide has the structure set forth in Formula II:

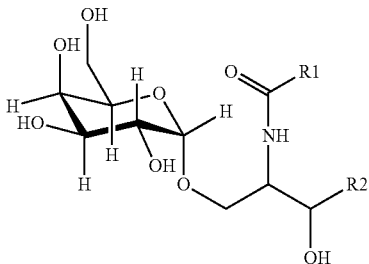

(Formula II)

wherein
R1 is a linear or branched C$_1$-C$_{27}$ alkane or C$_2$-C$_{27}$ alkene; or R1 is —C(OH)—R3 wherein R3 is linear or branched C$_1$-C$_{26}$ alkane or C$_2$-C$_{26}$ alkene; and
R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH═CH(CH$_2$)$_x$CH$_3$,
(e) —CH(OH)(CH$_2$)$_x$CH(CH$_3$)CH$_2$CH$_3$,
wherein X is an integer ranging from 4-17.

5. The modified ceramide-like glycolipid of claim 4, wherein R2 is —CH(OH)—(CH$_2$)$_{13}$CH$_3$.

6. The modified ceramide-like glycolipid of claim 4, wherein R1 is selected from the group consisting of (CH$_2$)$_9$CH═CH—CH$_2$—CH═CH(CH$_2$)$_4$CH$_3$, (CH$_2$)$_8$CH═CH—CH$_2$—CH═CH(CH$_2$)$_4$CH$_3$, (CH$_2$)$_7$CH═CH—CH$_2$—CH═CH(CH$_2$)$_4$CH$_3$, (CH$_2$)$_3$CH═CH—CH$_2$—CH═CH—CH$_2$—CH═CH—(CH$_2$)$_4$CH$_3$, (CH$_2$)$_3$CH═CH—CH$_2$—CH═CH—CH$_2$—CH═

CH—CH$_2$—CH=CH—CH$_2$—CH=CH—CH$_2$CH$_3$, (CH$_2$)$_7$CH=CH—CH$_2$—CH=CH—(CH$_2$)$_4$CH$_3$, (CH$_2$)$_7$CH=CH—CH=CH(CH$_2$)$_5$CH$_3$, (CH$_2$)$_8$CH=CH—CH=CH(CH$_2$)$_4$CH$_3$, (CH$_2$)$_9$CH=CH—CH=CH(CH$_2$)$_5$CH$_3$, (CH$_2$)$_6$CH=CH—CH=CH—CH=CH(CH$_2$)$_4$CH$_3$, (CH$_2$)$_6$CH=CH—CH=CH—CH=CH(CH$_2$)$_4$CH$_3$ and (CH$_2$)$_7$CH=CH—CH=CH—CH=CH(CH$_2$)$_3$CH$_3$.

7. The modified ceramide-like glycolipid of claim 1, wherein said α-galactosylceramide has the structure set forth in Formula III:

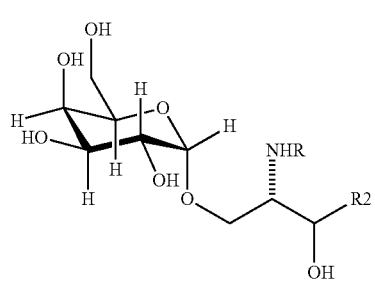

(Formula III)

wherein R is —C(O)R1, wherein R1 is a linear or branched C$_1$-C$_{27}$ alkane or C$_2$-C$_{27}$ alkene; or R1 is —C(OH)—R3 wherein R3 is a linear or branched C$_1$-C$_{26}$ alkane or C$_2$-C$_{26}$ alkene; or R1 is a C$_6$-C$_{27}$ alkane or alkene wherein (i) the C$_6$-C$_{27}$ alkane or alkene is substituted with a C$_5$-C$_{15}$ cycloalkane, C$_5$-C$_{15}$ cycloalkene, heterocycle, or aromatic ring or (ii) the C$_6$-C$_{27}$ alkane or alkene includes, within the C$_6$-C$_{27}$ alkyl or alkenyl chain, a C$_5$-C$_{15}$ cycloalkane, C$_5$-C$_{15}$ cycloalkene, heterocycle, or aromatic ring; or R1 is an optionally substituted aromatic ring, or an aralkyl, and R2 is one of the following (a)-(e):
(a) —CH$_2$(CH$_2$)$_x$CH$_3$,
(b) —CH(OH)(CH$_2$)$_x$CH$_3$,
(c) —CH(OH)(CH$_2$)$_x$CH(CH$_3$)$_2$,
(d) —CH=CH(CH$_2$)$_x$CH$_3$,
(e) —CH(OH)(CH$_2$)$_x$CH(CH$_3$)CH$_2$CH$_3$,
wherein X is an integer ranging from 4-17.

8. The modified ceramide-like glycolipid of claim 7, wherein R1 is substituted with oxo; hydroxy; halogen; phenyl; —OC(O)R6; —OR6; —C(O)R6; or N(R6)$_2$, wherein each R6 is independently a C$_1$-C$_6$ substituted alkyl, or a substituted aromatic ring optionally substituted with halogen; hydroxy; —OC(O)R7; —OR7; —C(O)R7 or N(R7)$_2$, and wherein each R7 is a substituted C$_1$-C$_6$ alkyl.

9. The modified ceramide-like glycolipid of claim 7, wherein R1 is selected from the group consisting of

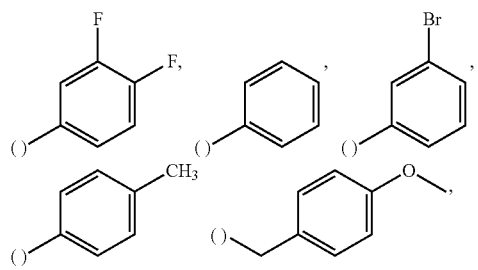

-continued

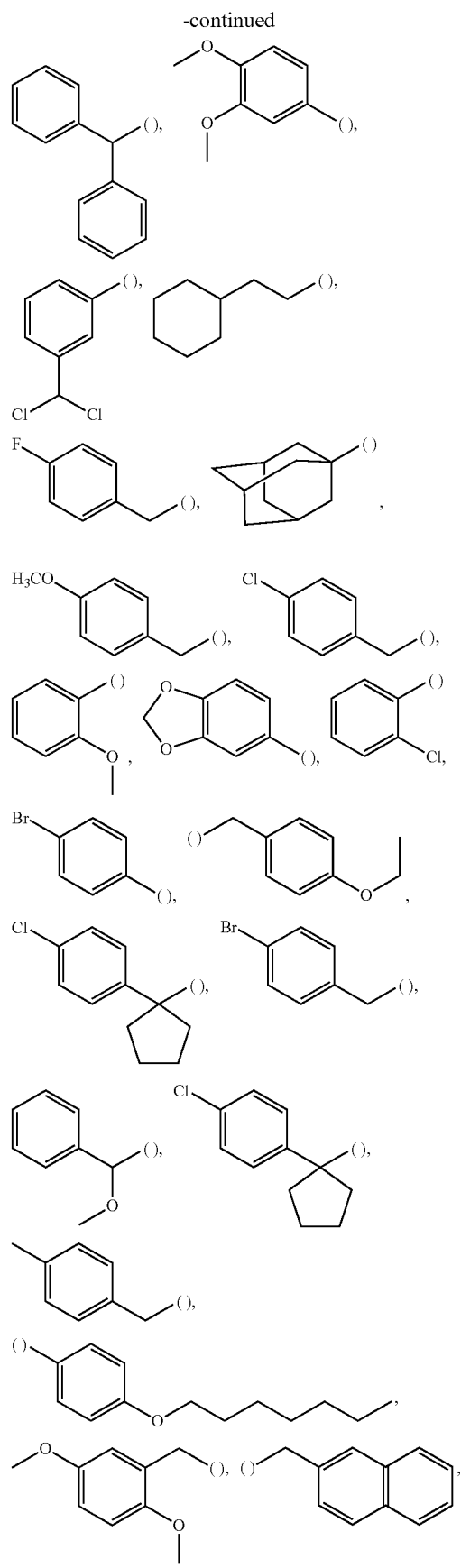

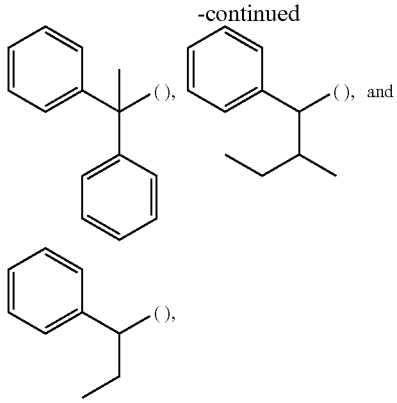

where ( ) represent the point of attachment of R1 to the compound of Formula III.

10. The modified ceramide-like glycolipid of claim 1, wherein said α-galactosylceramide is selected from the group consisting of: (2S,3S,4R)-1-O-(α-D-galactopyranosyl)-N-hexacosanoyl-2-amino-1,3,4-octadecanetriol (KRN7000), (2S,3S)-1-O-(α-D-galactopyranosyl)-N-hexacosanoyl-2-amino-1,3-octadecanediol), and (2S,3S,4R)-1-CH$_2$-(α-galactopyranosyl)-N-hexacosanoyl-2-amino-1,3,4-octadecanetriol (α-C-GalCer).

11. The modified ceramide-like glycolipid of claim 1, wherein said modified glycolipid has a structure selected from the group consisting of:

a)
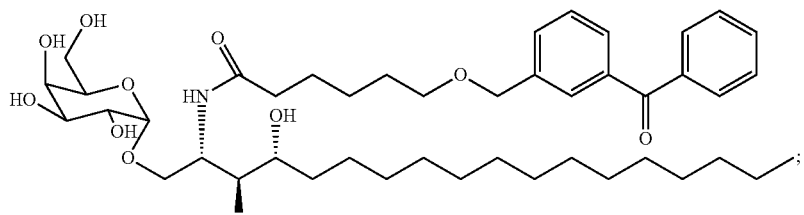

b)
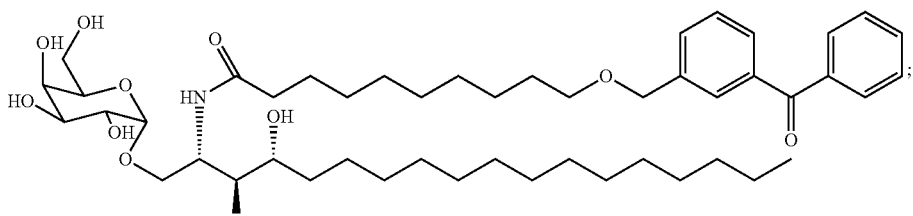

c)
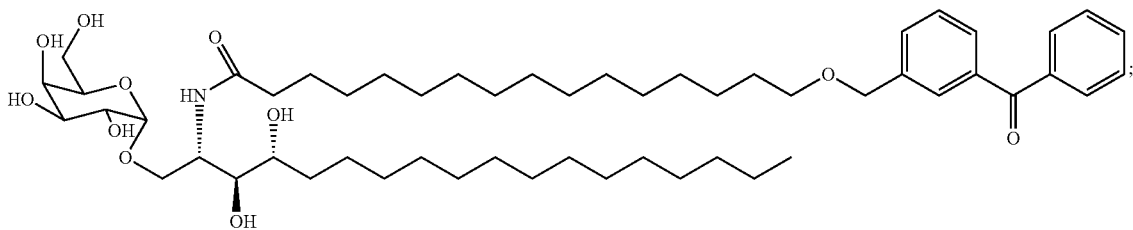

d)
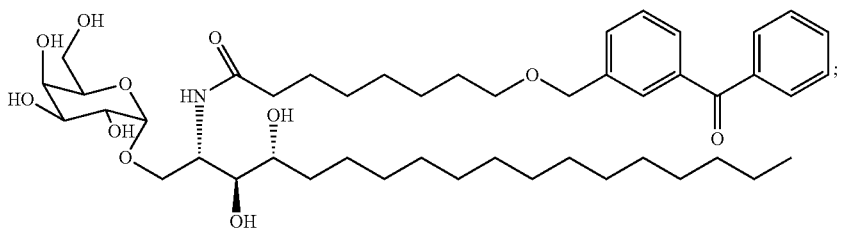

e)
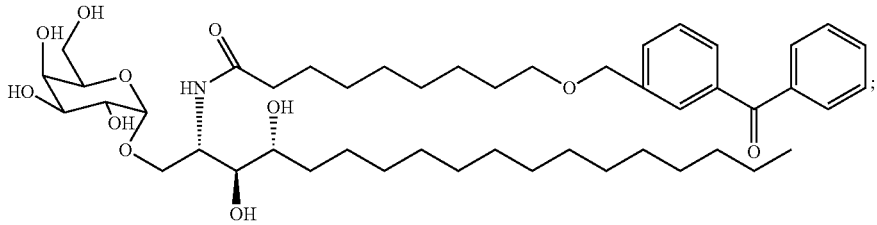

-continued f)
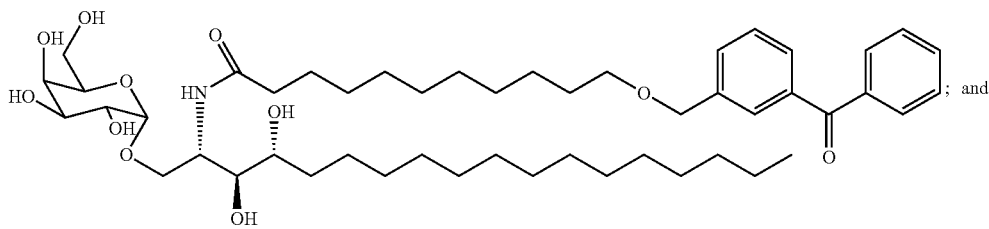

g)
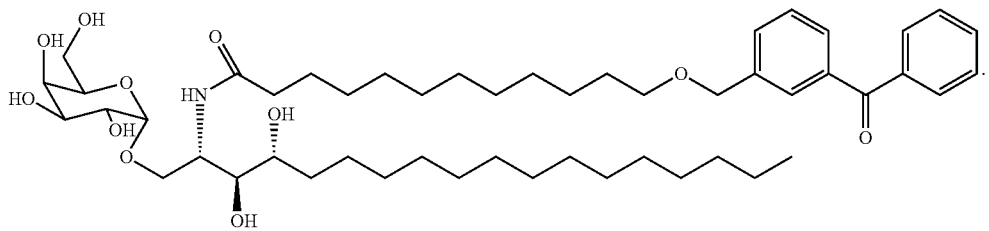

12. A method for synthesizing a modified glycolipid of Formula (VI) comprising a benzophenone group, said method comprising the steps of:

activating a carboxylic acid derivative of Formula (IV) to form an activated acyl derivative

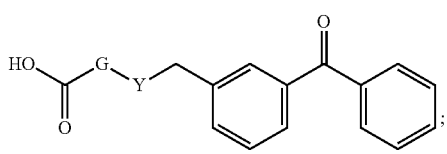
(IV)

and coupling the activated acyl derivative with a glycolipid of Formula (V)

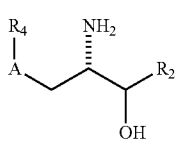
(V)

thereby forming the modified glycolipid comprising a benzophenone group of Formula (VI)

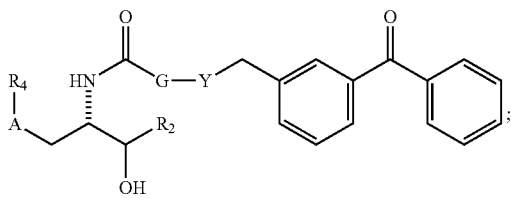
(VI)

wherein

G is a linear or branched $C_1$-$C_{27}$ alkane or $C_2$-$C_{27}$ alkene; or G is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is an optionally substituted aromatic ring, or an aralkyl;

$R_4$ is an α-linked galactoside;

A is —O—, —$CH_2$—, or is a single bond,

Y is —O—, —$CH_2$— or —S—, and $R_2$ is a substituted or an unsubstituted $C_3$-$C_{40}$ alkyl, alkenyl or alkynyl chain; and wherein said said modified glycolipid is capable of binding to CD1d and enhancing the activity of natural killer T (NKT) cells.

13. The method according to claim 12, wherein R2 of the modified glycolipid comprising a benzophenone group of Formula (VI) is selected from the group consisting of:
(a) —$CH_2(CH_2)_xCH_3$,
(b) —$CH(OH)(CH_2)_xCH_3$,
(c) —$CH(OH)(CH_2)_xCH(CH_3)_2$,
(d) —CH═$CH(CH_2)_xCH_3$, and
(e) —$CH(OH)(CH_2)_xCH(CH_3)CH_2CH_3$, wherein x is an integer ranging from 0-40.

14. The method according to claim 12, wherein:
G is —$(CH_2)_n$-, wherein n is an integer ranging from 0-20 and Y is O;
R2 is —$CH(OH)(CH_2)_xCH_3$, wherein x is an integer ranging from 4-17;
A is O; and
Y is O.

15. A modified glycolipid/protein complex comprising: a CD1d protein and the modified ceramide-like glycolipid of claim 1, wherein said modified glycolipid is physically associated with said CD1d protein.

16. The modified glycolipid/protein complex of claim 15, wherein said modified glycolipid/protein complex further comprises a β2-microglobulin physically associated with said CD1d.

17. The modified glycolipid/protein complex of claim 16, wherein said modified glycolipid/protein complex enhances the activity of Natural Killer T (NKT) cells.

18. A modified glycolipid/protein complex comprising:
a) a CD1d protein;
b) a β2-microglobulin physically associated with said CD1d protein; and
c) a modified ceramide-like glycolipid;
wherein said modified ceramide-like glycolipid is covalently linked to said CD1d protein via photoactivation of a modified ceramide-like glycolipid of claim 1, and wherein said modified glycolipid/protein complex enhances the activity of natural killer T (NKT) cells.

19. The modified glycolipid/protein complex of claim 18, wherein said modified glycolipid/protein complex further comprises an antibody or fragment thereof specific for a target antigen, and wherein said antibody or antigen-binding fragment thereof is linked to said CD1d.

20. The modified glycolipid/protein complex of claim 19, wherein said target antigen is a cell surface marker of tumor cells.

21. The modified glycolipid/protein complex of claim 20, wherein said cell surface marker is selected from the group consisting of CEA, Her2/neu, EGFR type I or type II, CD19, CD20, CD22, Muc-1, PSMA, or STEAP.

22. The modified glycolipid/protein complex of claim 18, further comprising an antigen.

23. The modified glycolipid/protein complex of claim 22, wherein said antigen is an immunogenic polypeptide of a virus or a cell selected from the group consisting of a virus, bacterium, fungus, and tumor cell.

24. A composition comprising the modified glycolipid/protein complex of claim 18, and a pharmaceutical carrier.

25. A method for producing a modified glycolipid/protein complex, said method comprising the steps of:
a) contacting the modified ceramide-like glycolipid of claim 1 with a CD1d protein; and
b) irradiating said modified glycolipid and said CD1d protein with ultraviolet light to produce a modified glycolipid/protein complex.

26. A method of inducing or enhancing an immune response against a tumor in a subject, comprising administering to said subject the modified glycolipid/protein complex of claim 20.

27. The method of claim 26, wherein said modified glycolipid/protein complex is administered in an amount sufficient to enhance the activity of Natural Killer T (NKT) cells in said subject.

28. The method of claim 26, wherein said cell surface marker is selected from the group consisting of CEA, Her2/neu, EGFR type I or type II, CD19, CD20, CD22, Muc-1, PSMA, or STEAP.

29. A method for enhancing an immune response in a subject to a heterologous antigen, wherein said method comprises administering to said subject said heterologous antigen and the modified glycolipid/protein complex of claim 18 simultaneously, prior to, or subsequent to the administration of said heterologous antigen, and wherein said heterologous antigen comprises an immunogenic polypeptide.

* * * * *

SEQUENCE LISTING

<160> NUMBER OF SEQ ID NOS: 2

<210> SEQ ID NO 1
<211> LENGTH: 335
<212> TYPE: PRT

<213> ORGANISM: Homo sapiens

<400> SEQUENCE: 1

```
Met Gly Cys Leu Leu Phe Leu Leu Leu Trp Ala Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205

Leu Ser Arg Gly Pro Ser Pro Gly Pro Gly Arg Leu Leu Leu Val Cys
    210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255

Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
        275                 280                 285

Gln Asp Ile Val Leu Tyr Trp Gly Gly Ser Tyr Thr Ser Met Gly Leu
    290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335
```

<210> SEQ ID NO 2
<211> LENGTH: 119
<212> TYPE: PRT
<213> ORGANISM: Homo sapiens

<400> SEQUENCE: 2

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
```

```
                    20                  25                  30
His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
            50                  55                  60

Arg Ile Glu Lys Val Glu His Ser Asp Leu Ser Phe Ser Lys Asp Trp
65                      70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met
            115
```